United States Patent
Sakata et al.

(10) Patent No.: US 11,981,088 B2
(45) Date of Patent: May 14, 2024

(54) MOLDED ARTICLE AND METHOD FOR PRODUCTION THEREOF

(71) Applicant: Spiber Inc., Tsuruoka (JP)

(72) Inventors: Kazuki Sakata, Tsuruoka (JP);
Kentaro Takahashi, Tsuruoka (JP)

(73) Assignee: Spiber Inc., Yamagata (JP)

( * ) Notice: Subject to any disclaimer, the term of this patent is extended or adjusted under 35 U.S.C. 154(b) by 774 days.

(21) Appl. No.: 17/043,820

(22) PCT Filed: Apr. 1, 2019

(86) PCT No.: PCT/JP2019/014533
§ 371 (c)(1),
(2) Date: Oct. 29, 2020

(87) PCT Pub. No.: WO2019/194146
PCT Pub. Date: Oct. 10, 2019

(65) Prior Publication Data
US 2021/0162677 A1    Jun. 3, 2021

(30) Foreign Application Priority Data
Apr. 3, 2018  (JP) .................. 2018-071896

(51) Int. Cl.
*B29C 65/14* (2006.01)
*C07K 14/435* (2006.01)
(Continued)

(52) U.S. Cl.
CPC .... *B29C 65/1403* (2013.01); *C07K 14/43518* (2013.01); *D01F 1/02* (2013.01);
(Continued)

(58) Field of Classification Search
CPC .......... C08L 3/06; C08L 89/00; C08L 87/005; C08B 31/04; C07K 14/43586;
(Continued)

(56) References Cited

U.S. PATENT DOCUMENTS 5,474,835 A    12/1995  McCarthy et al.
2004/0224406 A1 *  11/2004  Altman ............... A61L 27/3608
435/395
(Continued)

FOREIGN PATENT DOCUMENTS

CN    105951442 A    9/2016
JP    H08-073612 A    3/1996
(Continued)

OTHER PUBLICATIONS

International Search Report issued in corresponding International Patent Application No. PCT/JP2019/014533 dated Jul. 2, 2019.
(Continued)

*Primary Examiner* — Monica A Huson
(74) *Attorney, Agent, or Firm* — Morgan, Lewis & Bockius LLP

(57) ABSTRACT

Disclosed is a molded article including a modified fibroin and a water resistance-imparting material. The modified fibroin and the water resistance-imparting material may be covalently bonded.

10 Claims, 6 Drawing Sheets

Specification includes a Sequence Listing.

(51) Int. Cl.
  *D01F 1/02* (2006.01)
  *D01F 4/02* (2006.01)
  *B29K 27/12* (2006.01)
  *B29K 83/00* (2006.01)

(52) U.S. Cl.
  CPC ............ *D01F 4/02* (2013.01); *B29K 2027/12* (2013.01); *B29K 2083/00* (2013.01); *B29K 2089/00* (2013.01); *B29K 2995/0069* (2013.01)

(58) Field of Classification Search
  CPC ... C07K 14/43518; C09D 183/04; D01F 4/02; D01F 1/02; C08H 1/00; B29C 65/1403; B29K 2089/00; B29K 2083/00; B29K 2027/12; B29K 2995/0069
  See application file for complete search history.

(56) References Cited

U.S. PATENT DOCUMENTS

2008/0107822 A1 5/2008 Selwyn et al.
2013/0338632 A1* 12/2013 Kaplan ................ A61M 5/158
                                                        604/173

FOREIGN PATENT DOCUMENTS

| | | |
|---|---|---|
| JP | 2012-246580 A | 12/2012 |
| WO | 2014/175178 A1 | 10/2014 |
| WO | 2017/047504 A1 | 3/2017 |
| WO | 2017/222034 A1 | 12/2017 |
| WO | 2019/022163 A1 | 1/2019 |

OTHER PUBLICATIONS

International Preliminary Report on Patentability and Written Opinion issued in corresponding International Patent Application No. PCT/JP2019/014533 dated Oct. 15, 2020.
Koh et al., "Advancing the frontiers of silk fibroin protein-based materials for futuristic electronics and clinical wound-healing (Invited review)," Materials Science and Engineering C, 86: 151-172 (2018).
Extended European Search Report issued in counterpart European Patent Application No. 19780900.7 dated Dec. 7, 2021.

* cited by examiner

```
SEQUENCE LISTING

<160> NUMBER OF SEQ ID NOS: 40

<210> SEQ ID NO 1
<211> LENGTH: 50
<212> TYPE: PRT
<213> ORGANISM: Araneus diadematus

<400> SEQUENCE: 1

Ser Gly Cys Asp Val Leu Val Gln Ala Leu Leu Glu Val Val Ser Ala
1               5                   10                  15

Leu Val Ser Ile Leu Gly Ser Ser Ser Ile Gly Gln Ile Asn Tyr Gly
            20                  25                  30

Ala Ser Ala Gln Tyr Thr Gln Met Val Gly Gln Ser Val Ala Gln Ala
        35                  40                  45

Leu Ala
    50

<210> SEQ ID NO 2
```

```
<211> LENGTH: 30
<212> TYPE: PRT
<213> ORGANISM: Araneus diadematus

<400> SEQUENCE: 2

Ser Gly Cys Asp Val Leu Val Gln Ala Leu Leu Glu Val Val Ser Ala
1               5                   10                  15

Leu Val Ser Ile Leu Gly Ser Ser Ile Gly Gln Ile Asn
            20                  25                  30

<210> SEQ ID NO 3
<211> LENGTH: 21
<212> TYPE: PRT
<213> ORGANISM: Araneus diadematus

<400> SEQUENCE: 3

Ser Gly Cys Asp Val Leu Val Gln Ala Leu Leu Glu Val Val Ser Ala
1               5                   10                  15

Leu Val Ser Ile Leu
            20

<210> SEQ ID NO 4
<211> LENGTH: 1154
<212> TYPE: PRT
<213> ORGANISM: Artificial Sequence
<220> FEATURE:
<223> OTHER INFORMATION: recombinant spider silk protein
      ADF3KaiLargeNRSH1

<400> SEQUENCE: 4

Met His His His His His His His His Ser Ser Gly Ser Ser
1               5                   10                  15

Leu Glu Val Leu Phe Gln Gly Pro Ala Arg Ala Gly Ser Gly Gln Gln
            20                  25                  30

Gly Pro Gly Gln Gln Gly Pro Gly Gln Gln Gly Pro Gly Gln Gln Gly
        35                  40                  45

Pro Tyr Gly Pro Gly Ala Ser Ala Ala Ala Ala Ala Ala Gly Gly Tyr
    50                  55                  60

Gly Pro Gly Ser Gly Gln Gln Gly Pro Ser Gln Gln Gly Pro Gly Gln
65                  70                  75                  80

Gln Gly Pro Gly Gly Gln Gly Pro Tyr Gly Pro Gly Ala Ser Ala Ala
                85                  90                  95

Ala Ala Ala Ala Gly Gly Tyr Gly Pro Gly Ser Gly Gln Gln Gly Pro
            100                 105                 110

Gly Gln Gln Gly Pro Tyr Gly Pro Gly Ser Ser Ala Ala Ala Ala Ala
        115                 120                 125

Ala Gly Gly Asn Gly Pro Gly Ser Gly Gln Gln Gly Ala Gly Gln Gln
    130                 135                 140

Gly Pro Gly Gln Gln Gly Pro Gly Ala Ser Ala Ala Ala Ala Ala Ala
145                 150                 155                 160

Gly Gly Tyr Gly Pro Gly Ser Gly Gln Gln Gly Pro Gly Gln Gln Gly
                165                 170                 175

Pro Gly Gly Gln Gly Pro Tyr Gly Pro Gly Ala Ser Ala Ala Ala Ala
            180                 185                 190

Ala Ala Gly Gly Tyr Gly Pro Gly Ser Gly Gln Gly Pro Gly Gln Gln
        195                 200                 205

Gly Pro Gly Gly Gln Gly Pro Tyr Gly Pro Gly Ala Ser Ala Ala Ala
    210                 215                 220
```

```
Ala Ala Ala Gly Gly Tyr Gly Pro Gly Ser Gly Gln Gln Gly Pro Gly
225                 230                 235                 240
Gln Gln Gly Pro Gly Gln Gln Gly Pro Gly Gln Gly Pro Tyr Gly
            245                 250                 255
Pro Gly Ala Ser Ala Ala Ala Ala Ala Gly Gly Tyr Gly Pro Gly
        260                 265                 270
Tyr Gly Gln Gln Gly Pro Gly Gln Gln Gly Pro Gly Gln Gly Pro
        275                 280                 285
Tyr Gly Pro Gly Ala Ser Ala Ala Ser Ala Ala Gly Gly Tyr Gly
        290                 295                 300
Pro Gly Ser Gly Gln Gln Gly Pro Gly Gln Gln Gly Pro Gly Gly Gln
305                 310                 315                 320
Gly Pro Tyr Gly Pro Gly Ala Ser Ala Ala Ala Ala Ala Gly Gly
            325                 330                 335
Tyr Gly Pro Gly Ser Gly Gln Gln Gly Pro Gly Gln Gln Gly Pro Gly
                340                 345                 350
Gln Gln Gly Pro Gly Gln Gln Gly Pro Gly Gln Gln Gly Pro Tyr Gly
            355                 360                 365
Pro Gly Ala Ser Ala Ala Ala Ala Ala Gly Tyr Gly Pro Gly
        370                 375                 380
Ser Gly Gln Gln Gly Pro Gly Gln Gln Gly Pro Gly Gln Gln Gly Pro
385                 390                 395                 400
Gly Gln Gln Gly Pro Gly Gln Gln Gly Pro Gly Gln Gln Gly Pro Gly
            405                 410                 415
Gln Gln Gly Pro Gly Gln Gln Gly Pro Gly Gln Gln Gly Pro Gly Gly
            420                 425                 430
Gln Gly Ala Tyr Gly Pro Gly Ala Ser Ala Ala Ala Gly Ala Ala Gly
            435                 440                 445
Gly Tyr Gly Pro Gly Ser Gly Gln Gln Gly Pro Gly Gln Gln Gly Pro
    450                 455                 460
Gly Gln Gln Gly Pro Gly Gln Gln Gly Pro Gly Gln Gln Gly Pro Gly
465                 470                 475                 480
Gln Gln Gly Pro Gly Gln Gln Gly Pro Gly Gln Gln Gly Pro Tyr Gly
            485                 490                 495
Pro Gly Ala Ser Ala Ala Ala Ala Ala Gly Gly Tyr Gly Pro Gly
        500                 505                 510
Ser Gly Gln Gln Gly Pro Gly Gln Gln Gly Pro Gly Gln Gln Gly Pro
515                 520                 525
Gly Gly Gln Gly Pro Tyr Gly Pro Gly Ala Ala Ser Ala Ala Val Ser
530                 535                 540
Val Ser Arg Ala Arg Ala Gly Ser Gly Gln Gln Gly Pro Gly Gln Gln
545                 550                 555                 560
Gly Pro Gly Gln Gln Gly Pro Gly Gln Gln Gly Pro Tyr Gly Pro Gly
            565                 570                 575
Ala Ser Ala Ala Ala Ala Ala Gly Gly Tyr Gly Pro Gly Ser Gly
        580                 585                 590
Gln Gln Gly Pro Ser Gln Gln Gly Pro Gly Gln Gln Gly Pro Gly Gly
            595                 600                 605
Gln Gly Pro Tyr Gly Pro Gly Ala Ser Ala Ala Ala Ala Ala Gly
        610                 615                 620
Gly Tyr Gly Pro Gly Ser Gly Gln Gln Gly Pro Gly Gln Gly Pro
625                 630                 635                 640
Tyr Gly Pro Gly Ser Ser Ala Ala Ala Ala Ala Ala Gly Gly Asn Gly
```

-continued

```
                645                 650                 655
Pro Gly Ser Gly Gln Gln Gly Ala Gly Gln Gln Gly Pro Gly Gln Gln
                660                 665                 670
Gly Pro Gly Ala Ser Ala Ala Ala Ala Ala Gly Gly Tyr Gly Pro
                675                 680                 685
Gly Ser Gly Gln Gln Gly Pro Gly Gln Gln Gly Pro Gly Gln Gly
                690                 695                 700
Pro Tyr Gly Pro Gly Ala Ser Ala Ala Ala Ala Ala Gly Gly Tyr
705                 710                 715                 720
Gly Pro Gly Ser Gly Gln Gly Pro Gly Gln Gln Gly Pro Gly Gln
                725                 730                 735
Gly Pro Tyr Gly Pro Gly Ala Ser Ala Ala Ala Ala Ala Gly Gly
                740                 745                 750
Tyr Gly Pro Gly Ser Gly Gln Gln Gly Pro Gly Gln Gln Gly Pro Gly
                755                 760                 765
Gln Gln Gly Pro Gly Gln Gly Pro Tyr Gly Pro Gly Ala Ser Ala
                770                 775                 780
Ala Ala Ala Ala Ala Gly Gly Tyr Gly Pro Gly Tyr Gly Gln Gln Gly
785                 790                 795                 800
Pro Gly Gln Gln Gly Pro Gly Gln Gly Pro Tyr Gly Pro Gly Ala
                805                 810                 815
Ser Ala Ala Ser Ala Ala Ser Gly Gly Tyr Gly Pro Gly Ser Gly Gln
                820                 825                 830
Gln Gly Pro Gly Gln Gln Gly Pro Gly Gln Gln Gly Pro Tyr Gly Pro
                835                 840                 845
Gly Ala Ser Ala Ala Ala Ala Ala Gly Gly Tyr Gly Pro Gly Ser
                850                 855                 860
Gly Gln Gln Gly Pro Gly Gln Gln Gly Pro Gly Gln Gln Gly Pro Gly
865                 870                 875                 880
Gln Gln Gly Pro Gly Gln Gly Pro Tyr Gly Pro Gly Ala Ser Ala
                885                 890                 895
Ala Ala Ala Ala Gly Gly Tyr Gly Pro Gly Ser Gly Gln Gln Gly
                900                 905                 910
Pro Gly Gln Gln Gly Pro Gly Gln Gln Gly Pro Gly Gln Gln Gly Pro
                915                 920                 925
Gly Gln Gln Gly Pro Gly Gln Gln Gly Pro Gly Gln Gln Gly Pro Gly
                930                 935                 940
Gln Gln Gly Pro Gly Gln Gln Gly Pro Gly Gln Gln Gly Ala Tyr Gly
945                 950                 955                 960
Pro Gly Ala Ser Ala Ala Ala Gly Ala Ala Gly Gly Tyr Gly Pro Gly
                965                 970                 975
Ser Gly Gln Gln Gly Pro Gly Gln Gln Gly Pro Gly Gln Gln Gly Pro
                980                 985                 990
Gly Gln Gln Gly Pro Gly Gln Gln Gly Pro Gly Gln Gln Gly Pro Gly
                995                1000                1005
Gln Gln Gly Pro Gly Gln Gln Gly Pro Tyr Gly Pro Gly Ala Ser
                1010                1015                1020
Ala Ala Ala Ala Ala Gly Gly Tyr Gly Pro Gly Ser Gly Gln
                1025                1030                1035
Gln Gly Pro Gly Gln Gln Gly Pro Gly Gln Gln Gly Pro Gly Gly
                1040                1045                1050
Gln Gly Pro Tyr Gly Pro Gly Ala Ala Ser Ala Ala Val Ser Val
                1055                1060                1065
```

```
Gly Gly Tyr Gly Pro Gln Ser Ser Ser Val Pro Val Ala Ser Ala
        1070                1075                1080

Val Ala Ser Arg Leu Ser Ser Pro Ala Ala Ser Ser Arg Val Ser
    1085                1090                1095

Ser Ala Val Ser Ser Leu Val Ser Ser Gly Pro Thr Lys His Ala
    1100                1105                1110

Ala Leu Ser Asn Thr Ile Ser Ser Val Val Ser Gln Val Ser Ala
    1115                1120                1125

Ser Asn Pro Gly Leu Ser Gly Cys Asp Val Leu Val Gln Ala Leu
    1130                1135                1140

Leu Glu Val Val Ser Ala Leu Val Ser Ile Leu
    1145                1150

<210> SEQ ID NO 5
<211> LENGTH: 24
<212> TYPE: PRT
<213> ORGANISM: Artificial Sequence
<220> FEATURE:
<223> OTHER INFORMATION: His tag and start codon

<400> SEQUENCE: 5

Met His His His His His His His His His Ser Ser Gly Ser Ser
1               5                   10                  15

Leu Glu Val Leu Phe Gln Gly Pro
            20

<210> SEQ ID NO 6
<211> LENGTH: 597
<212> TYPE: PRT
<213> ORGANISM: Artificial Sequence
<220> FEATURE:
<223> OTHER INFORMATION: Met-PRT380

<400> SEQUENCE: 6

Met Gly Pro Gly Gln Gln Gly Pro Tyr Gly Pro Gly Ala Ser Ala
1               5                   10                  15

Ala Ala Ala Gly Gln Asn Gly Pro Gly Ser Gly Gln Gln Gly Pro
            20                  25                  30

Gln Ser Ala Ala Ala Ala Ala Gly Gln Tyr Gly Pro Gly Gln Gln
        35                  40                  45

Pro Gly Gln Gln Gly Pro Gly Ser Ser Ala Ala Ala Ala Gly Pro
    50                  55                  60

Gly Gln Tyr Gly Pro Gly Gln Gln Gly Pro Ser Ala Ser Ala Ala
65                  70                  75                  80

Ala Ala Gly Pro Gly Ser Gly Gln Gln Gly Pro Gly Ala Ser Ala
            85                  90                  95

Ala Ala Ala Gly Gln Tyr Gly Pro Gly Gln Gln Gly Pro Gly Gln
            100                 105                 110

Gly Pro Gly Ser Ser Ala Ala Ala Ala Gly Gln Tyr Gly Ser Gly
        115                 120                 125

Pro Gly Gln Gln Gly Pro Tyr Gly Ser Ala Ala Ala Ala Gly Pro
    130                 135                 140

Gly Ser Gly Gln Tyr Gly Gln Gly Pro Tyr Gly Pro Gly Ala Ser Ala
145                 150                 155                 160

Ala Ala Ala Ala Gly Pro Gly Gln Tyr Gly Pro Gly Gln Gln Gly Pro
                165                 170                 175

Ser Ala Ser Ala Ala Ala Ala Ala Gly Ser Gly Gln Gln Gly Pro Gly
```

```
              180             185             190
Gln Tyr Gly Pro Tyr Ala Ser Ala Ala Ala Ala Gly Gln Tyr Gly
            195             200             205
Ser Gly Pro Gly Gln Gln Gly Pro Tyr Gly Pro Gly Gln Ser Ala Ala
    210                 215                 220
Ala Ala Ala Gly Ser Gly Gln Gln Gly Pro Gly Gln Gln Gly Pro Tyr
225                 230                 235                 240
Ala Ser Ala Ala Ala Ala Ala Gly Pro Gly Gln Gln Gly Pro Tyr Gly
                245                 250                 255
Pro Gly Ser Ser Ala Ala Ala Ala Ala Gly Gln Tyr Gly Tyr Gly Pro
            260                 265                 270
Gly Gln Gln Gly Pro Tyr Gly Pro Gly Ala Ser Ala Ala Ala Ala Ala
        275                 280                 285
Gly Gln Asn Gly Pro Gly Ser Gly Gln Tyr Gly Pro Gly Gln Gln Gly
    290                 295                 300
Pro Gly Gln Ser Ala Ala Ala Ala Ala Gly Pro Gly Gln Gln Gly Pro
305                 310                 315                 320
Tyr Gly Pro Gly Ala Ser Ala Ala Ala Ala Gly Gln Tyr Gly Pro
                325                 330                 335
Gly Gln Gln Gly Pro Gly Gln Tyr Gly Pro Gly Ser Ser Ala Ala Ala
            340                 345                 350
Ala Ala Gly Pro Gly Gln Gln Gly Pro Tyr Gly Pro Gly Ser Ser Ala
        355                 360                 365
Ala Ala Ala Gly Gln Tyr Gly Pro Gly Gln Gln Gly Pro Tyr Gly
    370                 375                 380
Pro Gly Gln Ser Ala Ala Ala Ala Gly Gln Tyr Gln Gln Gly Pro
385                 390                 395                 400
Gly Gln Gln Gly Pro Tyr Gly Pro Gly Ala Ser Ala Ala Ala Ala Ala
                405                 410                 415
Gly Pro Gly Gln Gln Gly Pro Tyr Gly Pro Gly Ala Ser Ala Ala Ala
            420                 425                 430
Ala Ala Gly Pro Gly Gln Tyr Gly Pro Gly Gln Gln Gly Pro Ser Ala
        435                 440                 445
Ser Ala Ala Ala Ala Gly Gln Tyr Gly Ser Gly Pro Gly Gln Tyr
    450                 455                 460
Gly Pro Tyr Gly Pro Gly Gln Ser Ala Ala Ala Ala Gly Pro Gly
465                 470                 475                 480
Ser Gly Gln Gln Gly Gln Gly Pro Tyr Gly Pro Gly Ala Ser Ala Ala
                485                 490                 495
Ala Ala Ala Gly Gln Tyr Gly Pro Gly Gln Gln Gly Pro Tyr Gly Pro
            500                 505                 510
Gly Gln Ser Ala Ala Ala Ala Ala Gly Pro Gly Ser Gly Gln Tyr Gly
        515                 520                 525
Pro Gly Ala Ser Ala Ala Ala Ala Gly Gln Asn Gly Pro Gly Ser
    530                 535                 540
Gly Gln Tyr Gly Pro Gly Gln Gln Pro Gly Gln Ser Ala Ala Ala
545                 550                 555                 560
Ala Ala Gly Gln Tyr Gln Gln Gly Pro Gly Gln Gly Pro Tyr Gly
                565                 570                 575
Pro Gly Ala Ser Ala Ala Ala Ala Gly Pro Gly Ser Gly Gln Gln
            580                 585                 590
Gly Pro Gly Ala Ser
            595
```

<210> SEQ ID NO 7
<211> LENGTH: 590
<212> TYPE: PRT
<213> ORGANISM: Artificial Sequence
<220> FEATURE:
<223> OTHER INFORMATION: Met-PRT410

<400> SEQUENCE: 7

```
Met Gly Pro Gly Gln Gln Gly Pro Tyr Gly Pro Gly Ala Ser Ala Ala
1               5                  10                  15

Ala Ala Ala Gly Gln Asn Gly Pro Ser Gly Gln Gln Gly Pro Gly
            20                  25                  30

Gln Ser Gly Gln Tyr Gly Pro Gly Gln Gln Gly Pro Gly Gln Gln Gly
            35                  40                  45

Pro Gly Ser Ser Ala Ala Ala Ala Gly Pro Gly Gln Tyr Gly Pro
50                  55                  60

Gly Gln Gln Gly Pro Ser Ala Ser Ala Ala Ala Ala Gly Pro Gly
65                  70                  75                  80

Ser Gly Gln Gln Gly Pro Gly Ala Ser Gly Gln Tyr Gly Pro Gly Gln
                85                  90                  95

Gln Gly Pro Gly Gln Gln Gly Pro Gly Ser Ser Ala Ala Ala Ala
            100                 105                 110

Gly Gln Tyr Gly Ser Gly Pro Gly Gln Gln Gly Pro Tyr Gly Ser Ala
            115                 120                 125

Ala Ala Ala Ala Gly Pro Gly Ser Gly Gln Tyr Gly Gln Gly Pro Tyr
130                 135                 140

Gly Pro Gly Ala Ser Gly Pro Gly Gln Tyr Gly Pro Gly Gln Gln Gly
145                 150                 155                 160

Pro Ser Ala Ser Ala Ala Ala Ala Gly Ser Gly Gln Gln Gly Pro
                165                 170                 175

Gly Gln Tyr Gly Pro Tyr Ala Ser Ala Ala Ala Ala Gly Gln Tyr
            180                 185                 190

Gly Ser Gly Pro Gly Gln Gln Gly Pro Tyr Gly Pro Gly Gln Ser Gly
            195                 200                 205

Ser Gly Gln Gln Gly Pro Gly Gln Gln Gly Pro Tyr Ala Ser Ala Ala
210                 215                 220

Ala Ala Ala Gly Pro Gly Gln Gln Gly Pro Tyr Gly Pro Gly Ser Ser
225                 230                 235                 240

Ala Ala Ala Ala Ala Gly Gln Tyr Gly Tyr Gly Pro Gly Gln Gln Gly
                245                 250                 255

Pro Tyr Gly Pro Gly Ala Ser Gly Gln Asn Gly Pro Gly Ser Gly Gln
            260                 265                 270

Tyr Gly Pro Gly Gln Gln Gly Pro Gly Gln Ser Ala Ala Ala Ala Ala
            275                 280                 285

Gly Pro Gly Gln Gln Gly Pro Tyr Gly Pro Gly Ala Ser Ala Ala Ala
            290                 295                 300

Ala Ala Gly Gln Tyr Gly Pro Gly Gln Gln Gly Pro Gly Gln Tyr Gly
305                 310                 315                 320

Pro Gly Ser Ser Gly Pro Gly Gln Gln Gly Pro Tyr Gly Pro Gly Ser
                325                 330                 335

Ser Ala Ala Ala Ala Gly Gln Tyr Gly Pro Gly Gln Gln Gly Pro
            340                 345                 350

Tyr Gly Pro Gly Gln Ser Ala Ala Ala Ala Gly Gln Tyr Gln Gln
            355                 360                 365
```

```
Gly Pro Gly Gln Gln Gly Pro Tyr Gly Pro Gly Ala Ser Gly Pro Gly
        370                 375                 380

Gln Gln Gly Pro Tyr Gly Pro Gly Ala Ser Ala Ala Ala Ala Ala Gly
385                 390                 395                 400

Pro Gly Gln Tyr Gly Pro Gly Gln Gln Gly Pro Ser Ala Ser Ala Ala
                405                 410                 415

Ala Ala Ala Gly Gln Tyr Gly Ser Gly Pro Gly Gln Tyr Gly Pro Tyr
            420                 425                 430

Gly Pro Gly Gln Ser Gly Pro Gly Ser Gly Gln Gln Gly Gln Gly Pro
                435                 440                 445

Tyr Gly Pro Gly Ala Ser Ala Ala Ala Ala Gly Gln Tyr Gly Pro
            450                 455                 460

Gly Gln Gln Gly Pro Tyr Gly Pro Gly Gln Ser Ala Ala Ala Ala
465                 470                 475                 480

Gly Pro Gly Ser Gly Gln Tyr Gly Pro Gly Ala Ser Gly Gln Asn Gly
                485                 490                 495

Pro Gly Ser Gly Gln Tyr Gly Pro Gly Gln Gln Gly Pro Gly Gln Ser
                500                 505                 510

Ala Ala Ala Ala Ala Gly Gln Tyr Gln Gln Gly Pro Gly Gln Gln Gly
                515                 520                 525

Pro Tyr Gly Pro Gly Ala Ser Ala Ala Ala Ala Gly Gln Tyr Gly
        530                 535                 540

Ser Gly Pro Gly Gln Gln Gly Pro Tyr Gly Pro Gly Gln Ser Gly Ser
545                 550                 555                 560

Gly Gln Gln Gly Pro Gly Gln Gly Pro Tyr Ala Ser Ala Ala Ala
                565                 570                 575

Ala Ala Gly Pro Gly Ser Gly Gln Gly Pro Gly Ala Ser
            580                 585                 590

<210> SEQ ID NO 8
<211> LENGTH: 565
<212> TYPE: PRT
<213> ORGANISM: Artificial Sequence
<220> FEATURE:
<223> OTHER INFORMATION: Met-PRT468

<400> SEQUENCE: 8

Met Gly Pro Gly Gln Gln Gly Pro Tyr Gly Pro Gly Ala Ser Ala Ala
1               5                   10                  15

Ala Ala Ala Ala Gly Ser Asn Gly Pro Gly Ser Gly Gln Gln Gly
            20                  25                  30

Pro Gly Gln Ser Gly Gln Tyr Gly Pro Gly Gln Gln Gly Pro Gly Gln
        35                  40                  45

Gln Gly Pro Gly Ser Ser Ala Ala Ala Ala Ala Gly Pro Gly
    50                  55                  60

Gln Tyr Gly Pro Gly Gln Gln Gly Pro Ser Ala Ser Ala Ala Ala Ala
65                  70                  75                  80

Ala Ala Ala Gly Pro Gly Ser Gly Gln Gln Gly Pro Gly Ala Ser Gly
                85                  90                  95

Gln Tyr Gly Pro Gly Gln Gln Gly Pro Gly Gln Gln Gly Pro Gly Ser
            100                 105                 110

Ser Ala Ala Ala Ala Ala Ala Gly Ser Tyr Gly Ser Gly Pro Gly
        115                 120                 125

Gln Gln Gly Pro Tyr Gly Ser Ala Ala Ala Ala Ala Ala Gly Pro
            130                 135                 140
```

Gly Ser Gly Gln Tyr Gly Gln Gly Pro Tyr Gly Pro Gly Ala Ser Gly
145                 150                 155                 160

Pro Gly Gln Tyr Gly Pro Gly Gln Gly Pro Ser Ala Ser Ala Ala
        165                 170                 175

Ala Ala Ala Ala Ala Gly Ser Gly Gln Gln Gly Pro Gln Tyr Gly
            180                 185                 190

Pro Tyr Ala Ser Ala Ala Ala Ala Ala Gly Ser Tyr Gly Ser
        195                 200                 205

Gly Pro Gly Gln Gln Gly Pro Tyr Gly Pro Gln Ser Gly Ser Gly
        210                 215                 220

Gln Gln Gly Pro Gly Gln Gln Gly Pro Tyr Ala Ser Ala Ala Ala
225                 230                 235                 240

Ala Ala Ala Gly Pro Gly Gln Gln Gly Pro Tyr Gly Pro Gly Ser Ser
            245                 250                 255

Ala Ala Ala Ala Ala Ala Gly Ser Tyr Gly Tyr Gly Pro Gly Gln
            260                 265                 270

Gln Gly Pro Tyr Gly Pro Gly Ala Ser Gly Gln Asn Gly Pro Gly Ser
        275                 280                 285

Gly Gln Tyr Gly Pro Gly Gln Gln Gly Pro Gly Pro Ser Ala Ala Ala
    290                 295                 300

Ala Ala Ala Ala Gly Pro Gly Gln Gln Gly Pro Tyr Gly Pro Gly Ala
305                 310                 315                 320

Ser Ala Ala Ala Ala Ala Ala Gly Ser Tyr Gly Pro Gly Gln Gln
            325                 330                 335

Gly Pro Gly Gln Tyr Gly Pro Gly Ser Ser Gly Pro Gly Gln Gln Gly
        340                 345                 350

Pro Tyr Gly Pro Gly Ser Ser Ala Ala Ala Ala Ala Ala Gly Ser
        355                 360                 365

Tyr Gly Pro Gly Gln Gln Gly Pro Tyr Gly Pro Gly Pro Ser Ala Ala
    370                 375                 380

Ala Ala Ala Ala Ala Gly Ser Tyr Gln Gln Gly Pro Gly Gln Gln Gly
385                 390                 395                 400

Pro Tyr Gly Pro Gly Ala Ser Gly Pro Gly Gln Gln Gly Pro Tyr Gly
        405                 410                 415

Pro Gly Ala Ser Ala Ala Ala Ala Ala Ala Gly Pro Gly Gln Tyr
        420                 425                 430

Gly Pro Gly Gln Gln Gly Pro Ser Ala Ser Ala Ala Ala Ala Ala
        435                 440                 445

Ala Gly Ser Tyr Gly Ser Gly Pro Gly Gln Tyr Gly Pro Tyr Gly Pro
    450                 455                 460

Gly Gln Ser Gly Pro Gly Ser Gly Gln Gln Gly Gln Gly Pro Tyr Gly
465                 470                 475                 480

Pro Gly Ala Ser Ala Ala Ala Ala Ala Gly Ser Tyr Gly Pro
        485                 490                 495

Gly Gln Gln Gly Pro Tyr Gly Pro Gly Pro Ser Ala Ala Ala Ala
        500                 505                 510

Ala Ala Gly Pro Gly Ser Gly Gln Tyr Gly Pro Gly Ala Ser Gly Gln
        515                 520                 525

Asn Gly Pro Gly Ser Gly Gln Tyr Gly Pro Gly Gln Gln Gly Pro Gly
    530                 535                 540

Pro Ser Ala Ala Ala Ala Ala Ala Gly Pro Gly Ser Gly Gln Gln
545                 550                 555                 560

-continued

Gly Pro Gly Ala Ser
            565

<210> SEQ ID NO 9
<211> LENGTH: 2364
<212> TYPE: PRT
<213> ORGANISM: Artificial Sequence
<220> FEATURE:
<223> OTHER INFORMATION: Met-PRT799

<400> SEQUENCE: 9

Met Gly Pro Gly Gln Gln Gly Pro Tyr Gly Pro Gly Ala Ser Ala Ala
1               5                   10                  15

Ala Ala Ala Gly Gln Asn Gly Pro Gly Ser Gly Gln Gln Gly Pro Gly
            20                  25                  30

Gln Ser Gly Gln Tyr Gly Pro Gly Gln Gln Gly Pro Gly Gln Gln Gly
        35                  40                  45

Pro Gly Ser Ser Ala Ala Ala Ala Gly Pro Gly Gln Tyr Gly Pro
    50                  55                  60

Gly Gln Gln Gly Pro Ser Ala Ser Ala Ala Ala Ala Gly Pro Gly
65                  70                  75                  80

Ser Gly Gln Gln Gly Pro Gly Ala Ser Gly Gln Tyr Gly Pro Gly Gln
                85                  90                  95

Gln Gly Pro Gly Gln Gln Gly Pro Gly Ser Ser Ala Ala Ala Ala
            100                 105                 110

Gly Gln Tyr Gly Ser Gly Pro Gly Gln Gln Gly Pro Tyr Gly Ser Ala
        115                 120                 125

Ala Ala Ala Gly Pro Gly Ser Gly Gln Tyr Gly Gln Gly Pro Tyr
    130                 135                 140

Gly Pro Gly Ala Ser Gly Pro Gly Gln Tyr Gly Pro Gly Gln Gln Gly
145                 150                 155                 160

Pro Ser Ala Ser Ala Ala Ala Ala Gly Ser Gly Gln Gln Gly Pro
                165                 170                 175

Gly Gln Tyr Gly Pro Tyr Ala Ser Ala Ala Ala Ala Gly Gln Tyr
        180                 185                 190

Gly Ser Gly Pro Gly Gln Gln Gly Pro Tyr Gly Pro Gly Gln Ser Gly
    195                 200                 205

Ser Gly Gln Gln Gly Pro Gly Gln Gln Gly Pro Tyr Ala Ser Ala Ala
210                 215                 220

Ala Ala Ala Gly Pro Gly Gln Gln Gly Pro Tyr Gly Pro Gly Ser Ser
225                 230                 235                 240

Ala Ala Ala Ala Gly Gln Tyr Gly Tyr Gly Pro Gly Gln Gln Gly
                245                 250                 255

Pro Tyr Gly Pro Gly Ala Ser Gly Gln Asn Gly Pro Gly Ser Gly Gln
        260                 265                 270

Tyr Gly Pro Gly Gln Gln Gly Pro Gln Ser Ala Ala Ala Ala
    275                 280                 285

Gly Pro Gly Gln Gln Gly Pro Tyr Gly Pro Gly Ala Ser Ala Ala Ala
    290                 295                 300

Ala Ala Gly Gln Tyr Gly Pro Gly Gln Gln Gly Pro Gly Gln Tyr Gly
305                 310                 315                 320

Pro Gly Ser Ser Gly Pro Gly Gln Gln Gly Pro Tyr Gly Pro Gly Ser
                325                 330                 335

Ser Ala Ala Ala Ala Gly Gln Tyr Gly Pro Gly Gln Gln Gly Pro
        340                 345                 350

-continued

```
Tyr Gly Pro Gly Gln Ser Ala Ala Ala Ala Gly Gln Tyr Gln Gln
            355                 360                 365

Gly Pro Gly Gln Gln Gly Pro Tyr Gly Pro Gly Ala Ser Gly Pro Gly
        370                 375                 380

Gln Gln Gly Pro Tyr Gly Pro Gly Ala Ser Ala Ala Ala Ala Gly
385                 390                 395                 400

Pro Gly Gln Tyr Gly Pro Gly Gln Gly Pro Ser Ala Ser Ala Ala
                405                 410                 415

Ala Ala Ala Gly Gln Tyr Gly Ser Pro Gly Gln Tyr Gly Pro Tyr
            420                 425                 430

Gly Pro Gly Gln Ser Gly Pro Gly Ser Gly Gln Gln Gly Gln Gly Pro
        435                 440                 445

Tyr Gly Pro Gly Ala Ser Ala Ala Ala Ala Gly Gln Tyr Gly Pro
    450                 455                 460

Gly Gln Gln Gly Pro Tyr Gly Pro Gly Gln Ser Ala Ala Ala Ala
465                 470                 475                 480

Gly Pro Gly Ser Gly Gln Tyr Gly Pro Gly Ala Ser Gly Gln Asn Gly
                485                 490                 495

Pro Gly Ser Gly Gln Tyr Gly Pro Gly Gln Gln Gly Pro Gly Gln Ser
            500                 505                 510

Ala Ala Ala Ala Ala Gly Gln Tyr Gln Gln Gly Pro Gly Gln Gln Gly
        515                 520                 525

Pro Tyr Gly Pro Gly Ala Ser Ala Ala Ala Ala Gly Gln Tyr Gly
    530                 535                 540

Ser Gly Pro Gly Gln Gln Gly Pro Tyr Gly Pro Gly Gln Ser Gly Ser
545                 550                 555                 560

Gly Gln Gln Gly Pro Gly Gln Gly Pro Tyr Ala Ser Ala Ala Ala
                565                 570                 575

Ala Ala Gly Pro Gly Ser Gly Gln Gln Gly Pro Gly Ala Ser Gly Gln
            580                 585                 590

Gln Gly Pro Tyr Gly Pro Gly Ala Ser Ala Ala Ala Ala Gly Gln
        595                 600                 605

Asn Gly Pro Gly Ser Gly Gln Gln Gly Pro Gly Gln Ser Gly Gln Tyr
610                 615                 620

Gly Pro Gly Gln Gln Gly Pro Gly Gln Gly Pro Gly Ser Ser Ala
625                 630                 635                 640

Ala Ala Ala Gly Pro Gly Gln Tyr Gly Pro Gly Gln Gln Gly Pro
            645                 650                 655

Ser Ala Ser Ala Ala Ala Ala Gly Pro Gly Ser Gly Gln Gln Gly
        660                 665                 670

Pro Gly Ala Ser Gly Gln Tyr Gly Pro Gly Gln Gln Gly Pro Gly Gln
    675                 680                 685

Gln Gly Pro Gly Ser Ser Ala Ala Ala Ala Gly Gln Tyr Gly Ser
        690                 695                 700

Gly Pro Gly Gln Gln Gly Pro Tyr Gly Ser Ala Ala Ala Ala Gly
705                 710                 715                 720

Pro Gly Ser Gly Gln Tyr Gly Gln Gly Pro Tyr Gly Pro Gly Ala Ser
                725                 730                 735

Gly Pro Gly Gln Tyr Gly Pro Gly Gln Gly Pro Ser Ala Ser Ala
            740                 745                 750

Ala Ala Ala Gly Ser Gly Gln Gln Gly Pro Gly Gln Tyr Gly Pro
        755                 760                 765

Tyr Ala Ser Ala Ala Ala Ala Ala Gly Gln Tyr Gly Ser Gly Pro Gly
```

```
              770                 775                 780
    Gln Gln Gly Pro Tyr Gly Pro Gly Gln Ser Gly Ser Gly Gln Gly
    785                 790                 795                 800

Pro Gly Gln Gln Gly Pro Tyr Ala Ser Ala Ala Ala Ala Gly Pro
                    805                 810                 815

Gly Gln Gln Gly Pro Tyr Gly Pro Gly Ser Ser Ala Ala Ala Ala
                    820                 825                 830

Gly Gln Tyr Gly Tyr Gly Pro Gly Gln Gln Gly Pro Tyr Gly Pro Gly
                    835                 840                 845

Ala Ser Gly Gln Asn Gly Pro Gly Ser Gly Gln Tyr Gly Pro Gly Gln
                    850                 855                 860

Gln Gly Pro Gly Gln Ser Ala Ala Ala Ala Gly Pro Gly Gln Gln
    865                 870                 875                 880

Gly Pro Tyr Gly Pro Gly Ala Ser Ala Ala Ala Ala Gly Gln Tyr
                    885                 890                 895

Gly Pro Gly Gln Gln Gly Pro Gly Gln Tyr Gly Pro Gly Ser Ser Gly
                    900                 905                 910

Pro Gly Gln Gln Gly Pro Tyr Gly Pro Gly Ser Ser Ala Ala Ala Ala
                    915                 920                 925

Ala Gly Gln Tyr Gly Pro Gly Gln Gln Gly Pro Tyr Gly Pro Gly Gln
                    930                 935                 940

Ser Ala Ala Ala Ala Gly Gln Tyr Gln Gln Gly Pro Gly Gln Gln
    945                 950                 955                 960

Gly Pro Tyr Gly Pro Gly Ala Ser Gly Pro Gly Gln Gln Gly Pro Tyr
                    965                 970                 975

Gly Pro Gly Ala Ser Ala Ala Ala Ala Gly Pro Gly Gln Tyr Gly
                    980                 985                 990

Pro Gly Gln Gln Gly Pro Ser Ala  Ser Ala Ala Ala Ala  Ala Gly Gln
                    995                 1000                1005

Tyr Gly  Ser Gly Pro Gly Gln  Tyr Gly Pro Tyr Gly  Pro Gly Gln
        1010                1015                1020

Ser Gly  Pro Gly Ser Gly Gln  Gly Gln Gly Pro  Tyr Gly Pro
        1025                1030                1035

Gly Ala  Ser Ala Ala Ala Ala  Ala Gly Gln Tyr Gly  Pro Gly Gln
        1040                1045                1050

Gln Gly  Pro Tyr Gly Pro Gly  Gln Ser Ala Ala Ala  Ala Ala Gly
        1055                1060                1065

Pro Gly  Ser Gly Gln Tyr Gly  Pro Gly Ala Ser Gly  Gln Asn Gly
        1070                1075                1080

Pro Gly  Ser Gly Gln Tyr Gly  Pro Gly Gln Gln Gly  Pro Gly Gln
        1085                1090                1095

Ser Ala  Ala Ala Ala Ala Gly  Gln Tyr Gln Gln Gly  Pro Gly Gln
        1100                1105                1110

Gln Gly  Pro Tyr Gly Pro Gly  Ala Ser Ala Ala Ala  Ala Ala Gly
        1115                1120                1125

Gln Tyr  Gly Ser Gly Pro Gly  Gln Gln Gly Pro Tyr  Gly Pro Gly
        1130                1135                1140

Gln Ser  Gly Ser Gly Gln Gln  Gly Pro Gly Gln Gln  Gly Pro Tyr
        1145                1150                1155

Ala Ser  Ala Ala Ala Ala Ala  Gly Pro Gly Ser Gly  Gln Gln Gly
        1160                1165                1170

Pro Gly  Ala Ser Gly Gln Gln  Gly Pro Tyr Gly Pro  Gly Ala Ser
        1175                1180                1185
```

-continued

Ala Ala Ala Ala Ala Gly Gln Asn Gly Pro Gly Ser Gly Gln Gln
1190            1195            1200

Gly Pro Gly Gln Ser Gly Gln Tyr Gly Pro Gly Gln Gln Gly Pro
1205            1210            1215

Gly Gln Gln Gly Pro Gly Ser Ser Ala Ala Ala Ala Gly Pro
1220            1225            1230

Gly Gln Tyr Gly Pro Gly Gln Gly Pro Ser Ala Ser Ala Ala
1235            1240            1245

Ala Ala Ala Gly Pro Gly Ser Gly Gln Gln Pro Gly Ala Ser
1250            1255            1260

Gly Gln Tyr Gly Pro Gly Gln Gln Gly Pro Gly Gln Gln Gly Pro
1265            1270            1275

Gly Ser Ser Ala Ala Ala Ala Gly Gln Tyr Gly Ser Gly Pro
1280            1285            1290

Gly Gln Gln Gly Pro Tyr Gly Ser Ala Ala Ala Ala Gly Pro
1295            1300            1305

Gly Ser Gly Gln Tyr Gly Gln Gly Pro Tyr Gly Pro Gly Ala Ser
1310            1315            1320

Gly Pro Gly Gln Tyr Gly Pro Gly Gln Gln Gly Pro Ser Ala Ser
1325            1330            1335

Ala Ala Ala Ala Ala Gly Ser Gly Gln Gln Gly Pro Gly Gln Tyr
1340            1345            1350

Gly Pro Tyr Ala Ser Ala Ala Ala Ala Gly Gln Tyr Gly Ser
1355            1360            1365

Gly Pro Gly Gln Gln Gly Pro Tyr Gly Pro Gly Gln Ser Gly Ser
1370            1375            1380

Gly Gln Gln Gly Pro Gly Gln Gln Gly Pro Tyr Ala Ser Ala Ala
1385            1390            1395

Ala Ala Ala Gly Pro Gly Gln Gln Gly Pro Tyr Gly Pro Gly Ser
1400            1405            1410

Ser Ala Ala Ala Ala Gly Gln Tyr Gly Tyr Gly Pro Gly Gln
1415            1420            1425

Gln Gly Pro Tyr Gly Pro Gly Ala Ser Gly Gln Asn Gly Pro Gly
1430            1435            1440

Ser Gly Gln Tyr Gly Pro Gly Gln Gln Gly Pro Gly Gln Ser Ala
1445            1450            1455

Ala Ala Ala Ala Gly Pro Gly Gln Gln Gly Pro Tyr Gly Pro Gly
1460            1465            1470

Ala Ser Ala Ala Ala Ala Ala Gly Gln Tyr Gly Pro Gly Gln Gln
1475            1480            1485

Gly Pro Gly Gln Tyr Gly Pro Gly Ser Ser Gly Pro Gly Gln Gln
1490            1495            1500

Gly Pro Tyr Gly Pro Gly Ser Ser Ala Ala Ala Ala Gly Gln
1505            1510            1515

Tyr Gly Pro Gly Gln Gln Gly Pro Tyr Gly Pro Gly Gln Ser Ala
1520            1525            1530

Ala Ala Ala Gly Gln Tyr Gln Gln Gly Pro Gly Gln Gln Gly
1535            1540            1545

Pro Tyr Gly Pro Gly Ala Ser Gly Pro Gly Gln Gln Gly Pro Tyr
1550            1555            1560

Gly Pro Gly Ala Ser Ala Ala Ala Ala Gly Pro Gly Gln Tyr
1565            1570            1575

-continued

Gly Pro Gly Gln Gln Gly Pro Ser Ala Ser Ala Ala  Ala Ala Ala
    1580                1585               1590

Gly Gln Tyr Gly Ser Gly Pro Gly Gln Tyr Gly Pro  Tyr Gly Pro
    1595                1600               1605

Gly Gln Ser Gly Pro Gly Ser Gly Gln Gln Gly Gln  Gly Pro Tyr
    1610                1615               1620

Gly Pro Gly Ala Ser Ala Ala Ala Ala Gly Gln  Tyr Gly Pro
    1625                1630               1635

Gly Gln Gln Gly Pro Tyr Gly Pro Gly Gln Ser Ala  Ala Ala Ala
    1640                1645               1650

Ala Gly Pro Gly Ser Gly Gln Tyr Gly Pro Gly Ala  Ser Gly Gln
    1655                1660               1665

Asn Gly Pro Gly Ser Gly Gln Tyr Gly Pro Gly Gln  Gln Gly Pro
    1670                1675               1680

Gly Gln Ser Ala Ala Ala Ala Gly Gln Tyr Gln  Gln Gly Pro
    1685                1690               1695

Gly Gln Gln Gly Pro Tyr Gly Pro Gly Ala Ser Ala  Ala Ala Ala
    1700                1705               1710

Ala Gly Gln Tyr Gly Ser Gly Pro Gly Gln Gln Gly  Pro Tyr Gly
    1715                1720               1725

Pro Gly Gln Ser Gly Ser Gly Gln Gln Gly Pro Gly  Gln Gln Gly
    1730                1735               1740

Pro Tyr Ala Ser Ala Ala Ala Ala Gly Pro Gly  Ser Gly Gln
    1745                1750               1755

Gln Gly Pro Gly Ala Ser Gly Gln Gln Gly Pro Tyr  Gly Pro Gly
    1760                1765               1770

Ala Ser Ala Ala Ala Ala Ala Gly Gln Asn Gly Pro  Gly Ser Gly
    1775                1780               1785

Gln Gln Gly Pro Gly Gln Ser Gly Gln Tyr Gly Pro  Gly Gln Gln
    1790                1795               1800

Gly Pro Gly Gln Gln Gly Pro Gly Ser Ser Ala Ala  Ala Ala Ala
    1805                1810               1815

Gly Pro Gly Gln Tyr Gly Pro Gly Gln Gln Gly Pro  Ser Ala Ser
    1820                1825               1830

Ala Ala Ala Ala Ala Gly Pro Gly Ser Gly Gln Gln  Gly Pro Gly
    1835                1840               1845

Ala Ser Gly Gln Tyr Gly Pro Gly Gln Gln Gly Pro  Gly Gln Gln
    1850                1855               1860

Gly Pro Gly Ser Ser Ala Ala Ala Ala Gly Gln  Tyr Gly Ser
    1865                1870               1875

Gly Pro Gly Gln Gln Gly Pro Tyr Gly Ser Ala  Ala Ala Ala
    1880                1885               1890

Gly Pro Gly Ser Gly Gln Tyr Gly Gln Gly Pro Tyr  Gly Pro Gly
    1895                1900               1905

Ala Ser Gly Pro Gly Gln Tyr Gly Pro Gly Gln Gln  Gly Pro Ser
    1910                1915               1920

Ala Ser Ala Ala Ala Ala Gly Ser Gly Gln Gln  Gly Pro Gly
    1925                1930               1935

Gln Tyr Gly Pro Tyr Ala Ser Ala Ala Ala Ala  Gly Gln Tyr
    1940                1945               1950

Gly Ser Gly Pro Gly Gln Gln Gly Pro Tyr Gly Pro  Gly Gln Ser
    1955                1960               1965

Gly Ser Gly Gln Gln Gly Pro Gly Gln Gln Gly Pro  Tyr Ala Ser

```
            1970                1975                1980

Ala  Ala  Ala  Ala  Ala  Gly  Pro  Gly  Gln  Gln  Gly  Pro  Tyr  Gly  Pro
     1985                1990                1995

Gly  Ser  Ser  Ala  Ala  Ala  Ala  Gly  Gln  Tyr  Gly  Tyr  Gly  Pro
     2000                2005                2010

Gly  Gln  Gln  Gly  Pro  Tyr  Gly  Pro  Gly  Ala  Ser  Gly  Gln  Asn  Gly
     2015                2020                2025

Pro  Gly  Ser  Gly  Gln  Tyr  Gly  Pro  Gly  Gln  Gly  Pro  Gly  Gln
     2030                2035                2040

Ser  Ala  Ala  Ala  Ala  Gly  Pro  Gly  Gln  Gln  Gly  Pro  Tyr  Gly
     2045                2050                2055

Pro  Gly  Ala  Ser  Ala  Ala  Ala  Ala  Gly  Gln  Tyr  Gly  Pro  Gly
     2060                2065                2070

Gln  Gln  Gly  Pro  Gly  Gln  Tyr  Gly  Pro  Gly  Ser  Ser  Gly  Pro  Gly
     2075                2080                2085

Gln  Gln  Gly  Pro  Tyr  Gly  Pro  Gly  Ser  Ser  Ala  Ala  Ala  Ala  Ala
     2090                2095                2100

Gly  Gln  Tyr  Gly  Pro  Gly  Gln  Gln  Gly  Pro  Tyr  Gly  Pro  Gly  Gln
     2105                2110                2115

Ser  Ala  Ala  Ala  Ala  Gly  Gln  Tyr  Gln  Gln  Gly  Pro  Gly  Gln
     2120                2125                2130

Gln  Gly  Pro  Tyr  Gly  Pro  Gly  Ala  Ser  Gly  Pro  Gly  Gln  Gln  Gly
     2135                2140                2145

Pro  Tyr  Gly  Pro  Gly  Ala  Ser  Ala  Ala  Ala  Ala  Ala  Gly  Pro  Gly
     2150                2155                2160

Gln  Tyr  Gly  Pro  Gly  Gln  Gln  Gly  Pro  Ser  Ala  Ser  Ala  Ala  Ala
     2165                2170                2175

Ala  Ala  Gly  Gln  Tyr  Gly  Ser  Gly  Pro  Gly  Gln  Tyr  Gly  Pro  Tyr
     2180                2185                2190

Gly  Pro  Gly  Gln  Ser  Gly  Pro  Gly  Ser  Gly  Gln  Gln  Gly  Gln  Gly
     2195                2200                2205

Pro  Tyr  Gly  Pro  Gly  Ala  Ser  Ala  Ala  Ala  Ala  Ala  Gly  Gln  Tyr
     2210                2215                2220

Gly  Pro  Gly  Gln  Gln  Gly  Pro  Tyr  Gly  Pro  Gly  Gln  Ser  Ala  Ala
     2225                2230                2235

Ala  Ala  Ala  Gly  Pro  Gly  Ser  Gly  Gln  Tyr  Gly  Pro  Gly  Ala  Ser
     2240                2245                2250

Gly  Gln  Asn  Gly  Pro  Gly  Ser  Gly  Gln  Tyr  Gly  Pro  Gly  Gln  Gln
     2255                2260                2265

Gly  Pro  Gly  Gln  Ser  Ala  Ala  Ala  Ala  Ala  Gly  Gln  Tyr  Gln  Gln
     2270                2275                2280

Gly  Pro  Gly  Gln  Gln  Gly  Pro  Tyr  Gly  Pro  Gly  Ala  Ser  Ala  Ala
     2285                2290                2295

Ala  Ala  Ala  Gly  Gln  Tyr  Gly  Ser  Gly  Pro  Gly  Gln  Gln  Gly  Pro
     2300                2305                2310

Tyr  Gly  Pro  Gly  Gln  Ser  Gly  Ser  Gly  Gln  Gln  Gly  Pro  Gly  Gln
     2315                2320                2325

Gln  Gly  Pro  Tyr  Ala  Ser  Ala  Ala  Ala  Ala  Gly  Pro  Gly  Ser
     2330                2335                2340

Gly  Gln  Gln  Gly  Ser  Ser  Val  Asp  Lys  Leu  Ala  Ala  Ala  Leu  Glu
     2345                2350                2355

His  His  His  His  His  His
     2360
```

<210> SEQ ID NO 10
<211> LENGTH: 597
<212> TYPE: PRT
<213> ORGANISM: Artificial Sequence
<220> FEATURE:
<223> OTHER INFORMATION: Met-PRT313

<400> SEQUENCE: 10

Met Gly Pro Gly Gly Gln Gly Pro Tyr Gly Pro Gly Ala Ser Ala Ala
1               5                   10                  15

Ala Ala Ala Gly Gly Asn Gly Pro Gly Ser Gly Gln Gln Gly Pro Gly
            20                  25                  30

Gly Ser Ala Ala Ala Ala Gly Gly Tyr Gly Pro Gly Gly Gln Gly
        35                  40                  45

Pro Gly Gln Gln Gly Pro Gly Ser Ser Ala Ala Ala Ala Gly Pro
50                  55                  60

Gly Gly Tyr Gly Pro Gly Gln Gly Pro Ser Ala Ser Ala Ala Ala
65                  70                  75                  80

Ala Ala Gly Pro Gly Ser Gln Gln Gly Pro Gly Ala Ser Ala Ala
                85                  90                  95

Ala Ala Ala Gly Gly Tyr Gly Pro Gly Gly Gln Gly Pro Gly Gln Gln
                100                 105                 110

Gly Pro Gly Ser Ser Ala Ala Ala Ala Gly Gly Tyr Gly Ser Gly
            115                 120                 125

Pro Gly Gln Gln Gly Pro Tyr Gly Ser Ala Ala Ala Ala Gly Pro
            130                 135                 140

Gly Ser Gly Gly Tyr Gly Gln Gly Pro Tyr Gly Pro Gly Ala Ser Ala
145                 150                 155                 160

Ala Ala Ala Gly Pro Gly Gly Tyr Gly Pro Gly Gln Gly Pro
                165                 170                 175

Ser Ala Ser Ala Ala Ala Ala Gly Ser Gly Gln Gln Gly Pro Gly
            180                 185                 190

Gly Tyr Gly Pro Tyr Ala Ser Ala Ala Ala Ala Gly Gly Tyr Gly
            195                 200                 205

Ser Gly Pro Gly Gln Gln Gly Pro Tyr Gly Pro Gly Gly Ser Ala Ala
            210                 215                 220

Ala Ala Ala Gly Ser Gly Gln Gln Gly Pro Gly Gln Gln Gly Pro Tyr
225                 230                 235                 240

Ala Ser Ala Ala Ala Ala Gly Pro Gly Gly Gln Gly Pro Tyr Gly
            245                 250                 255

Pro Gly Ser Ser Ala Ala Ala Ala Gly Gly Tyr Gly Tyr Gly Pro
            260                 265                 270

Gly Gly Gln Gly Pro Tyr Gly Pro Gly Ala Ser Ala Ala Ala Ala
            275                 280                 285

Gly Gly Asn Gly Pro Gly Ser Gly Tyr Gly Pro Gly Gln Gln Gly
            290                 295                 300

Pro Gly Gly Ser Ala Ala Ala Ala Gly Pro Gly Gly Gln Gly Pro
305                 310                 315                 320

Tyr Gly Pro Gly Ala Ser Ala Ala Ala Ala Gly Gly Tyr Gly Pro
            325                 330                 335

Gly Gly Gln Gly Pro Gly Gly Tyr Gly Pro Gly Ser Ser Ala Ala
            340                 345                 350

Ala Ala Gly Pro Gly Gly Gln Gly Pro Tyr Gly Pro Gly Ser Ser Ala
            355                 360                 365

```
Ala Ala Ala Ala Gly Gly Tyr Gly Pro Gly Gln Gln Gly Pro Tyr Gly
        370                 375                 380

Pro Gly Gly Ser Ala Ala Ala Ala Gly Gly Tyr Gln Gln Gly Pro
385                 390                 395                 400

Gly Gly Gln Gly Pro Tyr Gly Pro Gly Ala Ser Ala Ala Ala Ala
                405                 410                 415

Gly Pro Gly Gly Gln Gly Pro Tyr Gly Pro Gly Ala Ser Ala Ala
                420                 425                 430

Ala Ala Gly Pro Gly Gly Tyr Gly Pro Gly Gly Gln Gly Pro Ser Ala
            435                 440                 445

Ser Ala Ala Ala Ala Gly Gly Tyr Gly Ser Gly Pro Gly Gly Tyr
        450                 455                 460

Gly Pro Tyr Gly Pro Gly Ser Ala Ala Ala Ala Gly Pro Gly
465                 470                 475                 480

Ser Gly Gln Gln Gly Gln Gly Pro Tyr Gly Pro Gly Ala Ser Ala Ala
                485                 490                 495

Ala Ala Ala Gly Gly Tyr Gly Pro Gly Gln Gln Gly Pro Tyr Gly Pro
                500                 505                 510

Gly Gly Ser Ala Ala Ala Ala Gly Pro Gly Ser Gly Gly Tyr Gly
        515                 520                 525

Pro Gly Ala Ser Ala Ala Ala Ala Gly Gly Asn Gly Pro Gly Ser
        530                 535                 540

Gly Gly Tyr Gly Pro Gly Gln Gln Pro Gly Gly Ser Ala Ala Ala
545                 550                 555                 560

Ala Ala Gly Gly Tyr Gln Gln Gly Pro Gly Gln Gly Pro Tyr Gly
            565                 570                 575

Pro Gly Ala Ser Ala Ala Ala Ala Gly Pro Gly Ser Gly Gln Gln
        580                 585                 590

Gly Pro Gly Ala Ser
        595

<210> SEQ ID NO 11
<211> LENGTH: 12
<212> TYPE: PRT
<213> ORGANISM: Artificial Sequence
<220> FEATURE:
<223> OTHER INFORMATION: HisTag

<400> SEQUENCE: 11

Met His His His His His His Ser Ser Gly Ser Ser
1               5                   10

<210> SEQ ID NO 12
<211> LENGTH: 608
<212> TYPE: PRT
<213> ORGANISM: Artificial Sequence
<220> FEATURE:
<223> OTHER INFORMATION: PRT380

<400> SEQUENCE: 12

Met His His His His His His Ser Ser Gly Ser Ser Gly Pro Gly Gln
1               5                   10                  15

Gln Gly Pro Tyr Gly Pro Gly Ala Ser Ala Ala Ala Ala Gly Gln
                20                  25                  30

Asn Gly Pro Gly Ser Gly Gln Gln Gly Pro Gly Gln Ser Ala Ala Ala
            35                  40                  45

Ala Ala Gly Gln Tyr Gly Pro Gly Gln Gln Gly Pro Gly Gln Gln Gly
```

-continued

```
                50                  55                  60
Pro Gly Ser Ser Ala Ala Ala Ala Gly Pro Gly Gln Tyr Gly Pro
65                  70                  75                  80

Gly Gln Gln Gly Pro Ser Ala Ser Ala Ala Ala Ala Gly Pro Gly
                85                  90                  95

Ser Gly Gln Gln Gly Pro Gly Ala Ser Ala Ala Ala Ala Gly Gln
                100                 105                 110

Tyr Gly Pro Gly Gln Gln Gly Pro Gln Gln Gly Pro Gly Ser Ser
                115                 120                 125

Ala Ala Ala Ala Ala Gly Gln Tyr Gly Ser Gly Pro Gly Gln Gln Gly
            130                 135                 140

Pro Tyr Gly Ser Ala Ala Ala Ala Gly Pro Gly Ser Gly Gln Tyr
145                 150                 155                 160

Gly Gln Gly Pro Tyr Gly Pro Gly Ala Ser Ala Ala Ala Ala Gly
                165                 170                 175

Pro Gly Gln Tyr Gly Pro Gly Gln Gln Gly Pro Ser Ala Ser Ala Ala
                180                 185                 190

Ala Ala Ala Gly Ser Gly Gln Gln Pro Gly Gln Tyr Gly Pro Tyr
            195                 200                 205

Ala Ser Ala Ala Ala Ala Gly Gln Tyr Gly Ser Gly Pro Gly Gln
            210                 215                 220

Gln Gly Pro Tyr Gly Pro Gly Gln Ser Ala Ala Ala Ala Gly Ser
225                 230                 235                 240

Gly Gln Gln Gly Pro Gly Gln Gly Pro Tyr Ala Ser Ala Ala Ala
                245                 250                 255

Ala Ala Gly Pro Gly Gln Gln Gly Pro Tyr Gly Pro Gly Ser Ser Ala
                260                 265                 270

Ala Ala Ala Ala Gly Gln Tyr Gly Tyr Gly Pro Gly Gln Gln Gly Pro
            275                 280                 285

Tyr Gly Pro Gly Ala Ser Ala Ala Ala Ala Gly Gln Asn Gly Pro
290                 295                 300

Gly Ser Gly Gln Tyr Gly Pro Gly Gln Gln Gly Pro Gly Gln Ser Ala
305                 310                 315                 320

Ala Ala Ala Gly Pro Gly Gln Gln Gly Pro Tyr Gly Pro Gly Ala
                325                 330                 335

Ser Ala Ala Ala Ala Gly Gln Tyr Gly Pro Gly Gln Gln Gly Pro
                340                 345                 350

Gly Gln Tyr Gly Pro Gly Ser Ser Ala Ala Ala Ala Gly Pro Gly
                355                 360                 365

Gln Gln Gly Pro Tyr Gly Pro Gly Ser Ser Ala Ala Ala Ala Gly
370                 375                 380

Gln Tyr Gly Pro Gly Gln Gln Gly Pro Tyr Pro Gly Gln Ser Ala
385                 390                 395                 400

Ala Ala Ala Gly Gln Tyr Gln Gln Gly Pro Gly Gln Gln Gly Pro
                405                 410                 415

Tyr Gly Pro Gly Ala Ser Ala Ala Ala Ala Gly Pro Gly Gln Gln
                420                 425                 430

Gly Pro Tyr Gly Pro Gly Ala Ser Ala Ala Ala Ala Gly Pro Gly
                435                 440                 445

Gln Tyr Gly Pro Gly Gln Gln Gly Pro Ser Ala Ser Ala Ala Ala
                450                 455                 460

Ala Gly Gln Tyr Gly Ser Gly Pro Gly Gln Tyr Gly Pro Tyr Gly Pro
465                 470                 475                 480
```

Gly Gln Ser Ala Ala Ala Ala Gly Pro Gly Ser Gly Gln Gln Gly
                485                 490                 495

Gln Gly Pro Tyr Gly Pro Gly Ala Ser Ala Ala Ala Ala Gly Gln
            500                 505                 510

Tyr Gly Pro Gly Gln Gln Gly Pro Tyr Gly Pro Gly Gln Ser Ala Ala
            515                 520                 525

Ala Ala Ala Gly Pro Gly Ser Gly Gln Tyr Gly Pro Gly Ala Ser Ala
    530                 535                 540

Ala Ala Ala Ala Gly Gln Asn Gly Pro Gly Ser Gly Gln Tyr Gly Pro
545                 550                 555                 560

Gly Gln Gln Gly Pro Gly Gln Ser Ala Ala Ala Ala Gly Gln Tyr
                565                 570                 575

Gln Gln Gly Pro Gly Gln Gln Gly Pro Tyr Gly Pro Gly Ala Ser Ala
            580                 585                 590

Ala Ala Ala Ala Gly Pro Gly Ser Gly Gln Gln Gly Pro Gly Ala Ser
            595                 600                 605

<210> SEQ ID NO 13
<211> LENGTH: 601
<212> TYPE: PRT
<213> ORGANISM: Artificial Sequence
<220> FEATURE:
<223> OTHER INFORMATION: PRT410

<400> SEQUENCE: 13

Met His His His His His Ser Ser Gly Ser Ser Gly Pro Gly Gln
1               5                   10                  15

Gln Gly Pro Tyr Gly Pro Gly Ala Ser Ala Ala Ala Ala Gly Gln
            20                  25                  30

Asn Gly Pro Gly Ser Gly Gln Gln Gly Pro Gly Gln Ser Gly Gln Tyr
            35                  40                  45

Gly Pro Gly Gln Gln Gly Pro Gln Gln Gly Pro Gly Ser Ser Ala
    50                  55                  60

Ala Ala Ala Ala Gly Pro Gly Gln Tyr Gly Pro Gly Gln Gln Gly Pro
65                  70                  75                  80

Ser Ala Ser Ala Ala Ala Ala Gly Pro Gly Ser Gly Gln Gln Gly
                85                  90                  95

Pro Gly Ala Ser Gly Gln Tyr Gly Pro Gly Gln Gln Gly Pro Gly Gln
            100                 105                 110

Gln Gly Pro Gly Ser Ser Ala Ala Ala Ala Gly Gln Tyr Gly Ser
            115                 120                 125

Gly Pro Gly Gln Gln Gly Pro Tyr Gly Ser Ala Ala Ala Ala Gly
    130                 135                 140

Pro Gly Ser Gly Gln Tyr Gly Gln Gly Pro Tyr Gly Pro Gly Ala Ser
145                 150                 155                 160

Gly Pro Gly Gln Tyr Gly Pro Gly Gln Gln Gly Pro Ser Ala Ser Ala
            165                 170                 175

Ala Ala Ala Gly Ser Gly Gln Gln Gly Pro Gly Gln Tyr Gly Pro
            180                 185                 190

Tyr Ala Ser Ala Ala Ala Ala Gly Gln Tyr Gly Ser Gly Pro Gly
            195                 200                 205

Gln Gln Gly Pro Tyr Gly Pro Gly Ser Gly Ser Gly Gln Gln Gly
            210                 215                 220

Pro Gly Gln Gln Gly Pro Tyr Ala Ser Ala Ala Ala Ala Gly Pro
225                 230                 235                 240

Gly Gln Gln Gly Pro Tyr Gly Pro Gly Ser Ser Ala Ala Ala Ala
                245                 250                 255

Gly Gln Tyr Gly Tyr Gly Pro Gly Gln Gly Pro Tyr Gly Pro Gly
            260                 265                 270

Ala Ser Gly Gln Asn Gly Pro Gly Ser Gly Gln Tyr Gly Pro Gly Gln
            275                 280                 285

Gln Gly Pro Gly Gln Ser Ala Ala Ala Ala Gly Pro Gly Gln Gln
        290                 295                 300

Gly Pro Tyr Gly Pro Gly Ala Ser Ala Ala Ala Ala Gly Gln Tyr
305                 310                 315                 320

Gly Pro Gly Gln Gln Gly Pro Gly Gln Tyr Gly Pro Gly Ser Ser Gly
            325                 330                 335

Pro Gly Gln Gln Gly Pro Tyr Gly Pro Gly Ser Ser Ala Ala Ala
            340                 345                 350

Ala Gly Gln Tyr Gly Pro Gly Gln Gln Gly Pro Tyr Gly Pro Gly Gln
            355                 360                 365

Ser Ala Ala Ala Ala Gly Gln Tyr Gln Gln Gly Pro Gly Gln Gln
            370                 375                 380

Gly Pro Tyr Gly Pro Gly Ala Ser Gly Pro Gly Gln Gln Gly Pro Tyr
385                 390                 395                 400

Gly Pro Gly Ala Ser Ala Ala Ala Ala Gly Pro Gly Gln Tyr Gly
            405                 410                 415

Pro Gly Gln Gln Gly Pro Ser Ala Ser Ala Ala Ala Ala Gly Gln
            420                 425                 430

Tyr Gly Ser Gly Pro Gly Gln Tyr Gly Pro Tyr Gly Pro Gly Gln Ser
            435                 440                 445

Gly Pro Gly Ser Gly Gln Gln Gly Gln Gly Pro Tyr Gly Pro Gly Ala
            450                 455                 460

Ser Ala Ala Ala Ala Gly Gln Tyr Gly Pro Gly Gln Gln Gly Pro
465                 470                 475                 480

Tyr Gly Pro Gly Gln Ser Ala Ala Ala Ala Gly Pro Gly Ser Gly
            485                 490                 495

Gln Tyr Gly Pro Gly Ala Ser Gly Gln Asn Gly Pro Gly Ser Gly Gln
            500                 505                 510

Tyr Gly Pro Gly Gln Gln Gly Pro Gly Gln Ser Ala Ala Ala Ala
            515                 520                 525

Gly Gln Tyr Gln Gln Gly Pro Gly Gln Gln Gly Pro Tyr Gly Pro Gly
            530                 535                 540

Ala Ser Ala Ala Ala Ala Gly Gln Tyr Gly Ser Gly Pro Gly Gln
545                 550                 555                 560

Gln Gly Pro Tyr Gly Pro Gly Gln Ser Gly Ser Gly Gln Gln Gly Pro
            565                 570                 575

Gly Gln Gln Gly Pro Tyr Ala Ser Ala Ala Ala Ala Gly Pro Gly
            580                 585                 590

Ser Gly Gln Gln Gly Pro Gly Ala Ser
            595                 600

<210> SEQ ID NO 14
<211> LENGTH: 576
<212> TYPE: PRT
<213> ORGANISM: Artificial Sequence
<220> FEATURE:
<223> OTHER INFORMATION: PRT468

<400> SEQUENCE: 14

```
Met His His His His His Ser Ser Gly Ser Ser Gly Pro Gly Gln
1               5                   10                  15

Gln Gly Pro Tyr Gly Pro Gly Ala Ser Ala Ala Ala Ala Ala Ala
                20                  25                  30

Gly Ser Asn Gly Pro Gly Ser Gly Gln Gln Gly Pro Gly Gln Ser Gly
        35                  40                  45

Gln Tyr Gly Pro Gly Gln Gln Gly Pro Gly Gln Gln Gly Pro Gly Ser
    50                  55                  60

Ser Ala Ala Ala Ala Ala Ala Gly Pro Gly Gln Tyr Gly Pro Gly
65                  70                  75                  80

Gln Gln Gly Pro Ser Ala Ser Ala Ala Ala Ala Ala Ala Gly Pro
                85                  90                  95

Gly Ser Gly Gln Gln Gly Pro Gly Ala Ser Gly Gln Tyr Gly Pro Gly
        100                 105                 110

Gln Gln Gly Pro Gly Gln Gln Gly Pro Gly Ser Ser Ala Ala Ala Ala
        115                 120                 125

Ala Ala Ala Gly Ser Tyr Gly Ser Gly Pro Gly Gln Gln Gly Pro Tyr
    130                 135                 140

Gly Ser Ala Ala Ala Ala Ala Ala Gly Pro Gly Ser Gly Gln Tyr
145                 150                 155                 160

Gly Gln Gly Pro Tyr Gly Pro Gly Ala Ser Gly Pro Gly Gln Tyr Gly
                165                 170                 175

Pro Gly Gln Gln Gly Pro Ser Ala Ser Ala Ala Ala Ala Ala Ala
            180                 185                 190

Gly Ser Gly Gln Gln Gly Pro Gly Gln Tyr Gly Pro Tyr Ala Ser Ala
        195                 200                 205

Ala Ala Ala Ala Ala Gly Ser Tyr Gly Ser Gly Pro Gly Gln Gln
    210                 215                 220

Gly Pro Tyr Gly Pro Gly Gln Ser Gly Ser Gly Gln Gln Gly Pro Gly
225                 230                 235                 240

Gln Gln Gly Pro Tyr Ala Ser Ala Ala Ala Ala Ala Ala Gly Pro
                245                 250                 255

Gly Gln Gln Gly Pro Tyr Gly Pro Gly Ser Ser Ala Ala Ala Ala
        260                 265                 270

Ala Ala Gly Ser Tyr Gly Tyr Gly Pro Gly Gln Gln Gly Pro Tyr Gly
    275                 280                 285

Pro Gly Ala Ser Gly Gln Asn Gly Pro Gly Ser Gly Gln Tyr Gly Pro
    290                 295                 300

Gly Gln Gln Gly Pro Gly Pro Ser Ala Ala Ala Ala Ala Ala Gly
305                 310                 315                 320

Pro Gly Gln Gln Gly Pro Tyr Gly Pro Gly Ala Ser Ala Ala Ala
                325                 330                 335

Ala Ala Ala Gly Ser Tyr Gly Pro Gly Gln Gln Gly Pro Gly Gln Tyr
        340                 345                 350

Gly Pro Gly Ser Ser Gly Pro Gly Gln Gln Gly Pro Tyr Gly Pro Gly
    355                 360                 365

Ser Ser Ala Ala Ala Ala Ala Ala Gly Ser Tyr Gly Pro Gly Gln
    370                 375                 380

Gln Gly Pro Tyr Gly Pro Gly Pro Ser Ala Ala Ala Ala Ala Ala
385                 390                 395                 400

Gly Ser Tyr Gln Gln Gly Pro Gly Gln Gln Gly Pro Tyr Gly Pro Gly
        405                 410                 415
```

```
Ala Ser Gly Pro Gly Gln Gln Gly Pro Tyr Gly Pro Gly Ala Ser Ala
            420                 425                 430

Ala Ala Ala Ala Ala Ala Gly Pro Gly Gln Tyr Gly Pro Gly Gln Gln
                435                 440                 445

Gly Pro Ser Ala Ser Ala Ala Ala Ala Ala Gly Ser Tyr Gly
    450                 455                 460

Ser Gly Pro Gly Gln Tyr Gly Pro Tyr Gly Pro Gly Gln Ser Gly Pro
465                 470                 475                 480

Gly Ser Gly Gln Gln Gly Gln Gly Pro Tyr Gly Pro Gly Ala Ser Ala
                485                 490                 495

Ala Ala Ala Ala Ala Gly Ser Tyr Gly Pro Gly Gln Gln Gly Pro
            500                 505                 510

Tyr Gly Pro Gly Pro Ser Ala Ala Ala Ala Ala Gly Pro Gly
    515                 520                 525

Ser Gly Gln Tyr Gly Pro Gly Ala Ser Gly Gln Asn Gly Pro Gly Ser
    530                 535                 540

Gly Gln Tyr Gly Pro Gly Gln Gln Gly Pro Gly Pro Ser Ala Ala Ala
545                 550                 555                 560

Ala Ala Ala Ala Gly Pro Gly Ser Gly Gln Gln Gly Pro Gly Ala Ser
                565                 570                 575
```

<210> SEQ ID NO 15
<211> LENGTH: 2375
<212> TYPE: PRT
<213> ORGANISM: Artificial Sequence
<220> FEATURE:
<223> OTHER INFORMATION: PRT799

<400> SEQUENCE: 15

```
Met His His His His His Ser Ser Gly Ser Ser Gly Pro Gly Gln
1               5                   10                  15

Gln Gly Pro Tyr Gly Pro Gly Ala Ser Ala Ala Ala Ala Gly Gln
            20                  25                  30

Asn Gly Pro Gly Ser Gly Gln Gln Gly Pro Gly Gln Ser Gly Gln Tyr
                35                  40                  45

Gly Pro Gly Gln Gln Gly Pro Gln Gly Pro Gly Ser Ser Ala
    50                  55                  60

Ala Ala Ala Gly Pro Gly Gln Tyr Gly Pro Gly Gln Gln Gly Pro
65                  70                  75                  80

Ser Ala Ser Ala Ala Ala Ala Ala Gly Pro Gly Ser Gly Gln Gln Gly
                85                  90                  95

Pro Gly Ala Ser Gly Gln Tyr Gly Pro Gly Gln Gln Gly Pro Gly Gln
            100                 105                 110

Gln Gly Pro Gly Ser Ser Ala Ala Ala Ala Gly Gln Tyr Gly Ser
                115                 120                 125

Gly Pro Gly Gln Gln Gly Pro Tyr Gly Ser Ala Ala Ala Ala Gly
    130                 135                 140

Pro Gly Ser Gly Gln Tyr Gly Pro Gly Gly Pro Tyr Gly Pro Gly Ala Ser
145                 150                 155                 160

Gly Pro Gly Gln Tyr Gly Pro Gly Gln Gln Gly Pro Ser Ala Ser Ala
                165                 170                 175

Ala Ala Ala Gly Ser Gly Gln Gln Gly Pro Gly Gln Tyr Gly Pro
            180                 185                 190

Tyr Ala Ser Ala Ala Ala Ala Gly Gln Tyr Gly Ser Gly Pro Gly
                195                 200                 205
```

-continued

```
Gln Gln Gly Pro Tyr Gly Pro Gly Gln Ser Gly Ser Gly Gln Gln Gly
    210                 215                 220
Pro Gly Gln Gln Gly Pro Tyr Ala Ser Ala Ala Ala Ala Gly Pro
225                 230                 235                 240
Gly Gln Gln Gly Pro Tyr Gly Pro Gly Ser Ser Ala Ala Ala Ala
            245                 250                 255
Gly Gln Tyr Gly Tyr Gly Pro Gly Gln Gly Pro Tyr Gly Pro Gly
                260                 265                 270
Ala Ser Gly Gln Asn Gly Pro Ser Gly Gln Tyr Gly Pro Gly Gln
        275                 280                 285
Gln Gly Pro Gly Gln Ser Ala Ala Ala Ala Gly Pro Gly Gln Gln
    290                 295                 300
Gly Pro Tyr Gly Pro Gly Ala Ser Ala Ala Ala Ala Gly Gln Tyr
305                 310                 315                 320
Gly Pro Gly Gln Gln Gly Pro Gly Gln Tyr Gly Pro Gly Ser Ser Gly
            325                 330                 335
Pro Gly Gln Gln Gly Pro Tyr Gly Pro Gly Ser Ser Ala Ala Ala
                340                 345                 350
Ala Gly Gln Tyr Gly Pro Gly Gln Gln Gly Pro Tyr Gly Pro Gly Gln
        355                 360                 365
Ser Ala Ala Ala Ala Gly Gln Tyr Gln Gln Gly Pro Gly Gln Gln
    370                 375                 380
Gly Pro Tyr Gly Pro Gly Ala Ser Gly Pro Gly Gln Gln Gly Pro Tyr
385                 390                 395                 400
Gly Pro Gly Ala Ser Ala Ala Ala Ala Gly Pro Gly Gln Tyr Gly
            405                 410                 415
Pro Gly Gln Gln Gly Pro Ser Ala Ser Ala Ala Ala Ala Gly Gln
                420                 425                 430
Tyr Gly Ser Gly Pro Gly Gln Tyr Gly Pro Tyr Gly Pro Gly Gln Ser
        435                 440                 445
Gly Pro Gly Ser Gly Gln Gln Gly Pro Tyr Gly Pro Gly Ala
    450                 455                 460
Ser Ala Ala Ala Ala Gly Gln Tyr Gly Pro Gly Gln Gln Gly Pro
465                 470                 475                 480
Tyr Gly Pro Gly Gln Ser Ala Ala Ala Ala Gly Pro Gly Ser Gly
            485                 490                 495
Gln Tyr Gly Pro Gly Ala Ser Gly Gln Asn Gly Pro Gly Ser Gly Gln
        500                 505                 510
Tyr Gly Pro Gly Gln Gly Pro Gly Gln Ser Ala Ala Ala Ala
    515                 520                 525
Gly Gln Tyr Gln Gln Gly Pro Gly Gln Gln Gly Pro Tyr Gly Pro Gly
530                 535                 540
Ala Ser Ala Ala Ala Ala Gly Gln Tyr Gly Ser Gly Pro Gly Gln
545                 550                 555                 560
Gln Gly Pro Tyr Gly Pro Gly Gln Ser Gly Ser Gly Gln Gln Gly Pro
            565                 570                 575
Gly Gln Gln Gly Pro Tyr Ala Ser Ala Ala Ala Ala Gly Pro Gly
                580                 585                 590
Ser Gly Gln Gly Pro Gly Ala Ser Gly Gln Gln Gly Pro Tyr Gly
        595                 600                 605
Pro Gly Ala Ser Ala Ala Ala Ala Gly Gln Asn Gly Pro Gly Ser
    610                 615                 620
Gly Gln Gln Gly Pro Gly Gln Ser Gly Gln Tyr Gly Pro Gly Gln Gln
```

```
            625                 630                 635                 640
Gly Pro Gly Gln Gln Gly Pro Gly Ser Ser Ala Ala Ala Ala Ala Gly
                    645                 650                 655
Pro Gly Gln Tyr Gly Pro Gly Gln Gln Gly Pro Ser Ala Ser Ala Ala
                    660                 665                 670
Ala Ala Ala Gly Pro Gly Ser Gly Gln Gln Gly Pro Gly Ala Ser Gly
                    675                 680                 685
Gln Tyr Gly Pro Gly Gln Gly Pro Gly Gln Gln Gly Pro Gly Ser
    690                 695                 700
Ser Ala Ala Ala Ala Gly Gln Tyr Gly Ser Gly Pro Gly Gln Gln
705                 710                 715                 720
Gly Pro Tyr Gly Ser Ala Ala Ala Ala Gly Pro Gly Ser Gly Gln
                    725                 730                 735
Tyr Gly Gln Gly Pro Tyr Gly Pro Gly Ala Ser Gly Pro Gly Gln Tyr
                    740                 745                 750
Gly Pro Gly Gln Gln Gly Pro Ser Ala Ser Ala Ala Ala Ala Gly
                    755                 760                 765
Ser Gly Gln Gln Gly Pro Gly Gln Tyr Gly Pro Tyr Ala Ser Ala Ala
    770                 775                 780
Ala Ala Ala Gly Gln Tyr Gly Ser Gly Pro Gly Gln Gln Gly Pro Tyr
785                 790                 795                 800
Gly Pro Gly Gln Ser Gly Ser Gly Gln Gln Gly Pro Gly Gln Gln Gly
                    805                 810                 815
Pro Tyr Ala Ser Ala Ala Ala Ala Gly Pro Gly Gln Gln Gly Pro
            820                 825                 830
Tyr Gly Pro Gly Ser Ser Ala Ala Ala Gly Gln Tyr Gly Tyr
            835                 840                 845
Gly Pro Gly Gln Gln Gly Pro Tyr Gly Pro Gly Ala Ser Gly Gln Asn
    850                 855                 860
Gly Pro Gly Ser Gly Gln Tyr Gly Pro Gly Gln Gln Gly Pro Gly Gln
865                 870                 875                 880
Ser Ala Ala Ala Ala Ala Gly Pro Gly Gln Gln Gly Pro Tyr Gly Pro
            885                 890                 895
Gly Ala Ser Ala Ala Ala Ala Gly Gln Tyr Gly Pro Gly Gln Gln
            900                 905                 910
Gly Pro Gly Gln Tyr Gly Pro Gly Ser Ser Gly Pro Gly Gln Gln Gly
    915                 920                 925
Pro Tyr Gly Pro Gly Ser Ser Ala Ala Ala Ala Gly Gln Tyr Gly
    930                 935                 940
Pro Gly Gln Gln Gly Pro Tyr Gly Pro Gly Gln Ser Ala Ala Ala
945                 950                 955                 960
Ala Gly Gln Tyr Gln Gln Gly Pro Gly Gln Gly Pro Tyr Gly Pro
            965                 970                 975
Gly Ala Ser Gly Pro Gly Gln Gln Gly Pro Tyr Gly Pro Gly Ala Ser
            980                 985                 990
Ala Ala Ala Ala Ala Gly Pro Gly Gln Tyr Gly Pro Gly Gln Gln Gly
        995                 1000                1005
Pro Ser Ala Ser Ala Ala Ala Ala Gly Gln Tyr Gly Ser Gly
    1010                1015                1020
Pro Gly Gln Tyr Gly Pro Tyr Gly Pro Gly Gln Ser Gly Pro Gly
    1025                1030                1035
Ser Gly Gln Gln Gly Gln Gly Pro Tyr Gly Pro Gly Ala Ser Ala
    1040                1045                1050
```

```
Ala Ala  Ala Ala Gly Gln Tyr  Gly Pro Gly Gln Gln  Gly Pro Tyr
    1055             1060              1065

Gly Pro  Gly Gln Ser Ala Ala  Ala Ala Gly Pro Gly  Ser Gly
    1070             1075              1080

Gln Tyr  Gly Pro Gly Ala Ser  Gly Gln Asn Gly Pro  Gly Ser Gly
    1085             1090              1095

Gln Tyr  Gly Pro Gly Gln Gln  Gly Pro Gly Gln Ser  Ala Ala Ala
    1100             1105              1110

Ala Ala  Gly Gln Tyr Gln Gln  Gly Pro Gly Gln Gln  Gly Pro Tyr
    1115             1120              1125

Gly Pro  Gly Ala Ser Ala Ala  Ala Ala Gly Gln Tyr  Gly Ser
    1130             1135              1140

Gly Pro  Gly Gln Gln Gly Pro  Tyr Gly Pro Gly Gln  Ser Gly Ser
    1145             1150              1155

Gly Gln  Gln Gly Pro Gly Gln  Gln Gly Pro Tyr Ala  Ser Ala Ala
    1160             1165              1170

Ala Ala  Ala Gly Pro Gly Ser  Gly Gln Gln Gly Pro  Gly Ala Ser
    1175             1180              1185

Gly Gln  Gln Gly Pro Tyr Gly  Pro Gly Ala Ser Ala  Ala Ala Ala
    1190             1195              1200

Ala Gly  Gln Asn Gly Pro Gly  Ser Gly Gln Gln Gly  Pro Gly Gln
    1205             1210              1215

Ser Gly  Gln Tyr Gly Pro Gly  Gln Gln Gly Pro Gly  Gln Gln Gly
    1220             1225              1230

Pro Gly  Ser Ser Ala Ala Ala  Ala Ala Gly Pro Gly  Gln Tyr Gly
    1235             1240              1245

Pro Gly  Gln Gln Gly Pro Ser  Ala Ser Ala Ala Ala  Ala Ala Gly
    1250             1255              1260

Pro Gly  Ser Gly Gln Gln Gly  Pro Gly Ala Ser Gly  Gln Tyr Gly
    1265             1270              1275

Pro Gly  Gln Gln Pro Gly Gln  Gln Gly Pro Gly Gly  Ser Ser Ala
    1280             1285              1290

Ala Ala  Ala Ala Gly Gln Tyr  Gly Ser Gly Pro Gly  Gln Gln Gly
    1295             1300              1305

Pro Tyr  Gly Ser Ala Ala Ala  Ala Ala Gly Pro Gly  Ser Gly Gln
    1310             1315              1320

Tyr Gly  Gln Gly Pro Tyr Gly  Pro Gly Ala Ser Gly  Pro Gly Gln
    1325             1330              1335

Tyr Gly  Pro Gly Gln Gln Gly  Pro Ser Ala Ser Ala  Ala Ala Ala
    1340             1345              1350

Ala Gly  Ser Gly Gln Gln Gly  Pro Gly Gln Tyr Gly  Pro Tyr Ala
    1355             1360              1365

Ser Ala  Ala Ala Ala Ala Gly  Gln Tyr Gly Ser Gly  Pro Gly Gln
    1370             1375              1380

Gln Gly  Pro Tyr Gly Pro Gly  Gln Ser Gly Ser Gly  Gln Gln Gly
    1385             1390              1395

Pro Gly  Gln Gln Gly Pro Tyr  Ala Ser Ala Ala Ala  Ala Ala Gly
    1400             1405              1410

Pro Gly  Gln Gln Gly Pro Tyr  Gly Pro Gly Ser Ser  Ala Ala Ala
    1415             1420              1425

Ala Ala  Gly Gln Tyr Gly Tyr  Gly Pro Gly Gln Gln  Gly Pro Tyr
    1430             1435              1440
```

| | | | | | | | | | | | |
|---|---|---|---|---|---|---|---|---|---|---|---|
|Gly|Pro|Gly|Ala|Ser|Gly|Gln|Asn|Gly|Pro|Gly|Ser|Gly|Gln|Tyr|
| |1445| | | |1450| | | |1455| | |

Gly Pro Gly Gln Gln Gly Pro Gly Gln Ser Ala Ala Ala Ala Ala
   1460              1465              1470

Gly Pro Gly Gln Gln Gly Pro Tyr Gly Pro Gly Ala Ser Ala Ala
   1475              1480              1485

Ala Ala Ala Gly Gln Tyr Gly Pro Gly Gln Gln Gly Pro Gly Gln
   1490              1495              1500

Tyr Gly Pro Gly Ser Ser Gly Pro Gly Gln Gln Gly Pro Tyr Gly
   1505              1510              1515

Pro Gly Ser Ser Ala Ala Ala Ala Gly Gln Tyr Gly Pro Gly
   1520              1525              1530

Gln Gln Gly Pro Tyr Gly Pro Gly Gln Ser Ala Ala Ala Ala Ala
   1535              1540              1545

Gly Gln Tyr Gln Gln Gly Pro Gly Gln Gly Pro Tyr Gly Pro
   1550              1555              1560

Gly Ala Ser Gly Pro Gly Gln Gln Gly Pro Tyr Gly Pro Gly Ala
   1565              1570              1575

Ser Ala Ala Ala Ala Ala Gly Pro Gly Gln Tyr Gly Pro Gly Gln
   1580              1585              1590

Gln Gly Pro Ser Ala Ser Ala Ala Ala Ala Gly Gln Tyr Gly
   1595              1600              1605

Ser Gly Pro Gly Gln Tyr Gly Pro Tyr Gly Pro Gly Gln Ser Gly
   1610              1615              1620

Pro Gly Ser Gly Gln Gln Gly Gln Gly Pro Tyr Gly Pro Gly Ala
   1625              1630              1635

Ser Ala Ala Ala Ala Gly Gln Tyr Gly Pro Gly Gln Gln Gly
   1640              1645              1650

Pro Tyr Gly Pro Gly Gln Ser Ala Ala Ala Ala Gly Pro Gly
   1655              1660              1665

Ser Gly Gln Tyr Gly Pro Gly Ala Ser Gly Gln Asn Gly Pro Gly
   1670              1675              1680

Ser Gly Gln Tyr Gly Pro Gly Gln Gln Gly Pro Gly Gln Ser Ala
   1685              1690              1695

Ala Ala Ala Gly Gln Tyr Gln Gln Gly Pro Gly Gln Gln Gly
   1700              1705              1710

Pro Tyr Gly Pro Gly Ala Ser Ala Ala Ala Ala Gly Gln Tyr
   1715              1720              1725

Gly Ser Gly Pro Gly Gln Gln Gly Pro Tyr Gly Pro Gly Gln Ser
   1730              1735              1740

Gly Ser Gly Gln Gln Gly Pro Gly Gln Gln Gly Pro Tyr Ala Ser
   1745              1750              1755

Ala Ala Ala Ala Ala Gly Pro Gly Ser Gly Gln Gln Gly Pro Gly
   1760              1765              1770

Ala Ser Gly Gln Gln Gly Pro Tyr Gly Pro Gly Ala Ser Ala Ala
   1775              1780              1785

Ala Ala Ala Gly Gln Asn Gly Pro Gly Ser Gly Gln Gln Gly Pro
   1790              1795              1800

Gly Gln Ser Gly Gln Tyr Gly Pro Gly Gln Gln Gly Pro Gly Gln
   1805              1810              1815

Gln Gly Pro Gly Ser Ser Ala Ala Ala Ala Gly Pro Gly Gln
   1820              1825              1830

Tyr Gly Pro Gly Gln Gln Gly Pro Ser Ala Ser Ala Ala Ala Ala

```
              1835                1840                1845

Ala Gly Pro Gly Ser Gly Gln Gln Gly Pro Gly Ala Ser Gly Gln
              1850                1855                1860

Tyr Gly Pro Gly Gln Gln Gly Pro Gly Gln Gln Gly Pro Gly Ser
              1865                1870                1875

Ser Ala Ala Ala Ala Ala Gly Gln Tyr Gly Ser Gly Pro Gly Gln
              1880                1885                1890

Gln Gly Pro Tyr Gly Ser Ala Ala Ala Ala Gly Pro Gly Ser
              1895                1900                1905

Gly Gln Tyr Gly Gln Gly Pro Tyr Gly Pro Gly Ala Ser Gly Pro
              1910                1915                1920

Gly Gln Tyr Gly Pro Gly Gln Gln Gly Pro Ser Ala Ser Ala Ala
              1925                1930                1935

Ala Ala Ala Gly Ser Gly Gln Gln Gly Pro Gly Gln Tyr Gly Pro
              1940                1945                1950

Tyr Ala Ser Ala Ala Ala Ala Gly Gln Tyr Gly Ser Gly Pro
              1955                1960                1965

Gly Gln Gln Gly Pro Tyr Gly Pro Gly Gln Ser Gly Ser Gly Gln
              1970                1975                1980

Gln Gly Pro Gly Gln Gln Gly Pro Tyr Ala Ser Ala Ala Ala Ala
              1985                1990                1995

Ala Gly Pro Gly Gln Gln Gly Pro Tyr Gly Pro Gly Ser Ser Ala
              2000                2005                2010

Ala Ala Ala Gly Gln Tyr Gly Tyr Gly Pro Gly Gln Gln Gly
              2015                2020                2025

Pro Tyr Gly Pro Gly Ala Ser Gly Gln Asn Gly Pro Gly Ser Gly
              2030                2035                2040

Gln Tyr Gly Pro Gly Gln Gln Gly Pro Gly Gln Ser Ala Ala Ala
              2045                2050                2055

Ala Ala Gly Pro Gly Gln Gln Gly Pro Tyr Gly Pro Gly Ala Ser
              2060                2065                2070

Ala Ala Ala Ala Gly Gln Tyr Gly Pro Gly Gln Gln Gly Pro
              2075                2080                2085

Gly Gln Tyr Gly Pro Gly Ser Ser Gly Pro Gly Gln Gln Gly Pro
              2090                2095                2100

Tyr Gly Pro Gly Ser Ser Ala Ala Ala Ala Gly Gln Tyr Gly
              2105                2110                2115

Pro Gly Gln Gln Gly Pro Tyr Gly Pro Gly Gln Ser Ala Ala Ala
              2120                2125                2130

Ala Ala Gly Gln Tyr Gln Gln Gly Pro Gly Gln Gln Gly Pro Tyr
              2135                2140                2145

Gly Pro Gly Ala Ser Gly Pro Gly Gln Gln Gly Pro Tyr Gly Pro
              2150                2155                2160

Gly Ala Ser Ala Ala Ala Ala Ala Gly Pro Gly Gln Tyr Gly Pro
              2165                2170                2175

Gly Gln Gln Gly Pro Ser Ala Ser Ala Ala Ala Ala Ala Gly Gln
              2180                2185                2190

Tyr Gly Ser Gly Pro Gly Gln Tyr Gly Tyr Gly Pro Gly Gln
              2195                2200                2205

Ser Gly Pro Gly Ser Gly Gln Gly Gln Gly Pro Tyr Gly Pro
              2210                2215                2220

Gly Ala Ser Ala Ala Ala Ala Ala Gly Gln Tyr Gly Pro Gly Gln
              2225                2230                2235
```

Gln Gly Pro Tyr Gly Pro Gly Gln Ser Ala Ala Ala Ala Gly
    2240                2245                2250

Pro Gly Ser Gly Gln Tyr Gly Pro Gly Ala Ser Gly Gln Asn Gly
    2255                2260                2265

Pro Gly Ser Gly Gln Tyr Gly Pro Gly Gln Gln Gly Pro Gly Gln
    2270                2275                2280

Ser Ala Ala Ala Ala Gly Gln Tyr Gln Gln Gly Pro Gly Gln
    2285                2290                2295

Gln Gly Pro Tyr Gly Pro Gly Ala Ser Ala Ala Ala Ala Gly
    2300                2305                2310

Gln Tyr Gly Ser Gly Pro Gly Gln Gln Gly Pro Tyr Gly Pro Gly
    2315                2320                2325

Gln Ser Gly Ser Gly Gln Gln Gly Pro Gly Gln Gln Gly Pro Tyr
    2330                2335                2340

Ala Ser Ala Ala Ala Ala Gly Pro Gly Ser Gly Gln Gln Gly
    2345                2350                2355

Ser Ser Val Asp Lys Leu Ala Ala Ala Leu Glu His His His His
    2360                2365                2370

His His
    2375

<210> SEQ ID NO 16
<211> LENGTH: 608
<212> TYPE: PRT
<213> ORGANISM: Artificial Sequence
<220> FEATURE:
<223> OTHER INFORMATION: PRT313

<400> SEQUENCE: 16

Met His His His His His Ser Ser Gly Ser Gly Pro Gly Gly
1               5                   10                  15

Gln Gly Pro Tyr Gly Pro Gly Ala Ser Ala Ala Ala Ala Gly Gly
                20                  25                  30

Asn Gly Pro Gly Ser Gly Gln Gln Gly Pro Gly Gly Ser Ala Ala
        35                  40                  45

Ala Ala Gly Gly Tyr Gly Pro Gly Gln Gly Pro Gly Gln Gln Gly
    50                  55                  60

Pro Gly Ser Ser Ala Ala Ala Ala Gly Pro Gly Tyr Gly Pro
65                  70                  75                  80

Gly Gly Gln Gly Pro Ser Ala Ser Ala Ala Ala Ala Gly Pro Gly
                85                  90                  95

Ser Gly Gln Gln Gly Pro Gly Ala Ser Ala Ala Ala Ala Gly Gly
                100                 105                 110

Tyr Gly Pro Gly Gly Gln Gly Pro Gly Gln Gln Gly Pro Gly Ser Ser
        115                 120                 125

Ala Ala Ala Ala Ala Gly Gly Tyr Gly Ser Gly Pro Gly Gln Gln Gly
    130                 135                 140

Pro Tyr Gly Ser Ala Ala Ala Ala Gly Pro Gly Ser Gly Tyr
145                 150                 155                 160

Gly Gln Gly Pro Tyr Gly Pro Gly Ala Ser Ala Ala Ala Ala Gly
                165                 170                 175

Pro Gly Gly Tyr Gly Pro Gly Gln Gly Pro Ser Ala Ser Ala Ala
                180                 185                 190

Ala Ala Ala Gly Ser Gly Gln Gln Gly Pro Gly Gly Tyr Gly Pro Tyr
                195                 200                 205

Ala Ser Ala Ala Ala Ala Gly Gly Tyr Gly Ser Gly Pro Gly Gln
    210                 215                 220

Gln Gly Pro Tyr Gly Pro Gly Gly Ser Ala Ala Ala Ala Gly Ser
225                 230                 235                 240

Gly Gln Gln Gly Pro Gly Gln Gly Pro Tyr Ala Ser Ala Ala Ala
                245                 250                 255

Ala Ala Gly Pro Gly Gly Gln Gly Pro Tyr Gly Pro Gly Ser Ser Ala
            260                 265                 270

Ala Ala Ala Ala Gly Gly Tyr Gly Tyr Gly Pro Gly Gly Gln Gly Pro
        275                 280                 285

Tyr Gly Pro Gly Ala Ser Ala Ala Ala Ala Gly Asn Gly Pro
            290                 295                 300

Gly Ser Gly Gly Tyr Gly Pro Gly Gln Gln Gly Pro Gly Gly Ser Ala
305                 310                 315                 320

Ala Ala Ala Gly Pro Gly Gly Gln Gly Pro Tyr Gly Pro Gly Ala
            325                 330                 335

Ser Ala Ala Ala Ala Gly Gly Tyr Gly Pro Gly Gln Gly Pro
            340                 345                 350

Gly Gly Tyr Gly Pro Gly Ser Ser Ala Ala Ala Ala Gly Pro Gly
            355                 360                 365

Gly Gln Gly Pro Tyr Gly Pro Gly Ser Ser Ala Ala Ala Ala Gly
    370                 375                 380

Gly Tyr Gly Pro Gly Gln Gln Gly Pro Tyr Gly Pro Gly Ser Ala
385                 390                 395                 400

Ala Ala Ala Gly Gly Tyr Gln Gln Gly Pro Gly Gly Gln Gly Pro
            405                 410                 415

Tyr Gly Pro Gly Ala Ser Ala Ala Ala Ala Gly Pro Gly Gly Gln
            420                 425                 430

Gly Pro Tyr Gly Pro Gly Ala Ser Ala Ala Ala Ala Gly Pro Gly
            435                 440                 445

Gly Tyr Gly Pro Gly Gly Gln Gly Pro Ser Ala Ser Ala Ala Ala
    450                 455                 460

Ala Gly Gly Tyr Gly Ser Gly Pro Gly Gly Tyr Gly Pro Tyr Gly Pro
465                 470                 475                 480

Gly Gly Ser Ala Ala Ala Ala Gly Pro Gly Ser Gly Gln Gln Gly
            485                 490                 495

Gln Gly Pro Tyr Gly Pro Gly Ala Ser Ala Ala Ala Ala Gly Gly
            500                 505                 510

Tyr Gly Pro Gly Gln Gln Gly Pro Tyr Gly Pro Gly Gly Ser Ala Ala
        515                 520                 525

Ala Ala Ala Gly Pro Gly Ser Gly Gly Tyr Gly Pro Gly Ala Ser Ala
    530                 535                 540

Ala Ala Ala Gly Gly Asn Gly Pro Gly Ser Gly Gly Tyr Gly Pro
545                 550                 555                 560

Gly Gln Gln Gly Pro Gly Gly Ser Ala Ala Ala Ala Gly Gly Tyr
            565                 570                 575

Gln Gln Gly Pro Gly Gly Gln Gly Pro Tyr Gly Pro Gly Ala Ser Ala
        580                 585                 590

Ala Ala Ala Gly Pro Gly Ser Gly Gln Gln Gly Pro Gly Ala Ser
    595                 600                 605

<210> SEQ ID NO 17
<211> LENGTH: 590

<212> TYPE: PRT
<213> ORGANISM: Artificial Sequence
<220> FEATURE:
<223> OTHER INFORMATION: Met-PRT399

<400> SEQUENCE: 17

```
Met Gly Pro Gly Gly Gln Gly Pro Tyr Gly Pro Gly Ala Ser Ala Ala
1               5                   10                  15

Ala Ala Ala Gly Gly Asn Gly Pro Gly Ser Gly Gln Gln Gly Pro Gly
            20                  25                  30

Gly Ser Gly Gly Tyr Gly Pro Gly Gln Gly Pro Gly Gln Gln Gly
        35                  40                  45

Pro Gly Ser Ser Ala Ala Ala Ala Gly Pro Gly Tyr Gly Pro
    50                  55                  60

Gly Gly Gln Gly Pro Ser Ala Ser Ala Ala Ala Ala Gly Pro Gly
65                  70                  75                  80

Ser Gly Gln Gln Gly Pro Gly Ala Ser Gly Tyr Gly Pro Gly Gly
                85                  90                  95

Gln Gly Pro Gly Gln Gln Gly Pro Gly Ser Ser Ala Ala Ala Ala
            100                 105                 110

Gly Gly Tyr Gly Ser Gly Pro Gly Gln Gln Gly Pro Tyr Gly Ser Ala
            115                 120                 125

Ala Ala Ala Ala Gly Pro Gly Ser Gly Gly Tyr Gly Gln Gly Pro Tyr
130                 135                 140

Gly Pro Gly Ala Ser Gly Pro Gly Gly Tyr Gly Pro Gly Gln Gly
145                 150                 155                 160

Pro Ser Ala Ser Ala Ala Ala Ala Gly Ser Gly Gln Gln Gly Pro
                165                 170                 175

Gly Gly Tyr Gly Pro Tyr Ala Ser Ala Ala Ala Ala Gly Gly Tyr
            180                 185                 190

Gly Ser Gly Pro Gly Gln Gln Gly Pro Tyr Gly Pro Gly Ser Gly
        195                 200                 205

Ser Gly Gln Gln Gly Pro Gly Gln Gln Gly Pro Tyr Ala Ser Ala Ala
210                 215                 220

Ala Ala Ala Gly Pro Gly Gly Gln Gly Pro Tyr Gly Pro Gly Ser Ser
225                 230                 235                 240

Ala Ala Ala Ala Ala Gly Gly Tyr Gly Tyr Gly Pro Gly Gln Gly
            245                 250                 255

Pro Tyr Gly Pro Gly Ala Ser Gly Gly Asn Gly Pro Gly Ser Gly Gly
        260                 265                 270

Tyr Gly Pro Gly Gln Gln Gly Pro Gly Gly Ser Ala Ala Ala Ala Ala
        275                 280                 285

Gly Pro Gly Gly Gln Gly Pro Tyr Gly Pro Gly Ala Ser Ala Ala Ala
        290                 295                 300

Ala Ala Gly Gly Tyr Gly Pro Gly Gly Gln Gly Pro Gly Gly Tyr Gly
305                 310                 315                 320

Pro Gly Ser Ser Gly Pro Gly Gly Gln Gly Pro Tyr Gly Pro Gly Ser
                325                 330                 335

Ser Ala Ala Ala Ala Gly Gly Tyr Gly Pro Gly Gln Gln Gly Pro
            340                 345                 350

Tyr Gly Pro Gly Gly Ser Ala Ala Ala Ala Gly Gly Tyr Gln Gln
        355                 360                 365

Gly Pro Gly Gly Gln Gly Pro Tyr Gly Pro Gly Ala Ser Gly Pro Gly
        370                 375                 380
```

```
Gly Gln Gly Pro Tyr Gly Pro Gly Ala Ser Ala Ala Ala Ala Gly
385                 390                 395                 400

Pro Gly Gly Tyr Gly Pro Gly Gln Gly Pro Ser Ala Ser Ala Ala
            405                 410                 415

Ala Ala Ala Gly Gly Tyr Gly Ser Gly Pro Gly Gly Tyr Gly Pro Tyr
            420                 425                 430

Gly Pro Gly Gly Ser Gly Pro Gly Ser Gly Gln Gln Gly Gln Gly Pro
        435                 440                 445

Tyr Gly Pro Gly Ala Ser Ala Ala Ala Ala Gly Tyr Gly Pro
        450                 455                 460

Gly Gln Gln Gly Pro Tyr Gly Pro Gly Gly Ser Ala Ala Ala Ala
465                 470                 475                 480

Gly Pro Gly Ser Gly Gly Tyr Gly Pro Gly Ala Ser Gly Gly Asn Gly
            485                 490                 495

Pro Gly Ser Gly Gly Tyr Gly Pro Gly Gln Gln Gly Pro Gly Gly Ser
            500                 505                 510

Ala Ala Ala Ala Ala Gly Gly Tyr Gln Gln Gly Pro Gly Gly Gln Gly
            515                 520                 525

Pro Tyr Gly Pro Gly Ala Ser Ala Ala Ala Ala Gly Gly Tyr Gly
        530                 535                 540

Ser Gly Pro Gly Gln Gln Gly Pro Tyr Gly Pro Gly Gly Ser Gly Ser
545                 550                 555                 560

Gly Gln Gln Gly Pro Gly Gln Gly Pro Tyr Ala Ser Ala Ala Ala
            565                 570                 575

Ala Ala Gly Pro Gly Ser Gly Gln Gly Pro Gly Ala Ser
        580                 585                 590

<210> SEQ ID NO 18
<211> LENGTH: 601
<212> TYPE: PRT
<213> ORGANISM: Artificial Sequence
<220> FEATURE:
<223> OTHER INFORMATION: PRT399

<400> SEQUENCE: 18

Met His His His His His Ser Ser Gly Ser Ser Gly Pro Gly Gly
1               5                   10                  15

Gln Gly Pro Tyr Gly Pro Gly Ala Ser Ala Ala Ala Ala Gly Gly
            20                  25                  30

Asn Gly Pro Gly Ser Gly Gln Gln Gly Pro Gly Gly Ser Gly Gly Tyr
        35                  40                  45

Gly Pro Gly Gly Gln Gly Pro Gly Gln Gln Gly Pro Gly Ser Ser Ala
        50                  55                  60

Ala Ala Ala Gly Pro Gly Gly Tyr Gly Pro Gly Gly Gln Gly Pro
65                  70                  75                  80

Ser Ala Ser Ala Ala Ala Ala Gly Pro Gly Ser Gly Gln Gln Gly
            85                  90                  95

Pro Gly Ala Ser Gly Gly Tyr Gly Pro Gly Gly Gln Gly Pro Gly Gln
            100                 105                 110

Gln Gly Pro Gly Ser Ser Ala Ala Ala Ala Gly Gly Tyr Gly Ser
        115                 120                 125

Gly Pro Gly Gln Gln Gly Pro Tyr Gly Ser Ala Ala Ala Ala Gly
        130                 135                 140

Pro Gly Ser Gly Gly Tyr Gly Gln Gly Pro Tyr Gly Pro Gly Ala Ser
145                 150                 155                 160
```

```
Gly Pro Gly Gly Tyr Gly Pro Gly Gly Gln Gly Pro Ser Ala Ser Ala
            165                 170                 175

Ala Ala Ala Ala Gly Ser Gly Gln Gln Gly Pro Gly Gly Tyr Gly Pro
        180                 185                 190

Tyr Ala Ser Ala Ala Ala Ala Gly Gly Tyr Gly Ser Gly Pro Gly
        195                 200                 205

Gln Gly Pro Tyr Gly Pro Gly Gly Ser Gly Ser Gly Gln Gln Gly
    210                 215                 220

Pro Gly Gln Gln Gly Pro Tyr Ala Ser Ala Ala Ala Ala Gly Pro
225                 230                 235                 240

Gly Gly Gln Gly Pro Tyr Gly Pro Gly Ser Ser Ala Ala Ala Ala
                245                 250                 255

Gly Gly Tyr Gly Tyr Gly Pro Gly Gln Gly Pro Tyr Gly Pro Gly
            260                 265                 270

Ala Ser Gly Gly Asn Gly Pro Gly Ser Gly Gly Tyr Gly Pro Gly Gln
        275                 280                 285

Gln Gly Pro Gly Gly Ser Ala Ala Ala Ala Gly Pro Gly Gly Gln
    290                 295                 300

Gly Pro Tyr Gly Pro Gly Ala Ser Ala Ala Ala Ala Gly Gly Tyr
305                 310                 315                 320

Gly Pro Gly Gly Gln Gly Pro Gly Gly Tyr Gly Pro Gly Ser Ser Gly
                325                 330                 335

Pro Gly Gly Gln Gly Pro Tyr Gly Pro Gly Ser Ser Ala Ala Ala
            340                 345                 350

Ala Gly Gly Tyr Gly Pro Gly Gln Gln Gly Pro Tyr Gly Pro Gly Gly
        355                 360                 365

Ser Ala Ala Ala Ala Gly Gly Tyr Gln Gln Gly Pro Gly Gly Gln
370                 375                 380

Gly Pro Tyr Gly Pro Gly Ala Ser Gly Pro Gly Gly Gln Gly Pro Tyr
385                 390                 395                 400

Gly Pro Gly Ala Ser Ala Ala Ala Ala Gly Pro Gly Gly Tyr Gly
            405                 410                 415

Pro Gly Gly Gln Gly Pro Ser Ala Ser Ala Ala Ala Ala Gly Gly
        420                 425                 430

Tyr Gly Ser Gly Pro Gly Gly Tyr Gly Pro Tyr Gly Pro Gly Gly Ser
435                 440                 445

Gly Pro Gly Ser Gly Gln Gln Gly Gln Gly Pro Tyr Gly Pro Gly Ala
        450                 455                 460

Ser Ala Ala Ala Ala Gly Gly Tyr Gly Pro Gly Gln Gln Gly Pro
465                 470                 475                 480

Tyr Gly Pro Gly Gly Ser Ala Ala Ala Ala Gly Pro Gly Ser Gly
            485                 490                 495

Gly Tyr Gly Pro Gly Ala Ser Gly Gly Asn Gly Pro Gly Ser Gly Gly
        500                 505                 510

Tyr Gly Pro Gly Gln Gln Gly Pro Gly Gly Ser Ala Ala Ala Ala
    515                 520                 525

Gly Gly Tyr Gln Gln Gly Pro Gly Gln Gly Pro Tyr Gly Pro Gly
                530                 535                 540

Ala Ser Ala Ala Ala Ala Gly Gly Tyr Ser Gly Pro Gly Gly Gln
545                 550                 555                 560

Gln Gly Pro Tyr Gly Pro Gly Gly Ser Gly Ser Gly Gln Gln Gly Pro
                565                 570                 575

Gly Gln Gln Gly Pro Tyr Ala Ser Ala Ala Ala Ala Gly Pro Gly
```

```
                        580                 585                 590
Ser Gly Gln Gln Gly Pro Gly Ala Ser
            595                 600

<210> SEQ ID NO 19
<211> LENGTH: 612
<212> TYPE: PRT
<213> ORGANISM: Artificial Sequence
<220> FEATURE:
<223> OTHER INFORMATION: Met-PRT720

<400> SEQUENCE: 19

Met Gly Pro Gly Gln Gln Gly Pro Tyr Gly Pro Gly Ala Ser Ala Ala
1               5                   10                  15

Ala Ala Ala Gly Gln Asn Gly Pro Gly Ser Gln Gln Gly Pro Gly
            20                  25                  30

Gln Ser Gly Gln Tyr Gly Pro Gly Gln Gly Pro Gly Gln Gln Gly
        35                  40                  45

Pro Gly Ser Ser Ala Ala Ala Ala Gly Pro Gly Gln Tyr Val Leu
    50                  55                  60

Ile Gly Pro Gly Gln Gln Val Leu Ile Gly Pro Ser Ala Ser Ala Ala
65                  70                  75                  80

Ala Ala Ala Gly Pro Gly Ser Gly Gln Gln Gly Pro Gly Ala Ser Gly
                85                  90                  95

Gln Tyr Gly Pro Gly Gln Gly Pro Gly Gln Gln Gly Pro Gly Ser
        100                 105                 110

Ser Ala Ala Ala Ala Ala Gly Ser Tyr Gly Ser Val Leu Ile Gly Pro
            115                 120                 125

Gly Gln Gln Val Leu Ile Gly Pro Tyr Gly Ser Ala Ala Ala Ala
    130                 135                 140

Gly Pro Gly Ser Gly Gln Tyr Gly Gln Gly Pro Tyr Gly Pro Gly Ala
145                 150                 155                 160

Ser Gly Pro Gly Gln Tyr Gly Pro Gly Gln Gly Pro Ser Ala Ser
                165                 170                 175

Ala Ala Ala Ala Gly Ser Gly Gln Gln Val Leu Ile Gly Pro Gly
            180                 185                 190

Gln Tyr Val Leu Ile Gly Pro Tyr Ala Ser Ala Ala Ala Ala Gly
        195                 200                 205

Gln Tyr Gly Ser Gly Pro Gly Gln Gly Pro Tyr Gly Pro Gly Gln
    210                 215                 220

Ser Gly Ser Gly Gln Gln Gly Pro Gly Gln Gly Pro Tyr Ala Ser
225                 230                 235                 240

Ala Ala Ala Ala Gly Pro Gly Gln Gln Val Leu Ile Gly Pro Tyr
                245                 250                 255

Val Leu Ile Gly Pro Gly Ser Ser Ala Ala Ala Ala Gly Gln Tyr
            260                 265                 270

Gly Tyr Gly Pro Gly Gln Gln Gly Pro Tyr Gly Pro Gly Ala Ser Gly
        275                 280                 285

Gln Asn Gly Pro Gly Ser Gly Gln Tyr Gly Pro Gly Gln Gln Gly Pro
    290                 295                 300

Gly Gln Ser Ala Ala Ala Ala Gly Pro Gly Gln Val Leu Ile
305                 310                 315                 320

Gly Pro Tyr Val Leu Ile Gly Pro Gly Ala Ser Ala Ala Ala Ala
                325                 330                 335

Gly Gln Tyr Gly Pro Gly Gln Gln Gly Pro Gly Gln Tyr Gly Pro Gly
```

```
                    340                 345                 350
Ser Ser Gly Pro Gly Gln Gln Gly Pro Tyr Gly Pro Gly Ser Ser Ala
            355                 360                 365

Ala Ala Ala Ala Gly Ser Tyr Gly Pro Gly Gln Gln Val Leu Ile Gly
        370                 375                 380

Pro Tyr Val Leu Ile Gly Pro Gly Ser Ala Ala Ala Ala Ala Ala Gly
385                 390                 395                 400

Gln Tyr Gln Gln Gly Pro Gly Gln Gln Gly Pro Tyr Gly Pro Gly Ala
                405                 410                 415

Ser Gly Pro Gly Gln Gln Gly Pro Tyr Gly Pro Gly Ala Ser Ala Ala
            420                 425                 430

Ala Ala Ala Gly Pro Gly Gln Tyr Val Leu Ile Gly Pro Gly Gln Gln
        435                 440                 445

Val Leu Ile Gly Pro Ser Ala Ser Ala Ala Ala Ala Gly Gln Tyr
        450                 455                 460

Gly Ser Gly Pro Gly Gln Tyr Gly Pro Tyr Gly Pro Gly Gln Ser Gly
465                 470                 475                 480

Pro Gly Ser Gly Gln Gln Gly Gln Gly Pro Tyr Gly Pro Gly Ala Ser
            485                 490                 495

Ala Ala Ala Ala Ala Gly Ser Tyr Gly Pro Gly Gln Gln Val Leu Ile
        500                 505                 510

Gly Pro Tyr Val Leu Ile Gly Pro Gly Ser Ala Ala Ala Ala
        515                 520                 525

Gly Pro Gly Ser Gly Gln Tyr Gly Pro Gly Ala Ser Gly Gln Asn Gly
        530                 535                 540

Pro Gly Ser Gly Gln Tyr Gly Pro Gly Gln Gln Gly Pro Gly Gln Ser
545                 550                 555                 560

Ala Ala Ala Ala Ala Gly Gln Tyr Gln Gln Val Leu Ile Gly Pro Gly
                565                 570                 575

Gln Gln Gly Pro Tyr Val Leu Ile Gly Pro Gly Ala Ser Ala Ala Ala
            580                 585                 590

Ala Ala Gly Pro Gly Ser Gly Gln Gln Val Leu Ile Gly Pro Gly Ala
        595                 600                 605

Ser Val Leu Ile
    610

<210> SEQ ID NO 20
<211> LENGTH: 592
<212> TYPE: PRT
<213> ORGANISM: Artificial Sequence
<220> FEATURE:
<223> OTHER INFORMATION: Met-PRT665

<400> SEQUENCE: 20

Met Gly Pro Gly Gln Gln Gly Pro Tyr Gly Pro Gly Ala Ser Ala Ala
1               5                   10                  15

Ala Ala Ala Ala Gly Ser Asn Gly Pro Gly Ser Gly Gln Gln Gly
            20                  25                  30

Pro Gly Gln Ser Gly Gln Tyr Gly Pro Gly Gln Gln Gly Pro Gly Gln
        35                  40                  45

Gln Gly Pro Gly Ser Ser Ala Ala Ala Ala Ala Gly Pro Gly
    50                  55                  60

Gln Tyr Val Leu Ile Gly Pro Gly Gln Gln Gly Pro Ser Ala Ser Ala
65                  70                  75                  80

Ala Ala Ala Ala Ala Gly Pro Gly Ser Gly Gln Gln Gly Pro Gly
```

```
                        85                  90                  95
Ala Ser Gly Gln Tyr Gly Pro Gly Gln Gln Gly Pro Gly Gln Gln Gly
                100                 105                 110
Pro Gly Ser Ser Ala Ala Ala Ala Ala Ala Gly Ser Tyr Gly Ser
            115                 120                 125
Val Leu Ile Gly Pro Gly Gln Gln Gly Pro Tyr Gly Ser Ala Ala Ala
            130                 135                 140
Ala Ala Ala Ala Gly Pro Gly Ser Gly Gln Tyr Gly Gln Gly Pro Tyr
145                 150                 155                 160
Gly Pro Gly Ala Ser Gly Pro Gly Gln Tyr Gly Pro Gly Gln Gln Gly
                165                 170                 175
Pro Ser Ala Ser Ala Ala Ala Ala Ala Ala Gly Ser Gly Gln Gln
            180                 185                 190
Val Leu Ile Gly Pro Gly Gln Tyr Gly Pro Tyr Ala Ser Ala Ala Ala
            195                 200                 205
Ala Ala Ala Ala Gly Ser Tyr Gly Ser Gly Pro Gly Gln Gln Gly Pro
            210                 215                 220
Tyr Gly Pro Gly Gln Ser Gly Ser Gly Gln Gln Gly Pro Gly Gln Gln
225                 230                 235                 240
Gly Pro Tyr Ala Ser Ala Ala Ala Ala Ala Ala Gly Pro Gly Gln
            245                 250                 255
Gln Val Leu Ile Gly Pro Tyr Gly Pro Gly Ser Ser Ala Ala Ala Ala
            260                 265                 270
Ala Ala Ala Gly Ser Tyr Gly Tyr Gly Pro Gly Gln Gln Gly Pro Tyr
            275                 280                 285
Gly Pro Gly Ala Ser Gly Gln Asn Gly Pro Gly Ser Gly Gln Tyr Gly
            290                 295                 300
Pro Gly Gln Gln Gly Pro Gly Pro Ser Ala Ala Ala Ala Ala Ala Ala
305                 310                 315                 320
Gly Pro Gly Gln Gln Val Leu Ile Gly Pro Tyr Gly Pro Gly Ala Ser
            325                 330                 335
Ala Ala Ala Ala Ala Ala Ala Gly Ser Tyr Gly Pro Gly Gln Gln Gly
            340                 345                 350
Pro Gly Gln Tyr Gly Pro Gly Ser Ser Gly Pro Gly Gln Gln Gly Pro
            355                 360                 365
Tyr Gly Pro Gly Ser Ser Ala Ala Ala Ala Ala Ala Gly Ser Tyr
            370                 375                 380
Gly Pro Gly Gln Gln Val Leu Ile Gly Pro Tyr Gly Pro Gly Pro Ser
385                 390                 395                 400
Ala Ala Ala Ala Ala Ala Ala Gly Ser Tyr Gln Gln Gly Pro Gly Gln
            405                 410                 415
Gln Gly Pro Tyr Gly Pro Gly Ala Ser Gly Pro Gly Gln Gln Gly Pro
            420                 425                 430
Tyr Gly Pro Gly Ala Ser Ala Ala Ala Ala Ala Ala Gly Pro Gly
            435                 440                 445
Gln Tyr Val Leu Ile Gly Pro Gly Gln Gln Gly Pro Ser Ala Ser Ala
            450                 455                 460
Ala Ala Ala Ala Ala Gly Ser Tyr Gly Ser Gly Pro Gly Gln Tyr
465                 470                 475                 480
Gly Pro Tyr Gly Pro Gly Gln Ser Gly Pro Gly Ser Gly Gln Gln Gly
            485                 490                 495
Gln Gly Pro Tyr Gly Pro Gly Ala Ser Ala Ala Ala Ala Ala Ala
            500                 505                 510
```

-continued

```
Gly Ser Tyr Gly Pro Gly Gln Gln Val Leu Ile Gly Pro Tyr Gly Pro
            515                 520                 525
Gly Pro Ser Ala Ala Ala Ala Ala Ala Gly Pro Gly Ser Gly Gln
        530                 535                 540
Tyr Gly Pro Gly Ala Ser Gly Gln Asn Gly Pro Gly Ser Gly Gln Tyr
545                 550                 555                 560
Gly Pro Gly Gln Gln Gly Pro Gly Pro Ser Ala Ala Ala Ala Ala
                565                 570                 575
Ala Gly Pro Gly Ser Gly Gln Gln Gly Pro Gly Ala Ser Val Leu Ile
        580                 585                 590
```

<210> SEQ ID NO 21
<211> LENGTH: 619
<212> TYPE: PRT
<213> ORGANISM: Artificial Sequence
<220> FEATURE:
<223> OTHER INFORMATION: Met-PRT666

<400> SEQUENCE: 21

```
Met Gly Pro Gly Gln Gln Gly Pro Tyr Gly Pro Gly Ala Ser Ala Ala
1               5                   10                  15
Ala Ala Ala Ala Gly Ser Asn Gly Pro Gly Ser Gly Gln Gln Gly
            20                  25                  30
Pro Gly Gln Ser Gly Gln Tyr Gly Pro Gly Gln Gln Gly Pro Gly Gln
        35                  40                  45
Gln Gly Pro Gly Ser Ser Ala Ala Ala Ala Ala Ala Gly Pro Gly
        50                  55                  60
Gln Tyr Val Leu Ile Gly Pro Gly Gln Gln Val Leu Ile Gly Pro Ser
65                  70                  75                  80
Ala Ser Ala Ala Ala Ala Ala Ala Gly Pro Gly Ser Gly Gln Gln
                85                  90                  95
Gly Pro Gly Ala Ser Gly Gln Tyr Gly Pro Gly Gln Gln Gly Pro Gly
            100                 105                 110
Gln Gln Gly Pro Gly Ser Ser Ala Ala Ala Ala Ala Ala Gly Ser
        115                 120                 125
Tyr Gly Ser Val Leu Ile Gly Pro Gly Gln Gln Val Leu Ile Gly Pro
        130                 135                 140
Tyr Gly Ser Ala Ala Ala Ala Ala Ala Gly Pro Gly Ser Gly Gln
145                 150                 155                 160
Tyr Gly Gln Gly Pro Tyr Gly Pro Gly Ala Ser Gly Pro Gly Gln Tyr
                165                 170                 175
Gly Pro Gly Gln Gln Gly Pro Ser Ala Ser Ala Ala Ala Ala Ala
            180                 185                 190
Ala Gly Ser Gly Gln Gln Val Leu Ile Gly Pro Gly Gln Tyr Val Leu
        195                 200                 205
Ile Gly Pro Tyr Ala Ser Ala Ala Ala Ala Ala Ala Gly Ser Tyr
        210                 215                 220
Gly Ser Gly Pro Gly Gln Gln Gly Pro Tyr Gly Pro Gly Gln Ser Gly
225                 230                 235                 240
Ser Gly Gln Gln Gly Pro Gly Gln Gln Gly Pro Tyr Ala Ser Ala Ala
                245                 250                 255
Ala Ala Ala Ala Gly Pro Gly Gln Gln Val Leu Ile Gly Pro Tyr
            260                 265                 270
Val Leu Ile Gly Pro Gly Ser Ser Ala Ala Ala Ala Ala Ala Gly
        275                 280                 285
```

Ser Tyr Gly Tyr Gly Pro Gly Gln Gln Gly Pro Tyr Gly Pro Gly Ala
        290                 295                 300

Ser Gly Gln Asn Gly Pro Gly Ser Gly Gln Tyr Gly Pro Gly Gln Gln
305                 310                 315                 320

Gly Pro Gly Pro Ser Ala Ala Ala Ala Ala Ala Gly Pro Gly Gln
            325                 330                 335

Gln Val Leu Ile Gly Pro Tyr Val Leu Ile Gly Pro Gly Ala Ser Ala
            340                 345                 350

Ala Ala Ala Ala Ala Ala Gly Ser Tyr Gly Pro Gly Gln Gln Gly Pro
            355                 360                 365

Gly Gln Tyr Gly Pro Gly Ser Ser Gly Pro Gly Gln Gln Gly Pro Tyr
        370                 375                 380

Gly Pro Gly Ser Ser Ala Ala Ala Ala Ala Ala Gly Ser Tyr Gly
385                 390                 395                 400

Pro Gly Gln Gln Val Leu Ile Gly Pro Tyr Val Leu Ile Gly Pro Gly
                405                 410                 415

Pro Ser Ala Ala Ala Ala Ala Ala Gly Ser Tyr Gln Gln Gly Pro
            420                 425                 430

Gly Gln Gln Gly Pro Tyr Gly Pro Gly Ala Ser Gly Pro Gly Gln Gln
        435                 440                 445

Gly Pro Tyr Gly Pro Gly Ala Ser Ala Ala Ala Ala Ala Ala Gly
        450                 455                 460

Pro Gly Gln Tyr Val Leu Ile Gly Pro Gly Gln Gln Val Leu Ile Gly
465                 470                 475                 480

Pro Ser Ala Ser Ala Ala Ala Ala Ala Gly Ser Tyr Gly Ser
            485                 490                 495

Gly Pro Gly Gln Tyr Gly Pro Tyr Gly Pro Gly Gln Ser Gly Pro Gly
                500                 505                 510

Ser Gly Gln Gln Gly Gln Gly Pro Tyr Gly Pro Gly Ala Ser Ala Ala
            515                 520                 525

Ala Ala Ala Ala Gly Ser Tyr Gly Pro Gly Gln Gln Val Leu Ile
            530                 535                 540

Gly Pro Tyr Val Leu Ile Gly Pro Gly Pro Ser Ala Ala Ala Ala Ala
545                 550                 555                 560

Ala Ala Gly Pro Gly Ser Gly Gln Tyr Gly Pro Gly Ala Ser Gly Gln
                565                 570                 575

Asn Gly Pro Gly Ser Gly Gln Tyr Gly Pro Gly Gln Gln Gly Pro Gly
            580                 585                 590

Pro Ser Ala Ala Ala Ala Ala Ala Gly Pro Gly Ser Gly Gln Gln
            595                 600                 605

Val Leu Ile Gly Pro Gly Ala Ser Val Leu Ile
        610                 615

<210> SEQ ID NO 22
<211> LENGTH: 623
<212> TYPE: PRT
<213> ORGANISM: Artificial Sequence
<220> FEATURE:
<223> OTHER INFORMATION: PRT720

<400> SEQUENCE: 22

Met His His His His His Ser Ser Gly Ser Ser Gly Pro Gly Gln
1               5                   10                  15

Gln Gly Pro Tyr Gly Pro Gly Ala Ser Ala Ala Ala Ala Ala Gly Gln
            20                  25                  30

```
Asn Gly Pro Gly Ser Gly Gln Gln Gly Pro Gly Gln Ser Gly Gln Tyr
    35                  40                  45

Gly Pro Gly Gln Gln Gly Pro Gly Gln Gln Gly Pro Gly Ser Ser Ala
    50                  55                  60

Ala Ala Ala Ala Gly Pro Gly Gln Tyr Val Leu Ile Gly Pro Gly Gln
65              70                  75                  80

Gln Val Leu Ile Gly Pro Ser Ala Ser Ala Ala Ala Ala Gly Pro
                85                  90                  95

Gly Ser Gly Gln Gln Gly Pro Gly Ala Ser Gly Gln Tyr Gly Pro Gly
                100                 105                 110

Gln Gln Gly Pro Gly Gln Gln Gly Pro Gly Ser Ser Ala Ala Ala
            115                 120                 125

Ala Gly Ser Tyr Gly Ser Val Leu Ile Gly Pro Gly Gln Gln Val Leu
130                 135                 140

Ile Gly Pro Tyr Gly Ser Ala Ala Ala Ala Gly Pro Gly Ser Gly
145             150                 155                 160

Gln Tyr Gly Gln Gly Pro Tyr Gly Pro Gly Ala Ser Gly Pro Gly Gln
                165                 170                 175

Tyr Gly Pro Gly Gln Gln Gly Pro Ser Ala Ser Ala Ala Ala Ala
            180                 185                 190

Gly Ser Gly Gln Gln Val Leu Ile Gly Pro Gly Gln Tyr Val Leu Ile
            195                 200                 205

Gly Pro Tyr Ala Ser Ala Ala Ala Ala Gly Gln Tyr Gly Ser Gly
210                 215                 220

Pro Gly Gln Gln Gly Pro Tyr Gly Pro Gly Ser Gly Ser Gly Gln
225                 230                 235                 240

Gln Gly Pro Gly Gln Gln Gly Pro Tyr Ala Ser Ala Ala Ala Ala
                245                 250                 255

Gly Pro Gly Gln Gln Val Leu Ile Gly Pro Tyr Val Leu Ile Gly Pro
            260                 265                 270

Gly Ser Ser Ala Ala Ala Ala Gly Gln Tyr Gly Tyr Gly Pro Gly
    275                 280                 285

Gln Gln Gly Pro Tyr Gly Pro Gly Ala Ser Gly Gln Asn Gly Pro Gly
    290                 295                 300

Ser Gly Gln Tyr Gly Pro Gly Gln Gly Pro Gly Gln Ser Ala Ala
305                 310                 315                 320

Ala Ala Ala Gly Pro Gly Gln Gln Val Leu Ile Gly Pro Tyr Val Leu
            325                 330                 335

Ile Gly Pro Gly Ala Ser Ala Ala Ala Ala Gly Gln Tyr Gly Pro
                340                 345                 350

Gly Gln Gln Gly Pro Gly Gln Tyr Gly Pro Gly Ser Ser Gly Pro Gly
    355                 360                 365

Gln Gln Gly Pro Tyr Gly Pro Gly Ser Ser Ala Ala Ala Ala Gly
    370                 375                 380

Ser Tyr Gly Pro Gly Gln Gln Val Leu Ile Gly Pro Tyr Val Leu Ile
385                 390                 395                 400

Gly Pro Gly Pro Ser Ala Ala Ala Ala Ala Gly Gln Tyr Gln Gln Gly
                405                 410                 415

Pro Gly Gln Gln Gly Pro Tyr Gly Pro Gly Ala Ser Gly Pro Gly Gln
            420                 425                 430

Gln Gly Pro Tyr Gly Pro Gly Ala Ser Ala Ala Ala Ala Gly Pro
            435                 440                 445
```

```
Gly Gln Tyr Val Leu Ile Gly Pro Gly Gln Val Leu Ile Gly Pro
    450                 455                 460

Ser Ala Ser Ala Ala Ala Ala Gly Gln Tyr Gly Ser Gly Pro Gly
465                 470                 475                 480

Gln Tyr Gly Pro Tyr Gly Pro Gly Gln Ser Gly Pro Gly Ser Gly Gln
                485                 490                 495

Gln Gly Gln Gly Pro Tyr Gly Pro Gly Ala Ser Ala Ala Ala Ala
            500                 505                 510

Gly Ser Tyr Gly Pro Gly Gln Val Leu Ile Gly Pro Tyr Val Leu
            515                 520                 525

Ile Gly Pro Gly Pro Ser Ala Ala Ala Ala Gly Pro Gly Ser Gly
            530                 535                 540

Gln Tyr Gly Pro Gly Ala Ser Gly Gln Asn Gly Pro Gly Ser Gly Gln
545                 550                 555                 560

Tyr Gly Pro Gly Gln Gln Gly Pro Gln Ser Ala Ala Ala Ala
                565                 570                 575

Gly Gln Tyr Gln Gln Val Leu Ile Gly Pro Gly Gln Gly Pro Tyr
            580                 585                 590

Val Leu Ile Gly Pro Gly Ala Ser Ala Ala Ala Ala Gly Pro Gly
            595                 600                 605

Ser Gly Gln Gln Val Leu Ile Gly Pro Gly Ala Ser Val Leu Ile
            610                 615                 620

<210> SEQ ID NO 23
<211> LENGTH: 603
<212> TYPE: PRT
<213> ORGANISM: Artificial Sequence
<220> FEATURE:
<223> OTHER INFORMATION: PRT665

<400> SEQUENCE: 23

Met His His His His His Ser Ser Gly Ser Ser Gly Pro Gly Gln
1               5                   10                  15

Gln Gly Pro Tyr Gly Pro Gly Ala Ser Ala Ala Ala Ala Ala Ala
                20                  25                  30

Gly Ser Asn Gly Pro Gly Ser Gly Gln Gln Gly Pro Gly Gln Ser Gly
            35                  40                  45

Gln Tyr Gly Pro Gly Gln Gln Gly Pro Gly Gln Gln Gly Pro Gly Ser
50                  55                  60

Ser Ala Ala Ala Ala Ala Ala Gly Pro Gly Gln Tyr Val Leu Ile
65                  70                  75                  80

Gly Pro Gly Gln Gln Gly Pro Ser Ala Ser Ala Ala Ala Ala Ala
                85                  90                  95

Ala Gly Pro Gly Ser Gly Gln Gln Gly Pro Gly Ala Ser Gly Gln Tyr
            100                 105                 110

Gly Pro Gly Gln Gln Gly Pro Gly Gln Gln Gly Pro Gly Ser Ser Ala
            115                 120                 125

Ala Ala Ala Ala Ala Gly Ser Tyr Gly Ser Val Leu Ile Gly Pro
            130                 135                 140

Gly Gln Gln Gly Pro Tyr Gly Ser Ala Ala Ala Ala Ala Ala Gly
145                 150                 155                 160

Pro Gly Ser Gly Gln Tyr Gly Gln Gly Pro Tyr Gly Pro Gly Ala Ser
                165                 170                 175

Gly Pro Gly Gln Tyr Gly Pro Gly Gln Gln Gly Pro Ser Ala Ser Ala
            180                 185                 190
```

```
Ala Ala Ala Ala Ala Gly Ser Gly Gln Gln Val Leu Ile Gly Pro
        195                 200                 205

Gly Gln Tyr Gly Pro Tyr Ala Ser Ala Ala Ala Ala Ala Ala Gly
    210                 215                 220

Ser Tyr Gly Ser Gly Pro Gly Gln Gln Gly Pro Tyr Gly Pro Gly Gln
225                 230                 235                 240

Ser Gly Ser Gly Gln Gln Gly Pro Gln Gln Gly Pro Tyr Ala Ser
                245                 250                 255

Ala Ala Ala Ala Ala Ala Gly Pro Gly Gln Gln Val Leu Ile Gly
            260                 265                 270

Pro Tyr Gly Pro Gly Ser Ser Ala Ala Ala Ala Ala Ala Gly Ser
    275                 280                 285

Tyr Gly Tyr Gly Pro Gly Gln Gln Gly Pro Tyr Gly Pro Gly Ala Ser
    290                 295                 300

Gly Gln Asn Gly Pro Gly Ser Gly Gln Tyr Gly Pro Gly Gln Gln Gly
305                 310                 315                 320

Pro Gly Pro Ser Ala Ala Ala Ala Ala Ala Gly Pro Gly Gln Gln
                325                 330                 335

Val Leu Ile Gly Pro Tyr Gly Pro Gly Ala Ser Ala Ala Ala Ala
            340                 345                 350

Ala Ala Gly Ser Tyr Gly Pro Gly Gln Gln Gly Pro Gly Gln Tyr Gly
            355                 360                 365

Pro Gly Ser Ser Gly Pro Gly Gln Gln Gly Pro Tyr Gly Pro Gly Ser
    370                 375                 380

Ser Ala Ala Ala Ala Ala Ala Gly Ser Tyr Gly Pro Gly Gln Gln
385                 390                 395                 400

Val Leu Ile Gly Pro Tyr Gly Pro Gly Pro Ser Ala Ala Ala Ala
            405                 410                 415

Ala Ala Gly Ser Tyr Gln Gln Gly Pro Gly Gln Gln Gly Pro Tyr Gly
            420                 425                 430

Pro Gly Ala Ser Gly Pro Gly Gln Gln Gly Pro Tyr Gly Pro Gly Ala
    435                 440                 445

Ser Ala Ala Ala Ala Ala Ala Gly Pro Gly Gln Tyr Val Leu Ile
450                 455                 460

Gly Pro Gly Gln Gln Gly Pro Ser Ala Ser Ala Ala Ala Ala Ala
465                 470                 475                 480

Ala Gly Ser Tyr Gly Ser Gly Pro Gly Gln Tyr Gly Pro Tyr Gly Pro
            485                 490                 495

Gly Gln Ser Gly Pro Gly Ser Gly Gln Gln Gly Gln Gly Pro Tyr Gly
                500                 505                 510

Pro Gly Ala Ser Ala Ala Ala Ala Ala Ala Gly Ser Tyr Gly Pro
                515                 520                 525

Gly Gln Gln Val Leu Ile Gly Pro Tyr Gly Pro Gly Pro Ser Ala Ala
    530                 535                 540

Ala Ala Ala Ala Gly Pro Gly Ser Gly Gln Tyr Gly Pro Gly Ala
545                 550                 555                 560

Ser Gly Gln Asn Gly Pro Gly Ser Gly Gln Tyr Gly Pro Gly Gln Gln
                565                 570                 575

Gly Pro Gly Pro Ser Ala Ala Ala Ala Ala Ala Gly Pro Gly Ser
                580                 585                 590

Gly Gln Gln Gly Pro Gly Ala Ser Val Leu Ile
    595                 600
```

```
<210> SEQ ID NO 24
<211> LENGTH: 630
<212> TYPE: PRT
<213> ORGANISM: Artificial Sequence
<220> FEATURE:
<223> OTHER INFORMATION: PRT666

<400> SEQUENCE: 24

Met His His His His His Ser Ser Gly Ser Ser Gly Pro Gly Gln
1               5                   10                  15

Gln Gly Pro Tyr Gly Pro Gly Ala Ser Ala Ala Ala Ala Ala Ala
                20                  25                  30

Gly Ser Asn Gly Pro Gly Ser Gly Gln Gln Gly Pro Gly Gln Ser Gly
            35                  40                  45

Gln Tyr Gly Pro Gly Gln Gln Gly Pro Gly Gln Gln Gly Pro Gly Ser
    50                  55                  60

Ser Ala Ala Ala Ala Ala Ala Gly Pro Gly Gln Tyr Val Leu Ile
65                  70                  75                  80

Gly Pro Gly Gln Gln Val Leu Ile Gly Pro Ser Ala Ser Ala Ala
                85                  90                  95

Ala Ala Ala Ala Gly Pro Gly Ser Gly Gln Gln Gly Pro Gly Ala Ser
            100                 105                 110

Gly Gln Tyr Gly Pro Gly Gln Gln Gly Pro Gly Gln Gln Gly Pro Gly
    115                 120                 125

Ser Ser Ala Ala Ala Ala Ala Ala Gly Ser Tyr Gly Ser Val Leu
130                 135                 140

Ile Gly Pro Gly Gln Gln Val Leu Ile Gly Pro Tyr Gly Ser Ala Ala
145                 150                 155                 160

Ala Ala Ala Ala Ala Gly Pro Gly Ser Gly Gln Tyr Gly Gln Gly Pro
            165                 170                 175

Tyr Gly Pro Gly Ala Ser Gly Pro Gly Gln Tyr Gly Pro Gly Gln Gln
    180                 185                 190

Gly Pro Ser Ala Ser Ala Ala Ala Ala Ala Gly Ser Gly Gln
            195                 200                 205

Gln Val Leu Ile Gly Pro Gly Gln Tyr Val Leu Ile Gly Pro Tyr Ala
    210                 215                 220

Ser Ala Ala Ala Ala Ala Ala Gly Ser Tyr Gly Ser Gly Pro Gly
225                 230                 235                 240

Gln Gln Gly Pro Tyr Gly Pro Gly Gln Ser Gly Ser Gly Gln Gln Gly
            245                 250                 255

Pro Gly Gln Gln Gly Pro Tyr Ala Ser Ala Ala Ala Ala Ala Ala
            260                 265                 270

Gly Pro Gly Gln Gln Val Leu Ile Gly Pro Tyr Val Leu Ile Gly Pro
            275                 280                 285

Gly Ser Ser Ala Ala Ala Ala Ala Ala Gly Ser Tyr Gly Tyr Gly
            290                 295                 300

Pro Gly Gln Gln Gly Pro Tyr Gly Pro Gly Ala Ser Gly Gln Asn Gly
305                 310                 315                 320

Pro Gly Ser Gly Gln Tyr Gly Pro Gly Gln Gln Gly Pro Gly Pro Ser
            325                 330                 335

Ala Ala Ala Ala Ala Ala Gly Pro Gly Gln Gln Val Leu Ile Gly
            340                 345                 350

Pro Tyr Val Leu Ile Gly Pro Gly Ala Ser Ala Ala Ala Ala Ala
    355                 360                 365

Ala Gly Ser Tyr Gly Pro Gly Gln Gln Gly Pro Gly Gln Tyr Gly Pro
```

```
                    370                 375                 380
Gly Ser Ser Gly Pro Gly Gln Gln Gly Pro Tyr Gly Pro Gly Ser Ser
385                 390                 395                 400

Ala Ala Ala Ala Ala Ala Gly Ser Tyr Gly Pro Gly Gln Gln Val
                405                 410                 415

Leu Ile Gly Pro Tyr Val Leu Ile Gly Pro Gly Pro Ser Ala Ala
                420                 425                 430

Ala Ala Ala Ala Gly Ser Tyr Gln Gln Gly Pro Gly Gln Gln Gly Pro
                435                 440                 445

Tyr Gly Pro Gly Ala Ser Gly Pro Gln Gln Gly Pro Tyr Gly Pro
            450                 455                 460

Gly Ala Ser Ala Ala Ala Ala Ala Ala Gly Pro Gly Gln Tyr Val
465                 470                 475                 480

Leu Ile Gly Pro Gly Gln Gln Val Leu Ile Gly Pro Ser Ala Ser Ala
                485                 490                 495

Ala Ala Ala Ala Ala Gly Ser Tyr Gly Ser Gly Pro Gly Gln Tyr
                500                 505                 510

Gly Pro Tyr Gly Pro Gly Gln Ser Gly Pro Gly Ser Gly Gln Gln Gly
            515                 520                 525

Gln Gly Pro Tyr Gly Pro Gly Ala Ser Ala Ala Ala Ala Ala Ala
            530                 535                 540

Gly Ser Tyr Gly Pro Gly Gln Gln Val Leu Ile Gly Pro Tyr Val Leu
545                 550                 555                 560

Ile Gly Pro Gly Pro Ser Ala Ala Ala Ala Ala Ala Gly Pro Gly
                565                 570                 575

Ser Gly Gln Tyr Gly Pro Gly Ala Ser Gly Gln Asn Gly Pro Gly Ser
                580                 585                 590

Gly Gln Tyr Gly Pro Gly Gln Gln Gly Pro Gly Pro Ser Ala Ala Ala
                595                 600                 605

Ala Ala Ala Ala Gly Pro Gly Ser Gly Gln Gln Val Leu Ile Gly Pro
                610                 615                 620

Gly Ala Ser Val Leu Ile
625                 630

<210> SEQ ID NO 25
<211> LENGTH: 593
<212> TYPE: PRT
<213> ORGANISM: Artificial Sequence
<220> FEATURE:
<223> OTHER INFORMATION: M_PRT888

<400> SEQUENCE: 25

Met Gly Ser Ser Gly Pro Gly Val Leu Gly Pro Tyr Gly Pro Gly Ala
1               5                   10                  15

Ser Ala Ala Ala Ala Gly Gln Asn Gly Pro Gly Ser Gly Val Leu
                20                  25                  30

Gly Pro Gly Gln Ser Gly Gln Tyr Gly Pro Gly Val Leu Gly Pro Gly
            35                  40                  45

Val Leu Gly Pro Gly Ser Ala Ala Ala Ala Gly Pro Gly Gln
50                  55                  60

Tyr Gly Pro Gly Val Leu Gly Pro Ser Ala Ser Ala Ala Ala Ala
65                  70                  75                  80

Gly Pro Gly Ser Gly Val Leu Gly Pro Gly Ala Ser Gly Gln Tyr Gly
                85                  90                  95

Pro Gly Val Leu Gly Pro Gly Val Leu Gly Pro Gly Ser Ser Ala Ala
```

```
                100                 105                 110
Ala Ala Ala Gly Gln Tyr Gly Ser Gly Pro Gly Val Leu Gly Pro Tyr
            115                 120                 125
Gly Ser Ala Ala Ala Ala Gly Pro Gly Ser Gly Gln Tyr Gly Gln
        130                 135                 140
Gly Pro Tyr Gly Pro Gly Ala Ser Gly Pro Gly Gln Tyr Gly Pro Gly
145                 150                 155                 160
Val Leu Gly Pro Ser Ala Ser Ala Ala Ala Ala Gly Ser Gly Val
                165                 170                 175
Leu Gly Pro Gly Gln Tyr Gly Pro Tyr Ala Ser Ala Ala Ala Ala
            180                 185                 190
Gly Gln Tyr Gly Ser Gly Pro Gly Val Leu Gly Pro Tyr Gly Pro Gly
        195                 200                 205
Gln Ser Gly Ser Gly Val Leu Gly Pro Gly Val Leu Gly Pro Tyr Ala
    210                 215                 220
Ser Ala Ala Ala Ala Gly Pro Gly Val Leu Gly Pro Tyr Gly Pro
225                 230                 235                 240
Gly Ser Ser Ala Ala Ala Ala Gly Gln Tyr Gly Tyr Gly Pro Gly
                245                 250                 255
Val Leu Gly Pro Tyr Gly Pro Gly Ala Ser Gly Gln Asn Gly Pro Gly
            260                 265                 270
Ser Gly Gln Tyr Gly Pro Gly Val Leu Gly Pro Gly Gln Ser Ala Ala
        275                 280                 285
Ala Ala Ala Gly Pro Gly Val Leu Gly Pro Tyr Gly Pro Gly Ala Ser
    290                 295                 300
Ala Ala Ala Ala Gly Gln Tyr Gly Pro Gly Val Leu Gly Pro Gly
305                 310                 315                 320
Gln Tyr Gly Pro Gly Ser Ser Gly Pro Gly Val Leu Gly Pro Tyr Gly
                325                 330                 335
Pro Gly Ser Ser Ala Ala Ala Ala Gly Gln Tyr Gly Pro Gly Val
            340                 345                 350
Leu Gly Pro Tyr Gly Pro Gly Gln Ser Ala Ala Ala Ala Gly Gln
        355                 360                 365
Tyr Val Leu Gly Pro Gly Val Leu Gly Pro Tyr Gly Pro Gly Ala Ser
    370                 375                 380
Gly Pro Gly Val Leu Gly Pro Tyr Gly Pro Gly Ala Ser Ala Ala Ala
385                 390                 395                 400
Ala Ala Gly Pro Gly Gln Tyr Gly Pro Gly Val Leu Gly Pro Ser Ala
                405                 410                 415
Ser Ala Ala Ala Ala Gly Gln Tyr Gly Ser Gly Pro Gly Gln Tyr
            420                 425                 430
Gly Pro Tyr Gly Pro Gly Gln Ser Gly Pro Gly Ser Gly Val Leu Gly
        435                 440                 445
Gln Gly Pro Tyr Gly Pro Gly Ala Ser Ala Ala Ala Ala Gly Gln
    450                 455                 460
Tyr Gly Pro Gly Val Leu Gly Pro Tyr Gly Pro Gly Gln Ser Ala Ala
465                 470                 475                 480
Ala Ala Ala Gly Pro Gly Ser Gly Gln Tyr Gly Pro Gly Ala Ser Gly
                485                 490                 495
Gln Asn Gly Pro Gly Ser Gly Gln Tyr Gly Pro Gly Val Leu Gly Pro
            500                 505                 510
Gly Gln Ser Ala Ala Ala Ala Gly Gln Tyr Val Leu Gly Pro Gly
        515                 520                 525
```

Val Leu Gly Pro Tyr Gly Pro Gly Ala Ser Ala Ala Ala Ala Gly
            530                 535                 540

Gln Tyr Gly Ser Gly Pro Gly Val Leu Gly Pro Tyr Gly Pro Gly Gln
545                 550                 555                 560

Ser Gly Ser Gly Val Leu Gly Pro Gly Val Leu Gly Pro Tyr Ala Ser
                565                 570                 575

Ala Ala Ala Ala Gly Pro Gly Ser Gly Val Leu Gly Pro Gly Ala
            580                 585                 590

Ser

<210> SEQ ID NO 26
<211> LENGTH: 590
<212> TYPE: PRT
<213> ORGANISM: Artificial Sequence
<220> FEATURE:
<223> OTHER INFORMATION: M_PRT965

<400> SEQUENCE: 26

Met Gly Pro Gly Thr Ser Gly Pro Tyr Gly Pro Gly Ala Ser Ala Ala
1               5                   10                  15

Ala Ala Ala Gly Ala Asn Gly Pro Gly Ser Gly Thr Ser Gly Pro Gly
            20                  25                  30

Ala Ser Gly Ala Tyr Gly Pro Gly Thr Ser Pro Gly Thr Ser Gly
        35                  40                  45

Pro Gly Ser Ser Ala Ala Ala Ala Gly Pro Gly Ala Tyr Gly Pro
    50                  55                  60

Gly Thr Ser Gly Pro Ser Ala Ser Ala Ala Ala Ala Gly Pro Gly
65                  70                  75                  80

Ser Gly Thr Ser Gly Pro Gly Ala Ser Gly Ala Tyr Gly Pro Gly Thr
                85                  90                  95

Ser Gly Pro Gly Thr Ser Gly Pro Gly Ser Ser Ala Ala Ala Ala
            100                 105                 110

Gly Ala Tyr Gly Ser Gly Pro Gly Thr Ser Gly Pro Tyr Gly Ser Ala
            115                 120                 125

Ala Ala Ala Ala Gly Pro Gly Ser Gly Ala Tyr Gly Ala Gly Pro Tyr
        130                 135                 140

Gly Pro Gly Ala Ser Gly Pro Gly Ala Tyr Gly Pro Gly Thr Ser Gly
145                 150                 155                 160

Pro Ser Ala Ser Ala Ala Ala Ala Gly Ser Gly Thr Ser Gly Pro
            165                 170                 175

Gly Ala Tyr Gly Pro Tyr Ala Ser Ala Ala Ala Ala Gly Ala Tyr
            180                 185                 190

Gly Ser Gly Pro Gly Thr Ser Gly Pro Tyr Gly Pro Gly Ala Ser Gly
        195                 200                 205

Ser Gly Thr Ser Gly Pro Gly Thr Ser Gly Pro Tyr Ala Ser Ala Ala
            210                 215                 220

Ala Ala Ala Gly Pro Gly Thr Ser Gly Pro Tyr Gly Pro Gly Ser Ser
225                 230                 235                 240

Ala Ala Ala Ala Ala Gly Ala Tyr Gly Tyr Gly Pro Gly Thr Ser Gly
                245                 250                 255

Pro Tyr Gly Pro Gly Ala Ser Gly Ala Asn Gly Pro Gly Ser Gly Ala
            260                 265                 270

Tyr Gly Pro Gly Thr Ser Gly Pro Gly Ala Ser Ala Ala Ala Ala Ala
            275                 280                 285

```
Gly Pro Gly Thr Ser Gly Pro Tyr Gly Pro Gly Ala Ser Ala Ala Ala
            290                 295                 300

Ala Ala Gly Ala Tyr Gly Pro Gly Thr Ser Gly Pro Gly Ala Tyr Gly
305                 310                 315                 320

Pro Gly Ser Ser Gly Pro Gly Thr Ser Gly Pro Tyr Gly Pro Gly Ser
                325                 330                 335

Ser Ala Ala Ala Ala Gly Ala Tyr Gly Pro Gly Thr Ser Gly Pro
            340                 345                 350

Tyr Gly Pro Gly Ala Ser Ala Ala Ala Ala Gly Ala Tyr Thr Ser
            355                 360                 365

Gly Pro Gly Thr Ser Gly Pro Tyr Gly Pro Gly Ala Ser Gly Pro Gly
            370                 375                 380

Thr Ser Gly Pro Tyr Gly Pro Gly Ala Ser Ala Ala Ala Ala Gly
385                 390                 395                 400

Pro Gly Ala Tyr Gly Pro Gly Thr Ser Gly Pro Ser Ala Ser Ala Ala
                405                 410                 415

Ala Ala Ala Gly Ala Tyr Gly Ser Gly Pro Gly Ala Tyr Gly Pro Tyr
            420                 425                 430

Gly Pro Gly Ala Ser Gly Pro Gly Ser Gly Thr Ser Gly Ala Gly Pro
            435                 440                 445

Tyr Gly Pro Gly Ala Ser Ala Ala Ala Ala Gly Ala Tyr Gly Pro
            450                 455                 460

Gly Thr Ser Gly Pro Tyr Gly Pro Gly Ala Ser Ala Ala Ala Ala
465                 470                 475                 480

Gly Pro Gly Ser Gly Ala Tyr Gly Pro Gly Ala Ser Gly Ala Asn Gly
                485                 490                 495

Pro Gly Ser Gly Ala Tyr Gly Pro Gly Thr Ser Gly Pro Gly Ala Ser
            500                 505                 510

Ala Ala Ala Ala Gly Ala Tyr Thr Ser Gly Pro Gly Thr Ser Gly
            515                 520                 525

Pro Tyr Gly Pro Gly Ala Ser Ala Ala Ala Ala Gly Ala Tyr Gly
            530                 535                 540

Ser Gly Pro Gly Thr Ser Gly Pro Tyr Gly Pro Gly Ala Ser Gly Ser
545                 550                 555                 560

Gly Thr Ser Gly Pro Gly Thr Ser Gly Pro Tyr Ala Ser Ala Ala
                565                 570                 575

Ala Ala Gly Pro Gly Ser Gly Thr Ser Gly Pro Gly Ala Ser
            580                 585                 590

<210> SEQ ID NO 27
<211> LENGTH: 593
<212> TYPE: PRT
<213> ORGANISM: Artificial Sequence
<220> FEATURE:
<223> OTHER INFORMATION: M_PRT889

<400> SEQUENCE: 27

Met Gly Ser Ser Gly Pro Gly Val Leu Gly Pro Tyr Gly Pro Gly Ala
1               5                   10                  15

Ser Ala Ala Ala Ala Gly Ile Asn Gly Pro Gly Ser Gly Val Leu
            20                  25                  30

Gly Pro Gly Ile Ser Gly Ile Tyr Gly Pro Gly Val Leu Gly Pro Gly
            35                  40                  45

Val Leu Gly Pro Gly Ser Ser Ala Ala Ala Ala Gly Pro Gly Ile
    50                  55                  60
```

-continued

Tyr Gly Pro Gly Val Leu Gly Pro Ser Ala Ser Ala Ala Ala Ala
 65                  70                  75                  80

Gly Pro Gly Ser Gly Val Leu Gly Pro Gly Ala Ser Gly Ile Tyr Gly
                 85                  90                  95

Pro Gly Val Leu Gly Pro Gly Val Leu Gly Pro Gly Ser Ser Ala Ala
            100                 105                 110

Ala Ala Ala Gly Ile Tyr Gly Ser Gly Pro Gly Val Leu Gly Pro Tyr
        115                 120                 125

Gly Ser Ala Ala Ala Ala Gly Pro Gly Ser Gly Ile Tyr Gly Ile
    130                 135                 140

Gly Pro Tyr Gly Pro Gly Ala Ser Gly Pro Gly Ile Tyr Gly Pro Gly
145                 150                 155                 160

Val Leu Gly Pro Ser Ala Ser Ala Ala Ala Ala Gly Ser Gly Val
                165                 170                 175

Leu Gly Pro Gly Ile Tyr Gly Pro Tyr Ala Ser Ala Ala Ala Ala
            180                 185                 190

Gly Ile Tyr Gly Ser Gly Pro Gly Val Leu Gly Pro Tyr Gly Pro Gly
        195                 200                 205

Ile Ser Gly Ser Gly Val Leu Gly Pro Gly Val Leu Gly Pro Tyr Ala
    210                 215                 220

Ser Ala Ala Ala Ala Gly Pro Gly Val Leu Gly Pro Tyr Gly Pro
225                 230                 235                 240

Gly Ser Ser Ala Ala Ala Ala Gly Ile Tyr Gly Tyr Gly Pro Gly
                245                 250                 255

Val Leu Gly Pro Tyr Gly Pro Gly Ala Ser Gly Ile Asn Gly Pro Gly
            260                 265                 270

Ser Gly Ile Tyr Gly Pro Gly Val Leu Gly Pro Gly Ile Ser Ala Ala
        275                 280                 285

Ala Ala Ala Gly Pro Gly Val Leu Gly Pro Tyr Gly Pro Gly Ala Ser
    290                 295                 300

Ala Ala Ala Ala Gly Ile Tyr Gly Pro Gly Val Leu Gly Pro Gly
305                 310                 315                 320

Ile Tyr Gly Pro Gly Ser Ser Gly Pro Gly Val Leu Gly Pro Tyr Gly
                325                 330                 335

Pro Gly Ser Ser Ala Ala Ala Ala Gly Ile Tyr Gly Pro Gly Val
            340                 345                 350

Leu Gly Pro Tyr Gly Pro Gly Ile Ser Ala Ala Ala Ala Gly Ile
        355                 360                 365

Tyr Val Leu Gly Pro Gly Val Leu Gly Pro Tyr Gly Pro Gly Ala Ser
370                 375                 380

Gly Pro Gly Val Leu Gly Pro Tyr Gly Pro Gly Ala Ser Ala Ala Ala
385                 390                 395                 400

Ala Ala Gly Pro Gly Ile Tyr Gly Pro Gly Val Leu Gly Pro Ser Ala
            405                 410                 415

Ser Ala Ala Ala Ala Gly Ile Tyr Gly Ser Gly Pro Gly Ile Tyr
        420                 425                 430

Gly Pro Tyr Gly Pro Gly Ile Ser Gly Pro Gly Ser Gly Val Leu Gly
        435                 440                 445

Ile Gly Pro Tyr Gly Pro Gly Ala Ser Ala Ala Ala Ala Gly Ile
    450                 455                 460

Tyr Gly Pro Gly Val Leu Gly Pro Tyr Gly Pro Gly Ile Ser Ala Ala
465                 470                 475                 480

Ala Ala Ala Gly Pro Gly Ser Gly Ile Tyr Gly Pro Gly Ala Ser Gly

```
                    485                 490                 495
Ile Asn Gly Pro Gly Ser Gly Ile Tyr Gly Pro Gly Val Leu Gly Pro
                500                 505                 510
Gly Ile Ser Ala Ala Ala Ala Gly Ile Tyr Val Leu Gly Pro Gly
            515                 520                 525
Val Leu Gly Pro Tyr Gly Pro Gly Ala Ser Ala Ala Ala Ala Gly
        530                 535                 540
Ile Tyr Gly Ser Gly Pro Gly Val Leu Gly Pro Tyr Gly Pro Gly Ile
545                 550                 555                 560
Ser Gly Ser Gly Val Leu Gly Pro Gly Val Leu Gly Pro Tyr Ala Ser
                565                 570                 575
Ala Ala Ala Ala Ala Gly Pro Gly Ser Gly Val Leu Gly Pro Gly Ala
                580                 585                 590
Ser

<210> SEQ ID NO 28
<211> LENGTH: 590
<212> TYPE: PRT
<213> ORGANISM: Artificial Sequence
<220> FEATURE:
<223> OTHER INFORMATION: M_PRT916

<400> SEQUENCE: 28

Met Gly Pro Gly Val Ile Gly Pro Tyr Gly Pro Gly Ala Ser Ala Ala
1               5                   10                  15
Ala Ala Ala Gly Leu Asn Gly Pro Gly Ser Gly Val Ile Gly Pro Gly
                20                  25                  30
Leu Ser Gly Leu Tyr Gly Pro Gly Val Ile Gly Pro Gly Val Ile Gly
            35                  40                  45
Pro Gly Ser Ser Ala Ala Ala Ala Ala Gly Pro Gly Leu Tyr Gly Pro
        50                  55                  60
Gly Val Ile Gly Pro Ser Ala Ser Ala Ala Ala Ala Gly Pro Gly
65                  70                  75                  80
Ser Gly Val Ile Gly Pro Gly Ala Ser Gly Leu Tyr Gly Pro Gly Val
                85                  90                  95
Ile Gly Pro Gly Val Ile Gly Pro Gly Ser Ser Ala Ala Ala Ala Ala
            100                 105                 110
Gly Leu Tyr Gly Ser Gly Pro Gly Val Ile Gly Pro Tyr Gly Ser Ala
        115                 120                 125
Ala Ala Ala Ala Gly Pro Gly Ser Gly Leu Tyr Gly Leu Gly Pro Tyr
130                 135                 140
Gly Pro Gly Ala Ser Gly Pro Gly Leu Tyr Gly Pro Gly Val Ile Gly
145                 150                 155                 160
Pro Ser Ala Ser Ala Ala Ala Ala Gly Ser Gly Val Ile Gly Pro
                165                 170                 175
Gly Leu Tyr Gly Pro Tyr Ala Ser Ala Ala Ala Ala Gly Leu Tyr
            180                 185                 190
Gly Ser Gly Pro Gly Val Ile Gly Pro Tyr Gly Pro Gly Leu Ser Gly
        195                 200                 205
Ser Gly Val Ile Gly Pro Gly Val Ile Gly Pro Tyr Ala Ser Ala Ala
            210                 215                 220
Ala Ala Ala Gly Pro Gly Val Ile Gly Pro Tyr Gly Pro Gly Ser Ser
225                 230                 235                 240
Ala Ala Ala Ala Ala Gly Leu Tyr Gly Tyr Gly Pro Gly Val Ile Gly
                245                 250                 255
```

```
Pro Tyr Gly Pro Gly Ala Ser Gly Leu Asn Gly Pro Gly Ser Gly Leu
            260                 265                 270

Tyr Gly Pro Gly Val Ile Gly Pro Gly Leu Ser Ala Ala Ala Ala Ala
        275                 280                 285

Gly Pro Gly Val Ile Gly Pro Tyr Gly Pro Gly Ala Ser Ala Ala Ala
    290                 295                 300

Ala Ala Gly Leu Tyr Gly Pro Gly Val Ile Gly Pro Gly Leu Tyr Gly
305                 310                 315                 320

Pro Gly Ser Ser Gly Pro Gly Val Ile Gly Pro Tyr Gly Pro Gly Ser
            325                 330                 335

Ser Ala Ala Ala Ala Gly Leu Tyr Gly Pro Gly Val Ile Gly Pro
        340                 345                 350

Tyr Gly Pro Gly Leu Ser Ala Ala Ala Ala Gly Leu Tyr Val Ile
        355                 360                 365

Gly Pro Gly Val Ile Gly Pro Tyr Gly Pro Gly Ala Ser Gly Pro Gly
    370                 375                 380

Val Ile Gly Pro Tyr Gly Pro Gly Ala Ser Ala Ala Ala Ala Gly
385                 390                 395                 400

Pro Gly Leu Tyr Gly Pro Gly Val Ile Gly Pro Ser Ala Ser Ala Ala
            405                 410                 415

Ala Ala Ala Gly Leu Tyr Gly Ser Gly Pro Gly Leu Tyr Gly Pro Tyr
            420                 425                 430

Gly Pro Gly Leu Ser Gly Pro Gly Ser Gly Val Ile Gly Leu Gly Pro
            435                 440                 445

Tyr Gly Pro Gly Ala Ser Ala Ala Ala Ala Gly Leu Tyr Gly Pro
        450                 455                 460

Gly Val Ile Gly Pro Tyr Gly Pro Gly Leu Ser Ala Ala Ala Ala
465                 470                 475                 480

Gly Pro Gly Ser Gly Leu Tyr Gly Pro Gly Ala Ser Gly Leu Asn Gly
            485                 490                 495

Pro Gly Ser Gly Leu Tyr Gly Pro Gly Val Ile Gly Pro Gly Leu Ser
            500                 505                 510

Ala Ala Ala Ala Ala Gly Leu Tyr Val Ile Gly Pro Gly Val Ile Gly
            515                 520                 525

Pro Tyr Gly Pro Gly Ala Ser Ala Ala Ala Ala Gly Leu Tyr Gly
        530                 535                 540

Ser Gly Pro Gly Val Ile Gly Pro Tyr Gly Pro Gly Leu Ser Gly Ser
545                 550                 555                 560

Gly Val Ile Gly Pro Gly Val Ile Gly Pro Tyr Ala Ser Ala Ala Ala
                565                 570                 575

Ala Ala Gly Pro Gly Ser Gly Val Ile Gly Pro Gly Ala Ser
            580                 585                 590

<210> SEQ ID NO 29
<211> LENGTH: 590
<212> TYPE: PRT
<213> ORGANISM: Artificial Sequence
<220> FEATURE:
<223> OTHER INFORMATION: M_ PRT918

<400> SEQUENCE: 29

Met Gly Pro Gly Val Phe Gly Pro Tyr Gly Pro Gly Ala Ser Ala Ala
1               5                   10                  15

Ala Ala Ala Gly Ile Asn Gly Pro Gly Ser Gly Val Phe Gly Pro Gly
            20                  25                  30
```

```
Ile Ser Gly Ile Tyr Gly Pro Gly Val Phe Gly Pro Gly Val Phe Gly
         35                  40                  45
Pro Gly Ser Ser Ala Ala Ala Ala Ala Gly Pro Ile Tyr Gly Pro
 50                  55                  60
Gly Val Phe Gly Pro Ser Ala Ser Ala Ala Ala Ala Gly Pro Gly
 65                  70                  75                  80
Ser Gly Val Phe Gly Pro Gly Ala Ser Gly Ile Tyr Gly Pro Gly Val
                 85                  90                  95
Phe Gly Pro Gly Val Phe Gly Pro Gly Ser Ser Ala Ala Ala Ala
            100                 105                 110
Gly Ile Tyr Gly Ser Gly Pro Gly Val Phe Gly Pro Tyr Gly Ser Ala
            115                 120                 125
Ala Ala Ala Ala Gly Pro Gly Ser Gly Ile Tyr Gly Ile Gly Pro Tyr
130                 135                 140
Gly Pro Gly Ala Ser Gly Pro Gly Ile Tyr Gly Pro Gly Val Phe Gly
145                 150                 155                 160
Pro Ser Ala Ser Ala Ala Ala Ala Gly Ser Gly Val Phe Gly Pro
            165                 170                 175
Gly Ile Tyr Gly Pro Tyr Ala Ser Ala Ala Ala Ala Gly Ile Tyr
            180                 185                 190
Gly Ser Gly Pro Gly Val Phe Gly Pro Tyr Gly Pro Gly Ile Ser Gly
            195                 200                 205
Ser Gly Val Phe Gly Pro Gly Val Phe Gly Pro Tyr Ala Ser Ala Ala
            210                 215                 220
Ala Ala Ala Gly Pro Gly Val Phe Gly Pro Tyr Gly Pro Gly Ser Ser
225                 230                 235                 240
Ala Ala Ala Ala Ala Gly Ile Tyr Gly Tyr Gly Pro Gly Val Phe Gly
                245                 250                 255
Pro Tyr Gly Pro Gly Ala Ser Gly Ile Asn Gly Pro Gly Ser Gly Ile
            260                 265                 270
Tyr Gly Pro Gly Val Phe Gly Pro Gly Ile Ser Ala Ala Ala Ala Ala
            275                 280                 285
Gly Pro Gly Val Phe Gly Pro Tyr Gly Pro Gly Ala Ser Ala Ala Ala
290                 295                 300
Ala Ala Gly Ile Tyr Gly Pro Gly Val Phe Gly Pro Gly Ile Tyr Gly
305                 310                 315                 320
Pro Gly Ser Ser Gly Pro Gly Val Phe Gly Pro Tyr Gly Pro Gly Ser
                325                 330                 335
Ser Ala Ala Ala Ala Gly Ile Tyr Gly Pro Gly Val Phe Gly Pro
            340                 345                 350
Tyr Gly Pro Gly Ile Ser Ala Ala Ala Ala Gly Ile Tyr Val Phe
            355                 360                 365
Gly Pro Gly Val Phe Gly Pro Tyr Gly Pro Gly Ala Ser Gly Pro Gly
            370                 375                 380
Val Phe Gly Pro Tyr Gly Pro Gly Ala Ser Ala Ala Ala Ala Gly
385                 390                 395                 400
Pro Gly Ile Tyr Gly Pro Gly Val Phe Gly Pro Ser Ala Ser Ala Ala
                405                 410                 415
Ala Ala Ala Gly Ile Tyr Gly Ser Gly Pro Gly Ile Tyr Gly Pro Tyr
            420                 425                 430
Gly Pro Gly Ile Ser Gly Pro Gly Ser Gly Val Phe Gly Ile Gly Pro
            435                 440                 445
```

Tyr Gly Pro Gly Ala Ser Ala Ala Ala Ala Gly Ile Tyr Gly Pro
            450                 455                 460

Gly Val Phe Gly Pro Tyr Gly Pro Gly Ile Ser Ala Ala Ala Ala
465                 470                 475                 480

Gly Pro Gly Ser Gly Ile Tyr Gly Pro Gly Ala Ser Gly Ile Asn Gly
                485                 490                 495

Pro Gly Ser Gly Ile Tyr Gly Pro Gly Val Phe Gly Pro Gly Ile Ser
            500                 505                 510

Ala Ala Ala Ala Gly Ile Tyr Val Phe Gly Pro Gly Val Phe Gly
            515                 520                 525

Pro Tyr Gly Pro Gly Ala Ser Ala Ala Ala Ala Gly Ile Tyr Gly
    530                 535                 540

Ser Gly Pro Gly Val Phe Gly Pro Tyr Gly Pro Gly Ile Ser Gly Ser
545                 550                 555                 560

Gly Val Phe Gly Pro Gly Val Phe Gly Pro Tyr Ala Ser Ala Ala Ala
                565                 570                 575

Ala Ala Gly Pro Gly Ser Gly Val Phe Gly Pro Gly Ala Ser
            580                 585                 590

<210> SEQ ID NO 30
<211> LENGTH: 565
<212> TYPE: PRT
<213> ORGANISM: Artificial Sequence
<220> FEATURE:
<223> OTHER INFORMATION: M_PRT699

<400> SEQUENCE: 30

Met Gly Pro Gly Val Leu Gly Pro Tyr Gly Pro Gly Ala Ser Ala Ala
1               5                   10                  15

Ala Ala Ala Ala Ala Gly Ser Asn Gly Pro Gly Ser Gly Val Leu Gly
                20                  25                  30

Pro Gly Gln Ser Gly Gln Tyr Gly Pro Gly Val Leu Gly Pro Gly Val
            35                  40                  45

Leu Gly Pro Gly Ser Ser Ala Ala Ala Ala Ala Ala Gly Pro Gly
    50                  55                  60

Gln Tyr Gly Pro Gly Val Leu Gly Pro Ser Ala Ser Ala Ala Ala
65                  70                  75                  80

Ala Ala Ala Gly Pro Gly Ser Gly Val Leu Gly Pro Gly Ala Ser Gly
                85                  90                  95

Gln Tyr Gly Pro Gly Val Leu Gly Pro Gly Val Leu Gly Pro Gly Ser
            100                 105                 110

Ser Ala Ala Ala Ala Ala Ala Gly Ser Tyr Gly Ser Gly Pro Gly
        115                 120                 125

Val Leu Gly Pro Tyr Gly Ser Ala Ala Ala Ala Ala Ala Gly Pro
    130                 135                 140

Gly Ser Gly Gln Tyr Gly Gln Gly Pro Tyr Gly Pro Gly Ala Ser Gly
145                 150                 155                 160

Pro Gly Gln Tyr Gly Pro Gly Val Leu Gly Pro Ser Ala Ser Ala Ala
                165                 170                 175

Ala Ala Ala Ala Gly Ser Gly Val Leu Gly Pro Gly Gln Tyr Gly
            180                 185                 190

Pro Tyr Ala Ser Ala Ala Ala Ala Ala Gly Ser Tyr Gly Ser
        195                 200                 205

Gly Pro Gly Val Leu Gly Pro Tyr Gly Pro Gly Gln Ser Gly Ser Gly
    210                 215                 220

```
Val Leu Gly Pro Gly Val Leu Gly Pro Tyr Ala Ser Ala Ala Ala Ala
225                 230                 235                 240

Ala Ala Ala Gly Pro Gly Val Leu Gly Pro Tyr Gly Pro Gly Ser Ser
            245                 250                 255

Ala Ala Ala Ala Ala Ala Ala Gly Ser Tyr Gly Tyr Gly Pro Gly Val
                260                 265                 270

Leu Gly Pro Tyr Gly Pro Gly Ala Ser Gly Gln Asn Gly Pro Gly Ser
            275                 280                 285

Gly Gln Tyr Gly Pro Gly Val Leu Gly Pro Gly Pro Ser Ala Ala Ala
        290                 295                 300

Ala Ala Ala Ala Gly Pro Gly Val Leu Gly Pro Tyr Gly Pro Gly Ala
305                 310                 315                 320

Ser Ala Ala Ala Ala Ala Ala Gly Ser Tyr Gly Pro Gly Val Leu
                325                 330                 335

Gly Pro Gly Gln Tyr Gly Pro Gly Ser Ser Gly Pro Gly Val Leu Gly
                340                 345                 350

Pro Tyr Gly Pro Gly Ser Ser Ala Ala Ala Ala Ala Ala Gly Ser
            355                 360                 365

Tyr Gly Pro Gly Val Leu Gly Pro Tyr Gly Pro Gly Pro Ser Ala Ala
    370                 375                 380

Ala Ala Ala Ala Gly Ser Tyr Val Leu Gly Pro Gly Val Leu Gly
385                 390                 395                 400

Pro Tyr Gly Pro Gly Ala Ser Gly Pro Gly Val Leu Gly Pro Tyr Gly
                405                 410                 415

Pro Gly Ala Ser Ala Ala Ala Ala Ala Ala Gly Pro Gly Gln Tyr
            420                 425                 430

Gly Pro Gly Val Leu Gly Pro Ser Ala Ser Ala Ala Ala Ala Ala
        435                 440                 445

Ala Gly Ser Tyr Gly Ser Gly Pro Gly Gln Tyr Gly Pro Tyr Gly Pro
    450                 455                 460

Gly Gln Ser Gly Pro Gly Ser Gly Val Leu Gly Gln Gly Pro Tyr Gly
465                 470                 475                 480

Pro Gly Ala Ser Ala Ala Ala Ala Ala Ala Gly Ser Tyr Gly Pro
            485                 490                 495

Gly Val Leu Gly Pro Tyr Gly Pro Gly Ser Ala Ala Ala Ala
        500                 505                 510

Ala Ala Gly Pro Gly Ser Gly Gln Tyr Gly Pro Gly Ala Ser Gly Gln
    515                 520                 525

Asn Gly Pro Gly Ser Gly Gln Tyr Gly Pro Gly Val Leu Gly Pro Gly
        530                 535                 540

Pro Ser Ala Ala Ala Ala Ala Ala Gly Pro Gly Ser Gly Val Leu
545                 550                 555                 560

Gly Pro Gly Ala Ser
                565

<210> SEQ ID NO 31
<211> LENGTH: 565
<212> TYPE: PRT
<213> ORGANISM: Artificial Sequence
<220> FEATURE:
<223> OTHER INFORMATION: M_PRT698

<400> SEQUENCE: 31

Met Gly Pro Gly Val Leu Gly Pro Tyr Gly Pro Gly Ala Ser Ala Ala
1               5                   10                  15
```

Ala Ala Ala Ala Ala Gly Ser Asn Gly Pro Ser Gly Val Leu Gly
                20                  25                  30

Pro Gly Ile Ser Gly Ile Tyr Gly Pro Gly Val Leu Gly Pro Gly Val
            35                  40                  45

Leu Gly Pro Gly Ser Ser Ala Ala Ala Ala Ala Ala Gly Pro Gly
50                  55                  60

Ile Tyr Gly Pro Gly Val Leu Gly Pro Ser Ala Ser Ala Ala Ala
65              70                  75                  80

Ala Ala Ala Gly Pro Gly Ser Gly Val Leu Gly Pro Gly Ala Ser Gly
                85                  90                  95

Ile Tyr Gly Pro Gly Val Leu Gly Pro Gly Val Leu Gly Pro Gly Ser
            100                 105                 110

Ser Ala Ala Ala Ala Ala Ala Ala Gly Ser Tyr Gly Ser Gly Pro Gly
        115                 120                 125

Val Leu Gly Pro Tyr Gly Ser Ala Ala Ala Ala Ala Ala Gly Pro
    130                 135                 140

Gly Ser Gly Ile Tyr Gly Ile Gly Pro Tyr Gly Pro Gly Ala Ser Gly
145                 150                 155                 160

Pro Gly Ile Tyr Gly Pro Gly Val Leu Gly Pro Ser Ala Ser Ala Ala
            165                 170                 175

Ala Ala Ala Ala Ala Gly Ser Gly Val Leu Gly Pro Gly Ile Tyr Gly
        180                 185                 190

Pro Tyr Ala Ser Ala Ala Ala Ala Ala Ala Gly Ser Tyr Gly Ser
    195                 200                 205

Gly Pro Gly Val Leu Gly Pro Tyr Gly Pro Gly Ile Ser Gly Ser Gly
210                 215                 220

Val Leu Gly Pro Gly Val Leu Gly Pro Tyr Ala Ser Ala Ala Ala Ala
225                 230                 235                 240

Ala Ala Ala Gly Pro Gly Val Leu Gly Pro Tyr Gly Pro Gly Ser Ser
            245                 250                 255

Ala Ala Ala Ala Ala Ala Ala Gly Ser Tyr Gly Tyr Gly Pro Gly Val
        260                 265                 270

Leu Gly Pro Tyr Gly Pro Gly Ala Ser Gly Ile Asn Gly Pro Gly Ser
    275                 280                 285

Gly Ile Tyr Gly Pro Gly Val Leu Gly Pro Gly Pro Ser Ala Ala Ala
    290                 295                 300

Ala Ala Ala Gly Pro Gly Val Leu Gly Pro Tyr Gly Pro Gly Ala
305                 310                 315                 320

Ser Ala Ala Ala Ala Ala Ala Ala Gly Ser Tyr Gly Pro Gly Val Leu
            325                 330                 335

Gly Pro Gly Ile Tyr Gly Pro Gly Ser Ser Gly Pro Gly Val Leu Gly
            340                 345                 350

Pro Tyr Gly Pro Gly Ser Ser Ala Ala Ala Ala Ala Ala Gly Ser
    355                 360                 365

Tyr Gly Pro Gly Val Leu Gly Pro Tyr Gly Pro Gly Pro Ser Ala Ala
    370                 375                 380

Ala Ala Ala Ala Ala Gly Ser Tyr Val Leu Gly Pro Gly Val Leu Gly
385                 390                 395                 400

Pro Tyr Gly Pro Gly Ala Ser Gly Pro Gly Val Leu Gly Pro Tyr Gly
            405                 410                 415

Pro Gly Ala Ser Ala Ala Ala Ala Ala Ala Gly Pro Gly Ile Tyr
    420                 425                 430

Gly Pro Gly Val Leu Gly Pro Ser Ala Ser Ala Ala Ala Ala Ala Ala

-continued

```
                435                 440                 445
Ala Gly Ser Tyr Gly Ser Gly Pro Gly Ile Tyr Gly Pro Tyr Gly Pro
            450                 455                 460
Gly Ile Ser Gly Pro Gly Ser Gly Val Leu Gly Ile Gly Pro Tyr Gly
465                 470                 475                 480
Pro Gly Ala Ser Ala Ala Ala Ala Ala Gly Ser Tyr Gly Pro
                485                 490                 495
Gly Val Leu Gly Pro Tyr Gly Pro Gly Pro Ser Ala Ala Ala Ala
            500                 505                 510
Ala Ala Gly Pro Gly Ser Gly Ile Tyr Gly Pro Gly Ala Ser Gly Ile
            515                 520                 525
Asn Gly Pro Gly Ser Gly Ile Tyr Gly Pro Gly Val Leu Gly Pro Gly
            530                 535                 540
Pro Ser Ala Ala Ala Ala Ala Ala Gly Pro Gly Ser Gly Val Leu
545                 550                 555                 560
Gly Pro Gly Ala Ser
                565
```

<210> SEQ ID NO 32
<211> LENGTH: 1179
<212> TYPE: PRT
<213> ORGANISM: Artificial Sequence
<220> FEATURE:
<223> OTHER INFORMATION: Met-PRT966

<400> SEQUENCE: 32

```
Met Gly Pro Gly Val Phe Gly Pro Tyr Gly Pro Gly Ala Ser Ala Ala
1               5                   10                  15
Ala Ala Ala Gly Ile Asn Gly Pro Gly Ser Gly Val Phe Gly Pro Gly
            20                  25                  30
Ile Ser Gly Ile Tyr Gly Pro Gly Val Phe Gly Pro Gly Val Phe Gly
            35                  40                  45
Pro Gly Ser Ser Ala Ala Ala Ala Ala Gly Pro Gly Ile Tyr Gly Pro
        50                  55                  60
Gly Val Phe Gly Pro Ser Ala Ser Ala Ala Ala Ala Gly Pro Gly
65                  70                  75                  80
Ser Gly Val Phe Gly Pro Gly Ala Ser Gly Ile Tyr Gly Pro Gly Val
                85                  90                  95
Phe Gly Pro Gly Val Phe Gly Pro Gly Ser Ser Ala Ala Ala Ala
            100                 105                 110
Gly Ile Tyr Gly Ser Gly Pro Gly Val Phe Gly Pro Tyr Gly Ser Ala
            115                 120                 125
Ala Ala Ala Gly Pro Gly Ser Gly Ile Tyr Gly Ile Gly Pro Tyr
        130                 135                 140
Gly Pro Gly Ala Ser Gly Pro Gly Ile Tyr Gly Pro Gly Val Phe Gly
145                 150                 155                 160
Pro Ser Ala Ser Ala Ala Ala Ala Gly Ser Gly Val Phe Gly Pro
            165                 170                 175
Gly Ile Tyr Gly Pro Tyr Ala Ser Ala Ala Ala Ala Gly Ile Tyr
            180                 185                 190
Gly Ser Gly Pro Gly Val Phe Gly Pro Tyr Gly Pro Gly Ile Ser Gly
            195                 200                 205
Ser Gly Val Phe Gly Pro Gly Val Phe Gly Pro Tyr Ala Ser Ala Ala
            210                 215                 220
Ala Ala Ala Gly Pro Gly Val Phe Gly Pro Tyr Gly Pro Gly Ser Ser
```

```
                225                 230                 235                 240
Ala Ala Ala Ala Ala Gly Ile Tyr Gly Tyr Gly Pro Gly Val Phe Gly
                245                 250                 255
Pro Tyr Gly Pro Gly Ala Ser Gly Ile Asn Gly Pro Gly Ser Gly Ile
                260                 265                 270
Tyr Gly Pro Gly Val Phe Gly Pro Gly Ile Ser Ala Ala Ala Ala Ala
                275                 280                 285
Gly Pro Gly Val Phe Gly Pro Tyr Gly Pro Gly Ala Ser Ala Ala Ala
                290                 295                 300
Ala Ala Gly Ile Tyr Gly Pro Gly Val Phe Gly Pro Gly Ile Tyr Gly
305                 310                 315                 320
Pro Gly Ser Ser Gly Pro Gly Val Phe Gly Pro Tyr Gly Pro Gly Ser
                325                 330                 335
Ser Ala Ala Ala Ala Gly Ile Tyr Gly Pro Gly Val Phe Gly Pro
                340                 345                 350
Tyr Gly Pro Gly Ile Ser Ala Ala Ala Ala Gly Ile Tyr Val Phe
                355                 360                 365
Gly Pro Gly Val Phe Gly Pro Tyr Gly Pro Gly Ala Ser Gly Pro Gly
                370                 375                 380
Val Phe Gly Pro Tyr Gly Pro Gly Ala Ser Ala Ala Ala Ala Gly
385                 390                 395                 400
Pro Gly Ile Tyr Gly Pro Gly Val Phe Gly Pro Ser Ala Ser Ala Ala
                405                 410                 415
Ala Ala Ala Gly Ile Tyr Gly Ser Gly Pro Gly Ile Tyr Gly Pro Tyr
                420                 425                 430
Gly Pro Gly Ile Ser Gly Pro Gly Ser Gly Val Phe Gly Ile Gly Pro
                435                 440                 445
Tyr Gly Pro Gly Ala Ser Ala Ala Ala Ala Gly Ile Tyr Gly Pro
                450                 455                 460
Gly Val Phe Gly Pro Tyr Gly Pro Gly Ile Ser Ala Ala Ala Ala
465                 470                 475                 480
Gly Pro Gly Ser Gly Ile Tyr Gly Pro Gly Ala Ser Gly Ile Asn Gly
                485                 490                 495
Pro Gly Ser Gly Ile Tyr Gly Pro Gly Val Phe Gly Pro Gly Ile Ser
                500                 505                 510
Ala Ala Ala Ala Ala Gly Ile Tyr Val Phe Gly Pro Gly Val Phe Gly
                515                 520                 525
Pro Tyr Gly Pro Gly Ala Ser Ala Ala Ala Ala Gly Ile Tyr Gly
                530                 535                 540
Ser Gly Pro Gly Val Phe Gly Pro Tyr Gly Pro Gly Ile Ser Gly Ser
545                 550                 555                 560
Gly Val Phe Gly Pro Gly Val Phe Gly Pro Tyr Ala Ser Ala Ala Ala
                565                 570                 575
Ala Ala Gly Pro Gly Ser Gly Val Phe Gly Pro Gly Ala Ser Gly Pro
                580                 585                 590
Gly Val Phe Gly Pro Tyr Gly Pro Gly Ala Ser Ala Ala Ala Ala
                595                 600                 605
Gly Ile Asn Gly Pro Gly Ser Gly Val Phe Gly Pro Gly Ile Ser Gly
                610                 615                 620
Ile Tyr Gly Pro Gly Val Phe Gly Pro Gly Val Phe Gly Pro Gly Ser
625                 630                 635                 640
Ser Ala Ala Ala Ala Ala Gly Pro Gly Ile Tyr Gly Pro Gly Val Phe
                645                 650                 655
```

-continued

Gly Pro Ser Ala Ser Ala Ala Ala Ala Gly Pro Gly Ser Gly Val
            660                 665                 670

Phe Gly Pro Gly Ala Ser Gly Ile Tyr Gly Pro Gly Val Phe Gly Pro
            675                 680                 685

Gly Val Phe Gly Pro Gly Ser Ser Ala Ala Ala Ala Gly Ile Tyr
    690                 695                 700

Gly Ser Gly Pro Gly Val Phe Gly Pro Tyr Gly Ser Ala Ala Ala
705                 710                 715                 720

Ala Gly Pro Gly Ser Gly Ile Tyr Gly Ile Gly Pro Tyr Gly Pro Gly
            725                 730                 735

Ala Ser Gly Pro Gly Ile Tyr Gly Pro Gly Val Phe Gly Pro Ser Ala
            740                 745                 750

Ser Ala Ala Ala Ala Gly Ser Gly Val Phe Gly Pro Gly Ile Tyr
    755                 760                 765

Gly Pro Tyr Ala Ser Ala Ala Ala Ala Gly Ile Tyr Gly Ser Gly
    770                 775                 780

Pro Gly Val Phe Gly Pro Tyr Gly Pro Gly Ile Ser Gly Ser Gly Val
785                 790                 795                 800

Phe Gly Pro Gly Val Phe Gly Pro Tyr Ala Ser Ala Ala Ala Ala
            805                 810                 815

Gly Pro Gly Val Phe Gly Pro Tyr Gly Pro Gly Ser Ser Ala Ala Ala
            820                 825                 830

Ala Ala Gly Ile Tyr Gly Tyr Gly Pro Gly Val Phe Gly Pro Tyr Gly
            835                 840                 845

Pro Gly Ala Ser Gly Ile Asn Gly Pro Gly Ser Gly Ile Tyr Gly Pro
            850                 855                 860

Gly Val Phe Gly Pro Gly Ile Ser Ala Ala Ala Ala Gly Pro Gly
865                 870                 875                 880

Val Phe Gly Pro Tyr Gly Pro Gly Ala Ser Ala Ala Ala Ala Gly
            885                 890                 895

Ile Tyr Gly Pro Gly Val Phe Gly Pro Gly Ile Tyr Gly Pro Gly Ser
            900                 905                 910

Ser Gly Pro Gly Val Phe Gly Pro Tyr Gly Pro Gly Ser Ser Ala Ala
            915                 920                 925

Ala Ala Ala Gly Ile Tyr Gly Pro Gly Val Phe Gly Pro Tyr Gly Pro
            930                 935                 940

Gly Ile Ser Ala Ala Ala Ala Gly Ile Tyr Val Phe Gly Pro Gly
945                 950                 955                 960

Val Phe Gly Pro Tyr Gly Pro Gly Ala Ser Gly Pro Gly Val Phe Gly
            965                 970                 975

Pro Tyr Gly Pro Gly Ala Ser Ala Ala Ala Ala Gly Pro Gly Ile
            980                 985                 990

Tyr Gly Pro Gly Val Phe Gly Pro Ser Ala Ser Ala Ala Ala Ala Ala
            995                1000                1005

Gly Ile Tyr Gly Ser Gly Pro Gly Ile Tyr Gly Pro Tyr Gly Pro
    1010                1015                1020

Gly Ile Ser Gly Pro Gly Ser Gly Val Phe Gly Ile Gly Pro Tyr
    1025                1030                1035

Gly Pro Gly Ala Ser Ala Ala Ala Ala Ala Gly Ile Tyr Gly Pro
    1040                1045                1050

Gly Val Phe Gly Pro Tyr Gly Pro Gly Ile Ser Ala Ala Ala Ala
    1055                1060                1065

```
Ala Gly Pro Gly Ser Gly Ile Tyr Gly Pro Gly Ala Ser Gly Ile
    1070                1075                1080

Asn Gly Pro Gly Ser Gly Ile Tyr Gly Pro Gly Val Phe Gly Pro
    1085                1090                1095

Gly Ile Ser Ala Ala Ala Ala Gly Ile Tyr Val Phe Gly Pro
    1100                1105                1110

Gly Val Phe Gly Pro Tyr Gly Pro Gly Ala Ser Ala Ala Ala Ala
    1115                1120                1125

Ala Gly Ile Tyr Gly Ser Gly Pro Gly Val Phe Gly Pro Tyr Gly
    1130                1135                1140

Pro Gly Ile Ser Gly Ser Gly Val Phe Gly Pro Gly Val Phe Gly
    1145                1150                1155

Pro Tyr Ala Ser Ala Ala Ala Ala Gly Pro Gly Ser Gly Val
    1160                1165                1170

Phe Gly Pro Gly Ala Ser
    1175
```

<210> SEQ ID NO 33
<211> LENGTH: 601
<212> TYPE: PRT
<213> ORGANISM: Artificial Sequence
<220> FEATURE:
<223> OTHER INFORMATION: PRT888

<400> SEQUENCE: 33

```
Met His His His His His Ser Ser Gly Ser Gly Pro Gly Val
1               5                   10                  15

Leu Gly Pro Tyr Gly Pro Gly Ala Ser Ala Ala Ala Ala Gly Gln
            20                  25                  30

Asn Gly Pro Gly Ser Gly Val Leu Gly Pro Gly Gln Ser Gly Gln Tyr
            35                  40                  45

Gly Pro Gly Val Leu Gly Pro Gly Val Leu Gly Pro Gly Ser Ser Ala
        50                  55                  60

Ala Ala Ala Gly Pro Gly Gln Tyr Gly Pro Gly Val Leu Gly Pro
65                  70                  75                  80

Ser Ala Ser Ala Ala Ala Ala Gly Pro Gly Ser Gly Val Leu Gly
                85                  90                  95

Pro Gly Ala Ser Gly Gln Tyr Gly Pro Gly Val Leu Gly Pro Gly Val
                100                 105                 110

Leu Gly Pro Gly Ser Ser Ala Ala Ala Ala Gly Gln Tyr Gly Ser
            115                 120                 125

Gly Pro Gly Val Leu Gly Pro Tyr Gly Ser Ala Ala Ala Ala Gly
    130                 135                 140

Pro Gly Ser Gly Gln Tyr Gly Gln Gly Pro Tyr Gly Pro Gly Ala Ser
145                 150                 155                 160

Gly Pro Gly Gln Tyr Gly Pro Gly Val Leu Gly Pro Ser Ala Ser Ala
                165                 170                 175

Ala Ala Ala Gly Ser Gly Val Leu Gly Pro Gly Gln Tyr Gly Pro
            180                 185                 190

Tyr Ala Ser Ala Ala Ala Ala Gly Gln Tyr Gly Ser Gly Pro Gly
            195                 200                 205

Val Leu Gly Pro Tyr Gly Pro Gly Gln Ser Gly Ser Gly Val Leu Gly
        210                 215                 220

Pro Gly Val Leu Gly Pro Tyr Ala Ser Ala Ala Ala Ala Gly Pro
225                 230                 235                 240
```

Gly Val Leu Gly Pro Tyr Gly Pro Gly Ser Ala Ala Ala Ala
             245                 250                 255

Gly Gln Tyr Gly Tyr Gly Pro Gly Val Leu Gly Pro Tyr Gly Pro Gly
        260                 265                 270

Ala Ser Gly Gln Asn Gly Pro Gly Ser Gly Gln Tyr Gly Pro Gly Val
        275                 280                 285

Leu Gly Pro Gly Gln Ser Ala Ala Ala Ala Gly Pro Gly Val Leu
        290                 295                 300

Gly Pro Tyr Gly Pro Gly Ala Ser Ala Ala Ala Ala Gly Gln Tyr
305                 310                 315                 320

Gly Pro Gly Val Leu Gly Pro Gly Gln Tyr Gly Pro Gly Ser Ser Gly
                325                 330                 335

Pro Gly Val Leu Gly Pro Tyr Gly Pro Gly Ser Ser Ala Ala Ala Ala
                340                 345                 350

Ala Gly Gln Tyr Gly Pro Gly Val Leu Gly Pro Tyr Gly Pro Gly Gln
            355                 360                 365

Ser Ala Ala Ala Ala Gly Gln Tyr Val Leu Gly Pro Gly Val Leu
        370                 375                 380

Gly Pro Tyr Gly Pro Gly Ala Ser Gly Pro Gly Val Leu Gly Pro Tyr
385                 390                 395                 400

Gly Pro Gly Ala Ser Ala Ala Ala Ala Gly Pro Gly Gln Tyr Gly
                405                 410                 415

Pro Gly Val Leu Gly Pro Ser Ala Ser Ala Ala Ala Ala Gly Gln
                420                 425                 430

Tyr Gly Ser Gly Pro Gly Gln Tyr Gly Pro Tyr Gly Pro Gly Gln Ser
        435                 440                 445

Gly Pro Gly Ser Gly Val Leu Gly Gln Gly Pro Tyr Gly Pro Gly Ala
450                 455                 460

Ser Ala Ala Ala Ala Gly Gln Tyr Gly Pro Gly Val Leu Gly Pro
465                 470                 475                 480

Tyr Gly Pro Gly Gln Ser Ala Ala Ala Ala Gly Pro Gly Ser Gly
                485                 490                 495

Gln Tyr Gly Pro Gly Ala Ser Gly Gln Asn Gly Pro Gly Ser Gly Gln
        500                 505                 510

Tyr Gly Pro Gly Val Leu Gly Pro Gly Gln Ser Ala Ala Ala Ala
        515                 520                 525

Gly Gln Tyr Val Leu Gly Pro Gly Val Leu Gly Pro Tyr Gly Pro Gly
        530                 535                 540

Ala Ser Ala Ala Ala Ala Gly Gln Tyr Gly Ser Gly Pro Gly Val
545                 550                 555                 560

Leu Gly Pro Tyr Gly Pro Gly Gln Ser Gly Ser Gly Val Leu Gly Pro
                565                 570                 575

Gly Val Leu Gly Pro Tyr Ala Ser Ala Ala Ala Ala Gly Pro Gly
        580                 585                 590

Ser Gly Val Leu Gly Pro Gly Ala Ser
        595                 600

<210> SEQ ID NO 34
<211> LENGTH: 601
<212> TYPE: PRT
<213> ORGANISM: Artificial Sequence
<220> FEATURE:
<223> OTHER INFORMATION: PRT965

<400> SEQUENCE: 34

```
Met His His His His His Ser Ser Gly Ser Ser Gly Pro Gly Thr
1               5                   10                  15

Ser Gly Pro Tyr Gly Pro Gly Ala Ser Ala Ala Ala Ala Gly Ala
            20                  25                  30

Asn Gly Pro Gly Ser Gly Thr Ser Gly Pro Gly Ala Ser Gly Ala Tyr
            35                  40                  45

Gly Pro Gly Thr Ser Gly Pro Gly Thr Ser Gly Pro Gly Ser Ser Ala
50                  55                  60

Ala Ala Ala Ala Gly Pro Gly Ala Tyr Gly Pro Gly Thr Ser Gly Pro
65                  70                  75                  80

Ser Ala Ser Ala Ala Ala Ala Gly Pro Gly Ser Gly Thr Ser Gly
                85                  90                  95

Pro Gly Ala Ser Gly Ala Tyr Gly Pro Gly Thr Ser Gly Pro Gly Thr
            100                 105                 110

Ser Gly Pro Gly Ser Ser Ala Ala Ala Ala Gly Ala Tyr Gly Ser
            115                 120                 125

Gly Pro Gly Thr Ser Gly Pro Tyr Gly Ser Ala Ala Ala Ala Gly
            130                 135                 140

Pro Gly Ser Gly Ala Tyr Gly Ala Gly Pro Tyr Gly Pro Gly Ala Ser
145                 150                 155                 160

Gly Pro Gly Ala Tyr Gly Pro Gly Thr Ser Gly Pro Ser Ala Ser Ala
            165                 170                 175

Ala Ala Ala Gly Ser Gly Thr Ser Gly Pro Gly Ala Tyr Gly Pro
            180                 185                 190

Tyr Ala Ser Ala Ala Ala Ala Gly Ala Tyr Gly Ser Gly Pro Gly
            195                 200                 205

Thr Ser Gly Pro Tyr Gly Pro Gly Ala Ser Gly Ser Gly Thr Ser Gly
210                 215                 220

Pro Gly Thr Ser Gly Pro Tyr Ala Ser Ala Ala Ala Ala Gly Pro
225                 230                 235                 240

Gly Thr Ser Gly Pro Tyr Gly Pro Gly Ser Ser Ala Ala Ala Ala
            245                 250                 255

Gly Ala Tyr Gly Tyr Gly Pro Gly Thr Ser Gly Pro Tyr Gly Pro Gly
            260                 265                 270

Ala Ser Gly Ala Asn Gly Pro Gly Ser Gly Ala Tyr Gly Pro Gly Thr
            275                 280                 285

Ser Gly Pro Gly Ala Ser Ala Ala Ala Ala Gly Pro Gly Thr Ser
            290                 295                 300

Gly Pro Tyr Gly Pro Gly Ala Ser Ala Ala Ala Ala Gly Ala Tyr
305                 310                 315                 320

Gly Pro Gly Thr Ser Gly Pro Gly Ala Tyr Gly Pro Gly Ser Ser Gly
            325                 330                 335

Pro Gly Thr Ser Gly Pro Tyr Gly Pro Gly Ser Ser Ala Ala Ala
            340                 345                 350

Ala Gly Ala Tyr Gly Pro Gly Thr Ser Gly Pro Tyr Gly Pro Gly Ala
            355                 360                 365

Ser Ala Ala Ala Ala Gly Ala Tyr Thr Ser Gly Pro Gly Thr Ser
            370                 375                 380

Gly Pro Tyr Gly Pro Gly Ala Ser Gly Pro Gly Thr Ser Gly Pro Tyr
385                 390                 395                 400

Gly Pro Gly Ala Ser Ala Ala Ala Ala Gly Pro Gly Ala Tyr Gly
            405                 410                 415

Pro Gly Thr Ser Gly Pro Ser Ala Ser Ala Ala Ala Ala Gly Ala
```

```
                420                 425                 430
Tyr Gly Ser Gly Pro Gly Ala Tyr Gly Pro Tyr Gly Pro Gly Ala Ser
            435                 440                 445

Gly Pro Gly Ser Gly Thr Ser Gly Ala Gly Pro Tyr Gly Pro Gly Ala
        450                 455                 460

Ser Ala Ala Ala Ala Gly Ala Tyr Gly Pro Gly Thr Ser Gly Pro
465                 470                 475                 480

Tyr Gly Pro Gly Ala Ser Ala Ala Ala Ala Gly Pro Gly Ser Gly
                485                 490                 495

Ala Tyr Gly Pro Gly Ala Ser Gly Ala Asn Gly Pro Gly Ser Gly Ala
            500                 505                 510

Tyr Gly Pro Gly Thr Ser Gly Pro Gly Ala Ser Ala Ala Ala Ala
        515                 520                 525

Gly Ala Tyr Thr Ser Gly Pro Gly Thr Ser Gly Pro Tyr Gly Pro Gly
    530                 535                 540

Ala Ser Ala Ala Ala Ala Gly Ala Tyr Gly Ser Gly Pro Gly Thr
545                 550                 555                 560

Ser Gly Pro Tyr Gly Pro Gly Ala Ser Gly Ser Gly Thr Ser Gly Pro
                565                 570                 575

Gly Thr Ser Gly Pro Tyr Ala Ser Ala Ala Ala Ala Gly Pro Gly
            580                 585                 590

Ser Gly Thr Ser Gly Pro Gly Ala Ser
        595                 600

<210> SEQ ID NO 35
<211> LENGTH: 601
<212> TYPE: PRT
<213> ORGANISM: Artificial Sequence
<220> FEATURE:
<223> OTHER INFORMATION: PRT889

<400> SEQUENCE: 35

Met His His His His His Ser Ser Gly Ser Ser Gly Pro Gly Val
1               5                   10                  15

Leu Gly Pro Tyr Gly Pro Gly Ala Ser Ala Ala Ala Ala Gly Ile
            20                  25                  30

Asn Gly Pro Gly Ser Gly Val Leu Gly Pro Gly Ile Ser Gly Ile Tyr
        35                  40                  45

Gly Pro Gly Val Leu Gly Pro Gly Val Leu Gly Pro Gly Ser Ser Ala
    50                  55                  60

Ala Ala Ala Ala Gly Pro Gly Ile Tyr Gly Pro Gly Val Leu Gly Pro
65                  70                  75                  80

Ser Ala Ser Ala Ala Ala Ala Gly Pro Gly Ser Gly Val Leu Gly
                85                  90                  95

Pro Gly Ala Ser Gly Ile Tyr Gly Pro Gly Val Leu Gly Pro Gly Val
            100                 105                 110

Leu Gly Pro Gly Ser Ser Ala Ala Ala Ala Gly Ile Tyr Gly Ser
        115                 120                 125

Gly Pro Gly Val Leu Gly Pro Tyr Gly Ser Ala Ala Ala Ala Gly
    130                 135                 140

Pro Gly Ser Gly Ile Tyr Gly Ile Gly Pro Tyr Gly Pro Gly Ala Ser
145                 150                 155                 160

Gly Pro Gly Ile Tyr Gly Pro Gly Val Leu Gly Pro Ser Ala Ser Ala
                165                 170                 175

Ala Ala Ala Gly Ser Gly Val Leu Gly Pro Gly Ile Tyr Gly Pro
```

```
            180                 185                 190
Tyr Ala Ser Ala Ala Ala Ala Gly Ile Tyr Gly Ser Gly Pro Gly
        195                 200                 205
Val Leu Gly Pro Tyr Gly Pro Gly Ile Ser Gly Ser Gly Val Leu Gly
    210                 215                 220
Pro Gly Val Leu Gly Pro Tyr Ala Ser Ala Ala Ala Ala Gly Pro
225                 230                 235                 240
Gly Val Leu Gly Pro Tyr Gly Pro Gly Ser Ser Ala Ala Ala Ala
                245                 250                 255
Gly Ile Tyr Gly Tyr Gly Pro Gly Val Leu Gly Pro Tyr Gly Pro Gly
            260                 265                 270
Ala Ser Gly Ile Asn Gly Pro Gly Ser Gly Ile Tyr Gly Pro Gly Val
        275                 280                 285
Leu Gly Pro Gly Ile Ser Ala Ala Ala Ala Gly Pro Gly Val Leu
    290                 295                 300
Gly Pro Tyr Gly Pro Gly Ala Ser Ala Ala Ala Ala Gly Ile Tyr
305                 310                 315                 320
Gly Pro Gly Val Leu Gly Pro Gly Ile Tyr Gly Pro Gly Ser Ser Gly
                325                 330                 335
Pro Gly Val Leu Gly Pro Tyr Gly Pro Gly Ser Ser Ala Ala Ala Ala
            340                 345                 350
Ala Gly Ile Tyr Gly Pro Gly Val Leu Gly Pro Tyr Gly Pro Gly Ile
        355                 360                 365
Ser Ala Ala Ala Ala Gly Ile Tyr Val Leu Gly Pro Gly Val Leu
    370                 375                 380
Gly Pro Tyr Gly Pro Gly Ala Ser Gly Pro Gly Val Leu Gly Pro Tyr
385                 390                 395                 400
Gly Pro Gly Ala Ser Ala Ala Ala Ala Gly Pro Gly Ile Tyr Gly
                405                 410                 415
Pro Gly Val Leu Gly Pro Ser Ala Ser Ala Ala Ala Ala Gly Ile
            420                 425                 430
Tyr Gly Ser Gly Pro Gly Ile Tyr Gly Pro Tyr Gly Pro Gly Ile Ser
        435                 440                 445
Gly Pro Gly Ser Gly Val Leu Gly Ile Gly Pro Tyr Gly Pro Gly Ala
    450                 455                 460
Ser Ala Ala Ala Ala Gly Ile Tyr Gly Pro Gly Val Leu Gly Pro
465                 470                 475                 480
Tyr Gly Pro Gly Ile Ser Ala Ala Ala Ala Gly Pro Gly Ser Gly
                485                 490                 495
Ile Tyr Gly Pro Gly Ala Ser Gly Ile Asn Gly Pro Gly Ser Gly Ile
            500                 505                 510
Tyr Gly Pro Gly Val Leu Gly Pro Gly Ile Ser Ala Ala Ala Ala
        515                 520                 525
Gly Ile Tyr Val Leu Gly Pro Gly Val Leu Gly Pro Tyr Gly Pro Gly
    530                 535                 540
Ala Ser Ala Ala Ala Ala Gly Ile Tyr Gly Ser Gly Pro Gly Val
545                 550                 555                 560
Leu Gly Pro Tyr Gly Pro Gly Ile Ser Gly Ser Gly Val Leu Gly Pro
                565                 570                 575
Gly Val Leu Gly Pro Tyr Ala Ser Ala Ala Ala Ala Gly Pro Gly
            580                 585                 590
Ser Gly Val Leu Gly Pro Gly Ala Ser
        595                 600
```

<210> SEQ ID NO 36
<211> LENGTH: 601
<212> TYPE: PRT
<213> ORGANISM: Artificial Sequence
<220> FEATURE:
<223> OTHER INFORMATION: PRT916

<400> SEQUENCE: 36

```
Met His His His His His Ser Ser Gly Ser Gly Pro Gly Val
1               5                   10                  15

Ile Gly Pro Tyr Gly Pro Gly Ala Ser Ala Ala Ala Ala Gly Leu
            20                  25                  30

Asn Gly Pro Gly Ser Gly Val Ile Gly Pro Gly Leu Ser Gly Leu Tyr
            35                  40                  45

Gly Pro Gly Val Ile Gly Pro Gly Val Ile Gly Pro Ser Ser Ala
            50                  55                  60

Ala Ala Ala Ala Gly Pro Gly Leu Tyr Gly Pro Gly Val Ile Gly Pro
65                  70                  75                  80

Ser Ala Ser Ala Ala Ala Ala Gly Pro Gly Ser Gly Val Ile Gly
                    85                  90                  95

Pro Gly Ala Ser Gly Leu Tyr Gly Pro Gly Val Ile Gly Pro Gly Val
                100                 105                 110

Ile Gly Pro Gly Ser Ser Ala Ala Ala Ala Gly Leu Tyr Gly Ser
            115                 120                 125

Gly Pro Gly Val Ile Gly Pro Tyr Gly Ser Ala Ala Ala Ala Gly
            130                 135                 140

Pro Gly Ser Gly Leu Tyr Gly Leu Gly Pro Tyr Gly Pro Gly Ala Ser
145                 150                 155                 160

Gly Pro Gly Leu Tyr Gly Pro Gly Val Ile Gly Pro Ser Ala Ser Ala
                165                 170                 175

Ala Ala Ala Ala Gly Ser Gly Val Ile Gly Pro Gly Leu Tyr Gly Pro
                180                 185                 190

Tyr Ala Ser Ala Ala Ala Ala Gly Leu Tyr Gly Ser Gly Pro Gly
            195                 200                 205

Val Ile Gly Pro Tyr Gly Pro Gly Leu Ser Gly Ser Gly Val Ile Gly
            210                 215                 220

Pro Gly Val Ile Gly Pro Tyr Ala Ser Ala Ala Ala Ala Gly Pro
225                 230                 235                 240

Gly Val Ile Gly Pro Tyr Gly Pro Gly Ser Ser Ala Ala Ala Ala
                245                 250                 255

Gly Leu Tyr Gly Tyr Gly Pro Gly Val Ile Gly Pro Tyr Gly Pro Gly
            260                 265                 270

Ala Ser Gly Leu Asn Gly Pro Gly Ser Gly Leu Tyr Gly Pro Gly Val
                275                 280                 285

Ile Gly Pro Gly Leu Ser Ala Ala Ala Ala Gly Pro Gly Val Ile
            290                 295                 300

Gly Pro Tyr Gly Pro Gly Ala Ser Ala Ala Ala Ala Gly Leu Tyr
305                 310                 315                 320

Gly Pro Gly Val Ile Gly Pro Gly Leu Tyr Gly Pro Gly Ser Ser Gly
                325                 330                 335

Pro Gly Val Ile Gly Pro Tyr Gly Pro Gly Ser Ser Ala Ala Ala Ala
                340                 345                 350

Ala Gly Leu Tyr Gly Pro Gly Val Ile Gly Pro Tyr Gly Pro Gly Leu
            355                 360                 365
```

Ser Ala Ala Ala Ala Gly Leu Tyr Val Ile Gly Pro Gly Val Ile
    370                 375                 380

Gly Pro Tyr Gly Pro Gly Ala Ser Gly Pro Gly Val Ile Gly Pro Tyr
385                 390                 395                 400

Gly Pro Gly Ala Ser Ala Ala Ala Ala Gly Pro Gly Leu Tyr Gly
                405                 410                 415

Pro Gly Val Ile Gly Pro Ser Ala Ser Ala Ala Ala Ala Gly Leu
            420                 425                 430

Tyr Gly Ser Gly Pro Gly Leu Tyr Gly Pro Tyr Gly Pro Gly Leu Ser
        435                 440                 445

Gly Pro Gly Ser Gly Val Ile Gly Leu Gly Pro Tyr Gly Pro Gly Ala
    450                 455                 460

Ser Ala Ala Ala Ala Gly Leu Tyr Gly Pro Gly Val Ile Gly Pro
465                 470                 475                 480

Tyr Gly Pro Gly Leu Ser Ala Ala Ala Ala Gly Pro Gly Ser Gly
                485                 490                 495

Leu Tyr Gly Pro Gly Ala Ser Gly Leu Asn Gly Pro Gly Ser Gly Leu
            500                 505                 510

Tyr Gly Pro Gly Val Ile Gly Pro Gly Leu Ser Ala Ala Ala Ala
        515                 520                 525

Gly Leu Tyr Val Ile Gly Pro Gly Val Ile Gly Pro Tyr Gly Pro Gly
    530                 535                 540

Ala Ser Ala Ala Ala Ala Gly Leu Tyr Gly Ser Gly Pro Gly Val
545                 550                 555                 560

Ile Gly Pro Tyr Gly Pro Gly Leu Ser Gly Ser Gly Val Ile Gly Pro
                565                 570                 575

Gly Val Ile Gly Pro Tyr Ala Ser Ala Ala Ala Ala Gly Pro Gly
            580                 585                 590

Ser Gly Val Ile Gly Pro Gly Ala Ser
        595                 600

<210> SEQ ID NO 37
<211> LENGTH: 601
<212> TYPE: PRT
<213> ORGANISM: Artificial Sequence
<220> FEATURE:
<223> OTHER INFORMATION: PRT918

<400> SEQUENCE: 37

Met His His His His His Ser Ser Gly Ser Gly Pro Gly Val
1               5                   10                  15

Phe Gly Pro Tyr Gly Pro Gly Ala Ser Ala Ala Ala Ala Gly Ile
            20                  25                  30

Asn Gly Pro Gly Ser Gly Val Phe Gly Pro Gly Ile Ser Gly Ile Tyr
        35                  40                  45

Gly Pro Gly Val Phe Gly Pro Gly Val Phe Gly Pro Gly Ser Ser Ala
    50                  55                  60

Ala Ala Ala Ala Gly Pro Gly Ile Tyr Gly Pro Gly Val Phe Gly Pro
65                  70                  75                  80

Ser Ala Ser Ala Ala Ala Ala Gly Pro Gly Ser Gly Val Phe Gly
                85                  90                  95

Pro Gly Ala Ser Gly Ile Tyr Gly Pro Gly Val Phe Gly Pro Gly Val
            100                 105                 110

Phe Gly Pro Gly Ser Ser Ala Ala Ala Ala Gly Ile Tyr Gly Ser
        115                 120                 125

Gly Pro Gly Val Phe Gly Pro Tyr Gly Ser Ala Ala Ala Ala Gly
130                 135                 140

Pro Gly Ser Gly Ile Tyr Gly Ile Gly Pro Tyr Gly Pro Gly Ala Ser
145                 150                 155                 160

Gly Pro Gly Ile Tyr Gly Pro Gly Val Phe Gly Pro Ser Ala Ser Ala
            165                 170                 175

Ala Ala Ala Gly Ser Gly Val Phe Gly Pro Gly Ile Tyr Gly Pro
        180                 185                 190

Tyr Ala Ser Ala Ala Ala Ala Gly Ile Tyr Gly Ser Gly Pro Gly
        195                 200                 205

Val Phe Gly Pro Tyr Gly Pro Gly Ile Ser Gly Ser Gly Val Phe Gly
210                 215                 220

Pro Gly Val Phe Gly Pro Tyr Ala Ser Ala Ala Ala Ala Gly Pro
225                 230                 235                 240

Gly Val Phe Gly Pro Tyr Gly Pro Gly Ser Ser Ala Ala Ala Ala
            245                 250                 255

Gly Ile Tyr Gly Tyr Gly Pro Gly Val Phe Gly Pro Tyr Gly Pro Gly
            260                 265                 270

Ala Ser Gly Ile Asn Gly Pro Gly Ser Gly Ile Tyr Gly Pro Gly Val
        275                 280                 285

Phe Gly Pro Gly Ile Ser Ala Ala Ala Ala Gly Pro Gly Val Phe
        290                 295                 300

Gly Pro Tyr Gly Pro Gly Ala Ser Ala Ala Ala Ala Gly Ile Tyr
305                 310                 315                 320

Gly Pro Gly Val Phe Gly Pro Gly Ile Tyr Gly Pro Gly Ser Ser Gly
            325                 330                 335

Pro Gly Val Phe Gly Pro Tyr Gly Pro Gly Ser Ser Ala Ala Ala Ala
            340                 345                 350

Ala Gly Ile Tyr Gly Pro Gly Val Phe Gly Pro Tyr Gly Pro Gly Ile
        355                 360                 365

Ser Ala Ala Ala Ala Gly Ile Tyr Val Phe Gly Pro Gly Val Phe
370                 375                 380

Gly Pro Tyr Gly Pro Gly Ala Ser Gly Pro Gly Val Phe Gly Pro Tyr
385                 390                 395                 400

Gly Pro Gly Ala Ser Ala Ala Ala Ala Gly Pro Gly Ile Tyr Gly
            405                 410                 415

Pro Gly Val Phe Gly Pro Ser Ala Ser Ala Ala Ala Ala Gly Ile
            420                 425                 430

Tyr Gly Ser Gly Pro Gly Ile Tyr Gly Pro Tyr Gly Pro Gly Ile Ser
        435                 440                 445

Gly Pro Gly Ser Gly Val Phe Gly Ile Gly Pro Tyr Gly Pro Gly Ala
450                 455                 460

Ser Ala Ala Ala Ala Gly Ile Tyr Gly Pro Gly Val Phe Gly Pro
465                 470                 475                 480

Tyr Gly Pro Gly Ile Ser Ala Ala Ala Ala Gly Pro Gly Ser Gly
            485                 490                 495

Ile Tyr Gly Pro Gly Ala Ser Gly Ile Asn Gly Pro Gly Ser Gly Ile
        500                 505                 510

Tyr Gly Pro Gly Val Phe Gly Pro Gly Ile Ser Ala Ala Ala Ala
        515                 520                 525

Gly Ile Tyr Val Phe Gly Pro Gly Val Phe Gly Pro Tyr Gly Pro Gly
530                 535                 540

```
Ala Ser Ala Ala Ala Ala Gly Ile Tyr Gly Ser Gly Pro Gly Val
545                 550                 555                 560

Phe Gly Pro Tyr Gly Pro Gly Ile Ser Gly Ser Gly Val Phe Gly Pro
                565                 570                 575

Gly Val Phe Gly Pro Tyr Ala Ser Ala Ala Ala Ala Gly Pro Gly
            580                 585                 590

Ser Gly Val Phe Gly Pro Gly Ala Ser
        595                 600

<210> SEQ ID NO 38
<211> LENGTH: 576
<212> TYPE: PRT
<213> ORGANISM: Artificial Sequence
<220> FEATURE:
<223> OTHER INFORMATION: PRT699

<400> SEQUENCE: 38

Met His His His His His Ser Ser Gly Ser Ser Gly Pro Gly Val
1               5                   10                  15

Leu Gly Pro Tyr Gly Pro Gly Ala Ser Ala Ala Ala Ala Ala Ala
                20                  25                  30

Gly Ser Asn Gly Pro Gly Ser Gly Val Leu Gly Pro Gln Ser Gly
            35                  40                  45

Gln Tyr Gly Pro Gly Val Leu Gly Pro Gly Val Leu Gly Pro Gly Ser
50                  55                  60

Ser Ala Ala Ala Ala Ala Ala Gly Pro Gly Gln Tyr Gly Pro Gly
65                  70                  75                  80

Val Leu Gly Pro Ser Ala Ser Ala Ala Ala Ala Ala Ala Gly Pro
                85                  90                  95

Gly Ser Gly Val Leu Gly Pro Gly Ala Ser Gln Tyr Gly Pro Gly
            100                 105                 110

Val Leu Gly Pro Gly Val Leu Gly Pro Gly Ser Ser Ala Ala Ala Ala
                115                 120                 125

Ala Ala Ala Gly Ser Tyr Gly Ser Gly Pro Gly Val Leu Gly Pro Tyr
            130                 135                 140

Gly Ser Ala Ala Ala Ala Ala Ala Gly Pro Gly Ser Gly Gln Tyr
145                 150                 155                 160

Gly Gln Gly Pro Tyr Gly Pro Gly Ala Ser Gly Pro Gly Gln Tyr Gly
                165                 170                 175

Pro Gly Val Leu Gly Pro Ser Ala Ser Ala Ala Ala Ala Ala Ala
                180                 185                 190

Gly Ser Gly Val Leu Gly Pro Gly Gln Tyr Gly Pro Tyr Ala Ser Ala
                195                 200                 205

Ala Ala Ala Ala Ala Gly Ser Tyr Gly Ser Gly Pro Gly Val Leu
            210                 215                 220

Gly Pro Tyr Gly Pro Gly Gln Ser Gly Ser Gly Val Leu Gly Pro Gly
225                 230                 235                 240

Val Leu Gly Pro Tyr Ala Ser Ala Ala Ala Ala Ala Ala Gly Pro
                245                 250                 255

Gly Val Leu Gly Pro Tyr Gly Pro Gly Ser Ala Ala Ala Ala Ala
            260                 265                 270

Ala Ala Gly Ser Tyr Gly Tyr Gly Pro Gly Val Leu Gly Pro Tyr Gly
            275                 280                 285

Pro Gly Ala Ser Gly Gln Asn Gly Pro Gly Ser Gly Gln Tyr Gly Pro
                290                 295                 300
```

```
Gly Val Leu Gly Pro Gly Pro Ser Ala Ala Ala Ala Ala Ala Ala Gly
305                 310                 315                 320

Pro Gly Val Leu Gly Pro Tyr Gly Pro Gly Ala Ser Ala Ala Ala Ala
            325                 330                 335

Ala Ala Ala Gly Ser Tyr Gly Pro Gly Val Leu Gly Pro Gly Gln Tyr
        340                 345                 350

Gly Pro Gly Ser Ser Gly Pro Gly Val Leu Gly Pro Tyr Gly Pro Gly
    355                 360                 365

Ser Ser Ala Ala Ala Ala Ala Ala Gly Ser Tyr Gly Pro Gly Val
370                 375                 380

Leu Gly Pro Tyr Gly Pro Gly Pro Ser Ala Ala Ala Ala Ala Ala
385                 390                 395                 400

Gly Ser Tyr Val Leu Gly Pro Gly Val Leu Gly Pro Tyr Gly Pro Gly
        405                 410                 415

Ala Ser Gly Pro Gly Val Leu Gly Pro Tyr Gly Pro Gly Ala Ser Ala
        420                 425                 430

Ala Ala Ala Ala Ala Ala Gly Pro Gly Gln Tyr Gly Pro Gly Val Leu
        435                 440                 445

Gly Pro Ser Ala Ser Ala Ala Ala Ala Ala Gly Ser Tyr Gly
    450                 455                 460

Ser Gly Pro Gly Gln Tyr Gly Pro Tyr Gly Pro Gly Gln Ser Gly Pro
465                 470                 475                 480

Gly Ser Gly Val Leu Gly Gln Pro Tyr Gly Pro Gly Ala Ser Ala
            485                 490                 495

Ala Ala Ala Ala Ala Gly Ser Tyr Gly Pro Gly Val Leu Gly Pro
        500                 505                 510

Tyr Gly Pro Gly Pro Ser Ala Ala Ala Ala Ala Ala Gly Pro Gly
    515                 520                 525

Ser Gly Gln Tyr Gly Pro Gly Ala Ser Gly Gln Asn Gly Pro Gly Ser
530                 535                 540

Gly Gln Tyr Gly Pro Gly Val Leu Gly Pro Gly Pro Ser Ala Ala Ala
545                 550                 555                 560

Ala Ala Ala Ala Gly Pro Gly Ser Gly Val Leu Gly Pro Gly Ala Ser
        565                 570                 575

<210> SEQ ID NO 39
<211> LENGTH: 576
<212> TYPE: PRT
<213> ORGANISM: Artificial Sequence
<220> FEATURE:
<223> OTHER INFORMATION: PRT698

<400> SEQUENCE: 39

Met His His His His His Ser Ser Gly Ser Ser Gly Pro Gly Val
1               5                   10                  15

Leu Gly Pro Tyr Gly Pro Gly Ala Ser Ala Ala Ala Ala Ala Ala
            20                  25                  30

Gly Ser Asn Gly Pro Gly Ser Gly Val Leu Gly Pro Gly Ile Ser Gly
        35                  40                  45

Ile Tyr Gly Pro Gly Val Leu Gly Pro Gly Val Leu Gly Pro Gly Ser
    50                  55                  60

Ser Ala Ala Ala Ala Ala Ala Gly Pro Gly Ile Tyr Gly Pro Gly
65                  70                  75                  80

Val Leu Gly Pro Ser Ala Ser Ala Ala Ala Ala Ala Gly Pro
            85                  90                  95
```

```
Gly Ser Gly Val Leu Gly Pro Gly Ala Ser Gly Ile Tyr Gly Pro Gly
                100                 105                 110

Val Leu Gly Pro Gly Val Leu Gly Pro Gly Ser Ser Ala Ala Ala Ala
            115                 120                 125

Ala Ala Ala Gly Ser Tyr Gly Ser Gly Pro Gly Val Leu Gly Pro Tyr
        130                 135                 140

Gly Ser Ala Ala Ala Ala Ala Ala Gly Pro Gly Ser Gly Ile Tyr
145                 150                 155                 160

Gly Ile Gly Pro Tyr Gly Pro Gly Ala Ser Gly Pro Gly Ile Tyr Gly
                165                 170                 175

Pro Gly Val Leu Gly Pro Ser Ala Ser Ala Ala Ala Ala Ala Ala
            180                 185                 190

Gly Ser Gly Val Leu Gly Pro Gly Ile Tyr Gly Pro Tyr Ala Ser Ala
        195                 200                 205

Ala Ala Ala Ala Ala Ala Gly Ser Tyr Gly Ser Gly Pro Gly Val Leu
        210                 215                 220

Gly Pro Tyr Gly Pro Gly Ile Ser Gly Ser Gly Val Leu Gly Pro Gly
225                 230                 235                 240

Val Leu Gly Pro Tyr Ala Ser Ala Ala Ala Ala Ala Ala Gly Pro
            245                 250                 255

Gly Val Leu Gly Pro Tyr Gly Pro Gly Ser Ser Ala Ala Ala Ala
        260                 265                 270

Ala Ala Gly Ser Tyr Gly Tyr Gly Pro Gly Val Leu Gly Pro Tyr Gly
        275                 280                 285

Pro Gly Ala Ser Gly Ile Asn Gly Pro Gly Ser Gly Ile Tyr Gly Pro
        290                 295                 300

Gly Val Leu Gly Pro Gly Pro Ser Ala Ala Ala Ala Ala Ala Gly
305                 310                 315                 320

Pro Gly Val Leu Gly Pro Tyr Gly Pro Gly Ala Ser Ala Ala Ala
            325                 330                 335

Ala Ala Ala Gly Ser Tyr Gly Pro Gly Val Leu Gly Pro Gly Ile Tyr
        340                 345                 350

Gly Pro Gly Ser Ser Gly Pro Gly Val Leu Gly Pro Tyr Gly Pro Gly
        355                 360                 365

Ser Ser Ala Ala Ala Ala Ala Ala Gly Ser Tyr Gly Pro Gly Val
370                 375                 380

Leu Gly Pro Tyr Gly Pro Gly Pro Ser Ala Ala Ala Ala Ala Ala
385                 390                 395                 400

Gly Ser Tyr Val Leu Gly Pro Gly Val Leu Gly Pro Tyr Gly Pro Gly
            405                 410                 415

Ala Ser Gly Pro Gly Val Leu Gly Pro Tyr Gly Pro Gly Ala Ser Ala
            420                 425                 430

Ala Ala Ala Ala Ala Ala Gly Pro Gly Ile Tyr Gly Pro Gly Val Leu
        435                 440                 445

Gly Pro Ser Ala Ser Ala Ala Ala Ala Ala Gly Ser Tyr Gly
        450                 455                 460

Ser Gly Pro Gly Ile Tyr Gly Pro Tyr Gly Pro Gly Ile Ser Gly Pro
465                 470                 475                 480

Gly Ser Gly Val Leu Gly Ile Gly Pro Tyr Gly Pro Gly Ala Ser Ala
            485                 490                 495

Ala Ala Ala Ala Ala Gly Ser Tyr Gly Pro Gly Val Leu Gly Pro
        500                 505                 510

Tyr Gly Pro Gly Pro Ser Ala Ala Ala Ala Ala Ala Gly Pro Gly
```

```
                515                 520                 525
Ser Gly Ile Tyr Gly Pro Gly Ala Ser Gly Ile Asn Gly Pro Gly Ser
    530                 535                 540

Gly Ile Tyr Gly Pro Gly Val Leu Gly Pro Gly Pro Ser Ala Ala Ala
545                 550                 555                 560

Ala Ala Ala Ala Gly Pro Gly Ser Gly Val Leu Gly Pro Gly Ala Ser
                565                 570                 575

<210> SEQ ID NO 40
<211> LENGTH: 1190
<212> TYPE: PRT
<213> ORGANISM: Artificial Sequence
<220> FEATURE:
<223> OTHER INFORMATION: PRT966

<400> SEQUENCE: 40

Met His His His His His Ser Ser Gly Ser Ser Gly Pro Gly Val
1               5                   10                  15

Phe Gly Pro Tyr Gly Pro Gly Ala Ser Ala Ala Ala Ala Gly Ile
            20                  25                  30

Asn Gly Pro Gly Ser Gly Val Phe Gly Pro Gly Ile Ser Gly Ile Tyr
        35                  40                  45

Gly Pro Gly Val Phe Gly Pro Gly Val Phe Gly Pro Gly Ser Ser Ala
    50                  55                  60

Ala Ala Ala Ala Gly Pro Gly Ile Tyr Gly Pro Gly Val Phe Gly Pro
65                  70                  75                  80

Ser Ala Ser Ala Ala Ala Ala Gly Pro Gly Ser Gly Val Phe Gly
                85                  90                  95

Pro Gly Ala Ser Gly Ile Tyr Gly Pro Gly Val Phe Gly Pro Gly Val
                100                 105                 110

Phe Gly Pro Gly Ser Ser Ala Ala Ala Ala Gly Ile Tyr Gly Ser
            115                 120                 125

Gly Pro Gly Val Phe Gly Pro Tyr Gly Ser Ala Ala Ala Ala Gly
        130                 135                 140

Pro Gly Ser Gly Ile Tyr Gly Ile Gly Pro Tyr Gly Pro Gly Ala Ser
145                 150                 155                 160

Gly Pro Gly Ile Tyr Gly Pro Gly Val Phe Gly Pro Ser Ala Ser Ala
                165                 170                 175

Ala Ala Ala Gly Ser Gly Val Phe Gly Pro Gly Ile Tyr Gly Pro
            180                 185                 190

Tyr Ala Ser Ala Ala Ala Ala Gly Ile Tyr Gly Ser Gly Pro Gly
        195                 200                 205

Val Phe Gly Pro Tyr Gly Pro Gly Ile Ser Gly Ser Gly Val Phe Gly
    210                 215                 220

Pro Gly Val Phe Gly Pro Tyr Ala Ser Ala Ala Ala Ala Gly Pro
225                 230                 235                 240

Gly Val Phe Gly Pro Tyr Gly Pro Gly Ser Ala Ala Ala Ala Ala
                245                 250                 255

Gly Ile Tyr Gly Tyr Gly Pro Gly Val Phe Gly Pro Tyr Gly Pro Gly
            260                 265                 270

Ala Ser Gly Ile Asn Gly Pro Gly Ser Gly Ile Tyr Gly Pro Gly Val
        275                 280                 285

Phe Gly Pro Gly Ile Ser Ala Ala Ala Ala Gly Pro Gly Val Phe
    290                 295                 300

Gly Pro Tyr Gly Pro Gly Ala Ser Ala Ala Ala Ala Gly Ile Tyr
```

```
                305                 310                 315                 320
        Gly Pro Gly Val Phe Gly Pro Gly Ile Tyr Gly Pro Gly Ser Ser Gly
                        325                 330                 335

Pro Gly Val Phe Gly Pro Tyr Gly Pro Gly Ser Ser Ala Ala Ala Ala
                        340                 345                 350

Ala Gly Ile Tyr Gly Pro Gly Val Phe Gly Pro Tyr Gly Pro Gly Ile
                        355                 360                 365

Ser Ala Ala Ala Ala Gly Ile Tyr Val Phe Gly Pro Gly Val Phe
                        370                 375                 380

Gly Pro Tyr Gly Pro Gly Ala Ser Gly Pro Gly Val Phe Gly Pro Tyr
        385                 390                 395                 400

Gly Pro Gly Ala Ser Ala Ala Ala Ala Gly Pro Gly Ile Tyr Gly
                        405                 410                 415

Pro Gly Val Phe Gly Pro Ser Ala Ser Ala Ala Ala Ala Gly Ile
                        420                 425                 430

Tyr Gly Ser Gly Pro Gly Ile Tyr Gly Pro Tyr Gly Pro Gly Ile Ser
                        435                 440                 445

Gly Pro Gly Ser Gly Val Phe Gly Ile Gly Pro Tyr Gly Pro Gly Ala
                450                 455                 460

Ser Ala Ala Ala Ala Gly Ile Tyr Gly Pro Gly Val Phe Gly Pro
        465                 470                 475                 480

Tyr Gly Pro Gly Ile Ser Ala Ala Ala Ala Gly Pro Gly Ser Gly
                        485                 490                 495

Ile Tyr Gly Pro Gly Ala Ser Gly Ile Asn Gly Pro Gly Ser Gly Ile
                        500                 505                 510

Tyr Gly Pro Gly Val Phe Gly Pro Gly Ile Ser Ala Ala Ala Ala
                        515                 520                 525

Gly Ile Tyr Val Phe Gly Pro Gly Val Phe Gly Pro Tyr Gly Pro Gly
                        530                 535                 540

Ala Ser Ala Ala Ala Ala Gly Ile Tyr Gly Ser Gly Pro Gly Val
        545                 550                 555                 560

Phe Gly Pro Tyr Gly Pro Gly Ile Ser Gly Ser Gly Val Phe Gly Pro
                        565                 570                 575

Gly Val Phe Gly Pro Tyr Ala Ser Ala Ala Ala Ala Gly Pro Gly
                        580                 585                 590

Ser Gly Val Phe Gly Pro Gly Ala Ser Gly Pro Gly Val Phe Gly Pro
                        595                 600                 605

Tyr Gly Pro Gly Ala Ser Ala Ala Ala Ala Gly Ile Asn Gly Pro
                        610                 615                 620

Gly Ser Gly Val Phe Gly Pro Gly Ile Ser Gly Ile Tyr Gly Pro Gly
        625                 630                 635                 640

Val Phe Gly Pro Gly Val Phe Gly Pro Gly Ser Ser Ala Ala Ala
                        645                 650                 655

Ala Gly Pro Gly Ile Tyr Gly Pro Gly Val Phe Gly Pro Ser Ala Ser
                        660                 665                 670

Ala Ala Ala Ala Gly Pro Gly Ser Gly Val Phe Gly Pro Gly Ala
                        675                 680                 685

Ser Gly Ile Tyr Gly Pro Gly Val Phe Gly Pro Gly Val Phe Gly Pro
                        690                 695                 700

Gly Ser Ser Ala Ala Ala Ala Gly Ile Tyr Gly Ser Gly Pro Gly
        705                 710                 715                 720

Val Phe Gly Pro Tyr Gly Ser Ala Ala Ala Ala Gly Pro Gly Ser
                        725                 730                 735
```

```
Gly Ile Tyr Gly Ile Gly Pro Tyr Gly Pro Gly Ala Ser Gly Pro Gly
                740                 745                 750

Ile Tyr Gly Pro Gly Val Phe Gly Pro Ser Ala Ser Ala Ala Ala Ala
        755                 760                 765

Ala Gly Ser Gly Val Phe Gly Pro Gly Ile Tyr Gly Pro Tyr Ala Ser
770                 775                 780

Ala Ala Ala Ala Ala Gly Ile Tyr Gly Ser Gly Pro Gly Val Phe Gly
785                 790                 795                 800

Pro Tyr Gly Pro Gly Ile Ser Gly Ser Gly Val Phe Gly Pro Gly Val
                805                 810                 815

Phe Gly Pro Tyr Ala Ser Ala Ala Ala Ala Gly Pro Gly Val Phe
        820                 825                 830

Gly Pro Tyr Gly Pro Gly Ser Ser Ala Ala Ala Ala Gly Ile Tyr
        835                 840                 845

Gly Tyr Gly Pro Gly Val Phe Gly Pro Tyr Gly Pro Gly Ala Ser Gly
850                 855                 860

Ile Asn Gly Pro Gly Ser Gly Ile Tyr Gly Pro Gly Val Phe Gly Pro
865                 870                 875                 880

Gly Ile Ser Ala Ala Ala Ala Gly Pro Gly Val Phe Gly Pro Tyr
        885                 890                 895

Gly Pro Gly Ala Ser Ala Ala Ala Ala Gly Ile Tyr Gly Pro Gly
        900                 905                 910

Val Phe Gly Pro Gly Ile Tyr Gly Pro Gly Ser Ser Gly Pro Gly Val
        915                 920                 925

Phe Gly Pro Tyr Gly Pro Gly Ser Ser Ala Ala Ala Ala Gly Ile
        930                 935                 940

Tyr Gly Pro Gly Val Phe Gly Pro Tyr Gly Pro Gly Ile Ser Ala Ala
945                 950                 955                 960

Ala Ala Ala Gly Ile Tyr Val Phe Gly Pro Gly Val Phe Gly Pro Tyr
                965                 970                 975

Gly Pro Gly Ala Ser Gly Pro Gly Val Phe Gly Pro Tyr Gly Pro Gly
                980                 985                 990

Ala Ser Ala Ala Ala Ala Ala Gly Pro Gly Ile Tyr Gly Pro Gly Val
        995                 1000                1005

Phe Gly Pro Ser Ala Ser Ala Ala Ala Ala Ala Gly Ile Tyr Gly
        1010                1015                1020

Ser Gly Pro Gly Ile Tyr Gly Pro Tyr Gly Pro Gly Ile Ser Gly
        1025                1030                1035

Pro Gly Ser Gly Val Phe Gly Ile Gly Pro Tyr Gly Pro Gly Ala
        1040                1045                1050

Ser Ala Ala Ala Ala Gly Ile Tyr Gly Pro Gly Val Phe Gly
        1055                1060                1065

Pro Tyr Gly Pro Gly Ile Ser Ala Ala Ala Ala Ala Gly Pro Gly
        1070                1075                1080

Ser Gly Ile Tyr Gly Pro Gly Ala Ser Gly Ile Asn Gly Pro Gly
        1085                1090                1095

Ser Gly Ile Tyr Gly Pro Gly Val Phe Gly Pro Gly Ile Ser Ala
        1100                1105                1110

Ala Ala Ala Gly Ile Tyr Val Phe Gly Pro Gly Val Phe Gly
        1115                1120                1125

Pro Tyr Gly Pro Gly Ala Ser Ala Ala Ala Ala Gly Ile Tyr
        1130                1135                1140
```

-continued

```
Gly  Ser  Gly  Pro  Gly  Val  Phe  Gly  Pro  Tyr  Gly  Pro  Gly  Ile  Ser
     1145                     1150                    1155

Gly  Ser  Gly  Val  Phe  Gly  Pro  Gly  Val  Phe  Gly  Pro  Tyr  Ala  Ser
     1160                     1165                    1170

Ala  Ala  Ala  Ala  Ala  Gly  Pro  Gly  Ser  Gly  Val  Phe  Gly  Pro  Gly
     1175                     1180                    1185

Ala  Ser
     1190
```

MOLDED ARTICLE AND METHOD FOR PRODUCTION THEREOF

SEQUENCE LISTING SUBMISSION VIA EFS-WEB

A computer readable text file, entitled "SequenceListing.txt," created on or about Sep. 29, 2020 with a file size of about 224 kb contains the sequence listing for this application and is hereby incorporated by reference in its entirety.

TECHNICAL FIELD

The present invention relates to a molded article and a method for producing the same.

BACKGROUND ART

Silk fiber is a natural fiber obtainable from silkworm cocoons. Silk fiber is a material that has excellent mechanical characteristics, moisture absorbing characteristics, and deodorizing characteristics and is widely used as a raw material for clothes. Silk fiber is an immunologically tolerant natural fiber, and since the bioaffinity is high, silk fiber is also used for use applications such as surgical sutures.

Regarding silk fiber, it is known that the fiber strength is noticeably decreased in a wet state, and material deterioration such as friction marks and pilling, and notable dimensional changes (shrinkage) occur. Various means for coping with problems such as deterioration in this wet state have been proposed (for example, Patent Literature 1).

CITATION LIST

Patent Literature

Patent Literature 1: Japanese Unexamined Patent Publication No. 2012-246580

SUMMARY OF INVENTION

Technical Problem

An investigation of the inventors of the present invention has found that a molded article (for example, modified fibroin fibers) obtained by molding artificially produced fibroin (modified fibroin) does not have sufficient water resistance such as water repellency and contractibility at the time of contact with water. With regard to a molded article including a modified fibroin, it has not been hitherto known that water resistance becomes a problem, and with regard to the means for coping with this, it is a current situation that sufficient investigation has not yet been achieved.

An object of the present invention is to provide a molded article that includes a modified fibroin having enhanced water resistance. Another object of the present invention is to provide a method for producing a molded article that includes a modified fibroin having enhanced water resistance.

Solution to Problem

The present invention relates to, for example, the following respective inventions.

[1]
A molded article including a modified fibroin and a water resistance-imparting material.
[2]
The molded article as described in [1], wherein the modified fibroin and the water resistance-imparting material are covalently bonded.
[3]
The molded article as described in [1] or [2], wherein the water resistance-imparting material is at least one selected from a silicone-based polymer and a fluorine-based polymer.
[4]
The molded article as described in any one of [1] to [3], wherein the modified fibroin is a modified spider silk fibroin.
[5]
A method for producing a molded article, the method comprising a step of bonding a water resistance-imparting material to a precursor molded article including a modified fibroin.
[6]
The method as described in [5], wherein the above-described step of bonding the water resistance-imparting material to the precursor molded article includes irradiating the precursor molded article with plasma in a state in which the water resistance-imparting material or a precursor of the water resistance-imparting material is brought into contact with the precursor molded article, and thereby covalently bonding the modified fibroin and the water resistance-imparting material.
[7]
The method as described in [5] or [6], wherein the water resistance-imparting material is at least one selected from a silicone-based polymer and a fluorine-based polymer.
[8]
The method as described in any one of [5] to [7], wherein the modified fibroin is a modified spider silk fibroin.
[9] A method for producing a molded article, the method comprising a step of molding a raw material containing a modified fibroin and a water resistance-imparting material and thereby obtaining a molded article.

Advantageous Effects of Invention

According to the present invention, it is possible to provide a molded article that includes a modified fibroin having enhanced water resistance. According to the present invention, it is also possible to provide a method for producing a molded article that includes a modified fibroin having enhanced water resistance.

DESCRIPTION OF EMBODIMENTS

Figure 1:
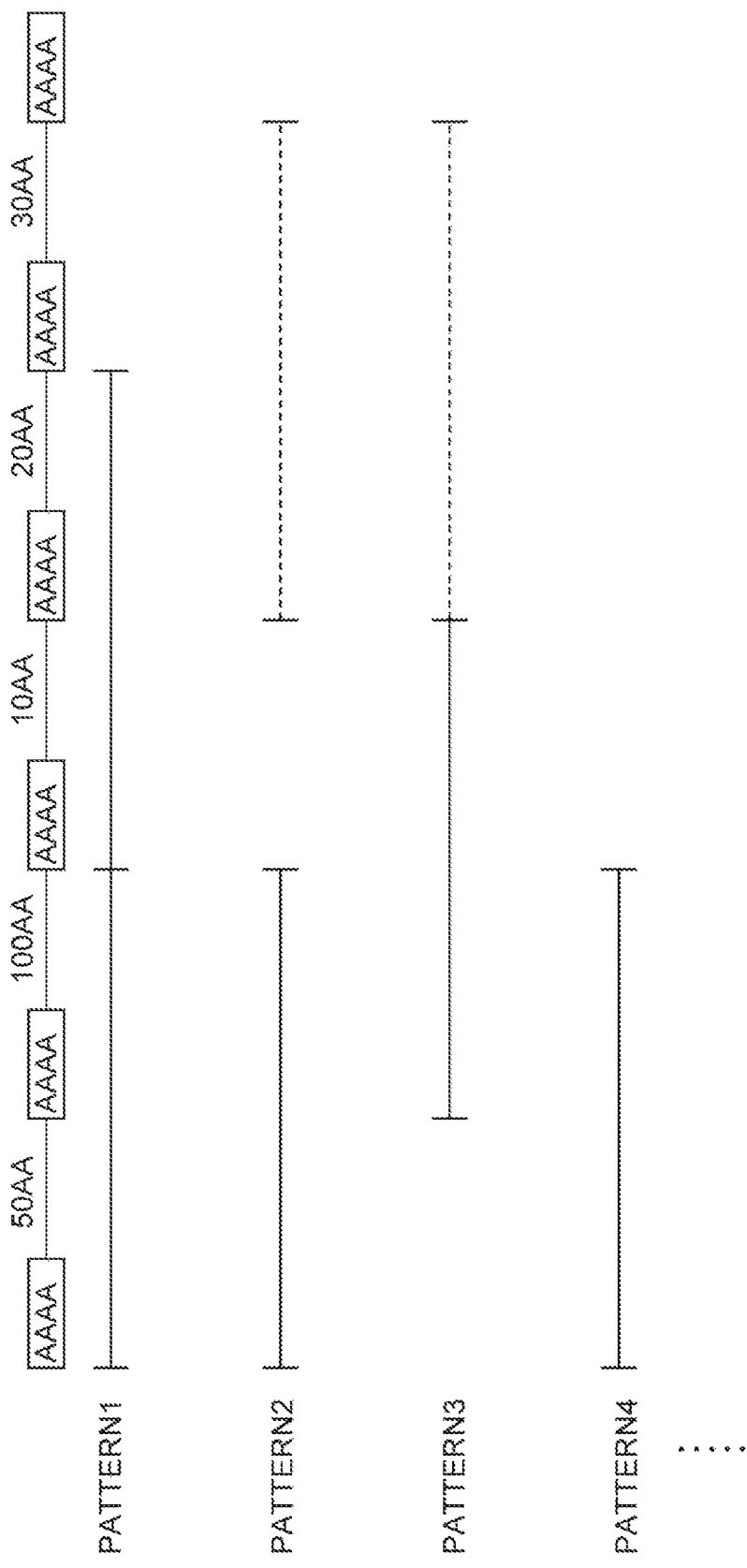
FIG. 1 is a schematic diagram showing the domain sequence of a modified fibroin according to an embodiment.

In the following description, embodiments for carrying out the present invention will be described in detail. However, the present invention is not intended to be limited to the following embodiments.

Molded Article

A molded article according to the present invention includes a modified fibroin and a water resistance-imparting material.

<Modified Fibroin>

A modified fibroin according to the present embodiment is a protein including a domain sequence represented by Formula 1: $[(A)_n$ motif-REP$]_m$ or Formula 2: $[(A)_n$ motif-REP$]_m$-$(A)_n$ motif. The modified fibroin may have an amino acid sequence (N-terminal sequence and C-terminal sequence) further added to either or both of the N-terminus side and the C-terminus side of the domain sequence. The N-terminal sequence and the C-terminal sequence are regions that do not have repetitions of amino acid motifs characteristic of fibroin, and comprise about 100 residues of amino acids; however, the N-terminal sequence and the C-terminal sequence are not limited to these.

The term "modified fibroin" according to the present specification means an artificially produced fibroin (synthetic fibroin). The modified fibroin may be a fibroin whose domain sequence is different from the amino acid sequence of naturally occurring fibroin, or a fibroin whose domain sequence is identical to the amino acid sequence of naturally occurring fibroin. The term "naturally occurring fibroin" as used in the present specification is also a protein including a domain sequence represented by Formula 1: $[(A)_n$ motif-REP$]_m$ or Formula 2: $[(A)_n$ motif-REP$]_m$-$(A)_n$ motif.

The "modified fibroin" may be a fibroin that directly utilizes the amino acid sequence of naturally occurring fibroin, may be a fibroin obtained by modifying the amino acid sequence of naturally occurring fibroin based on the amino acid sequence (for example, a fibroin whose amino acid sequence has been modified by modifying a gene sequence of cloned naturally occurring fibroin), or may be a fibroin that has been artificially designed and synthesized independently of naturally occurring fibroin (for example, a fibroin having a desired amino acid sequence by chemically synthesizing a nucleic acid encoding the designed amino acid sequence).

The term "domain sequence" according to the present specification means an amino acid sequence that produce a crystalline region characteristic of fibroin (typically, corresponding to the $(A)_n$ motif in the amino acid sequence) and a non-crystalline region (typically, corresponding to REP in the amino acid sequence), and means an amino acid sequence represented by Formula 1: $[(A)_n$ motif-REP$]_m$ or Formula 2: $[(A)_n$ motif-REP$]_m$-$(A)_n$ motif. Here, the $(A)_n$ motif represents an amino acid sequence mainly comprising alanine residues, and the number of amino acid residues is 2 to 27. The number of amino acid residues in the $(A)_n$ motif may be an integer of 2 to 20, 4 to 27, 4 to 20, 8 to 20, 10 to 20, 4 to 16, 8 to 16, or 10 to 16. Furthermore, the proportion of the number of alanine residues with respect to the total number of amino acid residues in the $(A)_n$ motif, and the proportion may be 60% or more, 70% or more, 80% or more, 83% or more, 85% or more, 86% or more, 90% or more, 95% or more, or 100% (meaning that the motif is composed only of alanine residues). A plurality of $(A)_n$ motifs present in the domain sequence may be such that at least seven of the motifs are composed only of alanine residues. REP represents an amino acid sequence composed of 2 to 200 amino acid residues. REP may also be an amino acid sequence composed of 10 to 200 amino acid residues. m represents an integer of 2 to 300 and may be an integer of 10 to 300. A plurality of $(A)_n$ motifs present therein may be amino acid sequences that are identical to each other or may be different amino acid sequences. A plurality of REP's present therein may be amino acid sequences that are identical to each other or may be different amino acid sequences.

The modified fibroin according to the present embodiment can be obtained by, for example, subjecting the gene sequence of cloned naturally occurring fibroin to modifications of an amino acid sequence corresponding to substitution, deletion, insertion, and/or addition of one or a plurality of amino acid residue(s). The substitution, deletion, insertion, and/or addition of amino acid residues can be carried out by methods well known to those ordinarily skilled in the art, such as a partial specific mutagenesis method. Specifically, the modifications can be carried out according to methods described in the literature such as Nucleic Acid Res. 10, 6487 (1982) and Methods in Enzymology, 100, 448 (1983).

Naturally occurring fibroin is a protein including a domain sequence represented by Formula 1: $[(A)_n$ motif-REP$]_m$ or Formula 2: $[(A)_n$ motif-REP$]_m$-$(A)_n$ motif and specifically, for example, a fibroin produced by insects or spiders may be mentioned.

Examples of the fibroin produced by insects include silk proteins produced by silkworms such as *Bombyx mori, Bombyx mandarina, Antheraea yamamai, Anteraea pernyi, Eriogyna pyretorum, Pilosamia Cynthia ricini, Samia cynthia, Caligura japonica, Antheraea mylitta*, and *Antheraea assama*; and hornet silk proteins discharged by larvae of *Vespa simillima xanthoptera*.

A more specific example of the fibroin produced by insects may be, for example, a silkworm fibroin L chain (GenBank Accession No. M76430 (nucleotide sequence) and AAA27840.1 (amino acid sequence)).

Examples of the fibroin produced by spiders include spider silk proteins produced by spiders belonging to the genus *Araneus*, such as *Araneus ventricosus, Araneus diadematus, Araneus pinguis, Araneus pentagrammicus*, and *Araneus nojimai*; spiders belonging to the genus *Neoscona*, such as *Neoscona scylla, Neoscona nautica, Neoscona adianta*, and *Neoscona scylloides*; spiders belonging to the genus *Pronus*, such as *Pronous minutes*; spiders belonging to the genus *Cyrtarachne*, such as *Cyrtarachne bufo* and *Cyrtarachne inaequalis*; spiders belonging to the genus *Gasteracantha*, such as *Gasteracantha kuhli* and *Gasteracantha mammosa*; spiders belonging to the genus *Ordgarius*, such as *Ordgarius hobsoni* and *Ordgarius sexspinosus*; spiders belonging to the genus *Argiope*, such as *Argiope amoena, Argiope minuta*, and *Argiope bruennich*; spiders belonging to the genus *Arachnura*, such as *Arachnura logio*; spiders belonging to the genus *Acusilas*, such as *Acusilas coccineus*; spiders belonging to the genus *Cytophora*, such as *Cyrtophora moluccensis, Cyrtophora exanthematica*, and *Cyrtophora unicolor*; spiders belonging to the genus *Poltys*, such as *Poltys illepidus*; spiders belonging to the genus *Cyclosa*, such as *Cyclosa octotuberculata, Cyclosa sedeculata, Cyclosa vallate*, and *Cyclosa atrata*; and spiders belonging to the genus *Chorizopes*, such as *Chorizopes nipponicus*; and spider silk proteins produced by spiders belonging to the genus *Tetragnatha*, such as *Tetragnatha praedonia, Tetragnatha maxillosa, Tetragnatha extensa*, and *Tetragnatha squamata*; spiders belonging to the genus *Leucauge*, such as *Leucauge magnifica, Leucauge blanda*, and *Leucauge subblanda*; spiders belonging to the genus *Nephila*, such as *Nephila clavate* and *Nephila pilipes*; spiders belonging to the genus *Menosira*, such as *Menosira ornate*; spiders belonging to the genus *Dyschiriognatha*, such as *Dyschiriognatha tenera*; spiders belonging to the genus *Latrodectus*, such as *Latrodectus mactans, Latrodectus hasseltii, Latrodectus geometricus*, and *Latrodectus*

*tredecimguttatus*; and spiders belonging to the family Tetragnathidae, such as spiders belonging to the genus *Euprosthenops*. Examples of the spider silk proteins include traction fiber proteins such as MaSp (MaSp1 and MaSp2) and ADF (ADF3 and ADF4); and MiSp (MiSp1 and MiSp2).

More specific examples of the spider silk proteins produced by spiders include, for example, fibroin-3 (adf-3) [derived from *Araneus diadematus*] (GenBank Accession Numbers AAC47010 (amino acid sequence), U47855 (base sequence)), fibroin-4 (adf-4) [derived from *Araneus diadematus*] (GenBank Accession Numbers AAC47011 (amino acid sequence), U47856 (base sequence)), dragline silk protein spidroin 1 [derived from *Nephila clavipes*] (GenBank Accession Numbers AAC04504 (amino acid sequence), U37520 (base sequence)), major ampullate spidroin 1 [derived from *Latrodectus hesperus*] (GenBank Accession Numbers ABR68856 (amino acid sequence), EF595246 (base sequence)), dragline silk protein spidroin 2 [derived from *Nephila clavata*] (GenBank Accession Number AAL32472 (amino acid sequence), AF441245 (base sequence)), major ampullate spidroin 1 [derived from *Euprosthenops australis*] (GenBank Accession Numbers CAJ00428 (amino acid sequence), AJ973155 (base sequence)), and major ampullate spidroin 2 [*Euprosthenops australis*] (GenBank Accession Numbers CAM32249.1 (amino acid sequence), AM490169 (base sequence)), minor ampullate silk protein 1 [*Nephila clavipes*](GenBank Accession Number AAC14589.1 (amino acid sequence)), minor ampullate silk protein 2 [*Nephila clavipes*] (GenBank Accession Number AAC14591.1 (amino acid sequence)), and minor ampullate spidroin-like protein [*Nephilengys cruentata*] (GenBank Accession Number ABR37278.1 (amino acid sequence).

As a more specific example of naturally occurring fibroin, furthermore, fibroin whose sequence information is registered with NCBI GenBank can be mentioned. For example, it can be checked by extracting sequences for which the term spidroin, ampullate, fibroin, "silk and polypeptide", or "silk and protein" is described as a keyword in DEFINITION among the sequences including INV as DIVISION in the sequence information registered with the NCBI GenBank, and sequences in which a particular character string of product from CDS, or a particular character string from SOURCE to TISSUE TYPE.

The modified fibroin according to the present embodiment may be modified silk fibroin (a product obtained by modifying the amino acid sequence of silk protein produced by silkworms), or may be modified spider silk fibroin (a product obtained by modifying the amino acid sequence of spider silk protein produced by spiders). The modified fibroin is preferably a modified spider silk fibroin.

Specific examples of the modified fibroin include a modified fibroin derived from a large spinneret dragline protein produced at the major ampullate gland of a spider (modified fibroin of first embodiment), a modified fibroin in which the content of glycine residues has been reduced (modified fibroin of second embodiment), a modified fibroin in which the content of the $(A)_n$ motif has been reduced (modified fibroin of third embodiment), a modified in which the content of glycine residues and the content of the $(A)_n$ motif have been reduce (modified fibroin of fourth embodiment), a modified fibroin having a domain sequence that includes a region in which the hydropathy index is locally large (modified fibroin of fifth embodiment), and a modified fibroin having a domain sequence in which the content of glutamine residues has been reduced (modified fibroin of sixth embodiment).

As the modified fibroin of the first embodiment, a protein including a domain sequence represented by Formula 1: $[(A)_n \text{ motif-REP}]_m$ may be mentioned. With regard to the modified fibroin of the first embodiment, the number of amino acid residues of the $(A)_n$ motif is preferably an integer of 3 to 20, more preferably an integer of 4 to 20, even more preferably an integer of 8 to 20, still more preferably an integer of 10 to 20, even more preferably an integer of 4 to 16, particularly preferably an integer of 8 to 16, and most preferably an integer of 10 to 16. In the modified fibroin of the first embodiment, the number of amino acid residues constituting an REP in Formula 1 is preferably 10 to 200 residues, more preferably 10 to 150 residues, even more preferably 20 to 100 residues, and still more preferably 20 to 75 residues. In the modified fibroin of the first embodiment, the total number of residues of glycine residues, serine residues, and alanine residues included in the amino acid sequence represented by Formula 1: $[(A)_n \text{ motif-REP}]_m$ is preferably 40% or more, more preferably 60% or more, and even more preferably 70% or more, with respect to the total number of amino acid residues.

The modified fibroin of the first embodiment may be a polypeptide including a unit of an amino acid sequence represented by Formula 1: $[(A)_n \text{ motif-REP}]_m$, wherein the C-terminal sequence is an amino acid sequence set forth in any one of SEQ ID NO:1 to SEQ ID NO:3, or an amino acid sequence having an identity of 90% or higher with an amino acid sequence set forth in any one of SEQ ID NO:1 to SEQ ID NO:3.

The amino acid sequence set forth in SEQ ID NO:1 is identical to an amino acid sequence comprising 50 residues of amino acids at the C-terminus of the amino acid sequence of ADF3 (GI: 1263287, NCBI), the amino acid sequence set forth in SEQ ID NO:2 is identical to an amino acid sequence obtained by eliminating 20 residues from the C-terminus of the amino acid sequence set forth in SEQ ID NO:1, and the amino acid sequence set forth in SEQ ID NO:3 is identical to an amino acid sequence obtained by eliminating 29 residues from the C-terminus of the amino acid sequence set forth in SEQ ID NO:1.

As a more specific example of the modified fibroin of the first embodiment, a modified fibroin including: (1-i) an amino acid sequence set forth in SEQ ID NO:4 (recombinant spider silk protein ADF3KaiLargeNRSH1), or (1-ii) an amino acid sequence having a sequence identity of 90% or higher with an amino acid sequence set forth in SEQ ID NO:4, may be mentioned. The sequence identity is preferably 95% or higher.

The amino acid sequence set forth in SEQ ID NO:4 is an amino acid sequence obtained by mutating the amino acid sequence of ADF3, to which an amino acid sequence (SEQ ID NO:5) comprising a start codon, His10 tag, and HRV3C protease (Human rhinovirus 3C protease) recognition site has been added to the N-terminus, such that the $1^{st}$ to $13^{th}$ repeating regions are increased to approximately double, and the translation is terminated at the $1154^{th}$ amino acid residue. The amino acid sequence at the C-terminus of the amino acid sequence set forth in SEQ ID NO:4 is identical to the amino acid sequence set forth in SEQ ID NO:3.

The modified fibroin of (1-i) may comprise the amino acid sequence set forth in SEQ ID NO:4.

In the modified fibroin of the second embodiment, the domain sequence thereof has an amino acid sequence in which the content of glycine residues has been reduced as compared to naturally occurring fibroin. The modified fibroin of the second embodiment can be said to have an amino acid sequence corresponding to at least having one or a plurality of glycine residues in the REP substituted with another amino acid residue(s), as compared to naturally occurring fibroin.

The modified fibroin of the second embodiment may be such that the domain sequence thereof has at least an amino acid sequence in which in at least one motif sequence selected from GGX and GPGXX (provided that G represents a glycine residue; P represents a proline residue; and X represents an amino acid residue other than glycine) in the REP, one glycine residue in one or a plurality of the aforementioned motif sequences has been substituted with another amino acid residue, as compared to naturally occurring fibroin.

In the modified fibroin of the second embodiment, the proportion of a motif sequence in which the above-mentioned glycine residue has been substituted with another amino acid residue may be 10% or more with respect to the entire motif sequence.

The modified fibroin of the second embodiment may be a modified fibrin that includes a domain sequence represented by Formula 1: $[(A)_n\text{ motif-REP}]_m$, and has an amino acid sequence in which when the total number of amino acid residues in an amino acid sequence comprising XGX (provided that X represents an amino acid residue other than glycine) included in all the REP's in a sequence obtained by excluding the sequence from the $(A)_n$ motif located on the furthermost C-terminus side to the C-terminus of the above-described domain sequence, from the above-described domain sequence is designated as z, and the total number of amino acid residues in a sequence obtained by excluding the sequence from the $(A)_n$ motif located on the furthermost C-terminus side to the C-terminus of the above-described domain sequence, from the above-described domain sequence is designated as w, z/w is 30% or more, 40% or more, 50% or more, or 50.9% or more. The number of alanine residues with respect to the total number of amino acid residues in the $(A)_n$ motif may be 83% or more; however, the number of alanine residues is preferably 86% or more, more preferably 90% or more, even more preferably 95% or more, and still more preferably 100% (meaning that the $(A)_n$ motif is composed only of alanine residues).

Regarding the modified fibroin of the second embodiment, it is preferable that the content proportion of the amino acid sequence comprising XGX has been increased by substituting one glycine residue of a GGX motif with another amino acid residue. With regard to the modified fibroin of the second embodiment, it is preferable that the content proportion of the amino acid sequence comprising GGX in the domain sequence is 30% or less, more preferably 20% or less, even more preferably 10% or less, still more preferably 6% or less, further more preferably 4% or less, and particularly preferably 2% or less. The content proportion of the amino acid sequence comprising GGX in the domain sequence can be calculated by a method similar to the method for calculating the content proportion (z/w) of the amino acid sequence comprising XGX as described below.

The method for calculating z/w will be described in more detail. First, for a fibroin (modified fibroin or naturally occurring fibroin) including a domain sequence represented by Formula 1: $[(A)_n\text{ motif-REP}]_m$, the amino acid sequence comprising XGX is extracted from all the REP's included in a sequence obtained by excluding the sequence from the $(A)_n$ motif located on the furthermost C-terminus side to the C-terminus of the domain sequence, from the domain sequence. The total number of amino acid residues constituting XGX is z. For example, in a case in which 50 amino acid sequences comprising XGX have been extracted (there is no overlap), z is 50×3=150. Furthermore, for example, in a case in which there is an X included in two XGX sequences (central X) as in the case of an amino acid sequence comprising XGXGX, calculation is performed by deducting the overlapping portion (in the case of XGXGX, five amino acid residues). w represents the total number of amino acid residues included in a sequence obtained by excluding the sequence from the $(A)_n$ motif located on the furthermost C-terminus side to the C-terminus of the domain sequence, from the domain sequence. For example, in the case of the domain sequence shown in FIG. 1, w is 4+50+4+100+4+10+4+20+4+30=230 (excluding the $(A)_n$ motif located on the furthermost C-terminus side). Next, z/w (%) can be calculated by dividing z by w.

Figure 2:
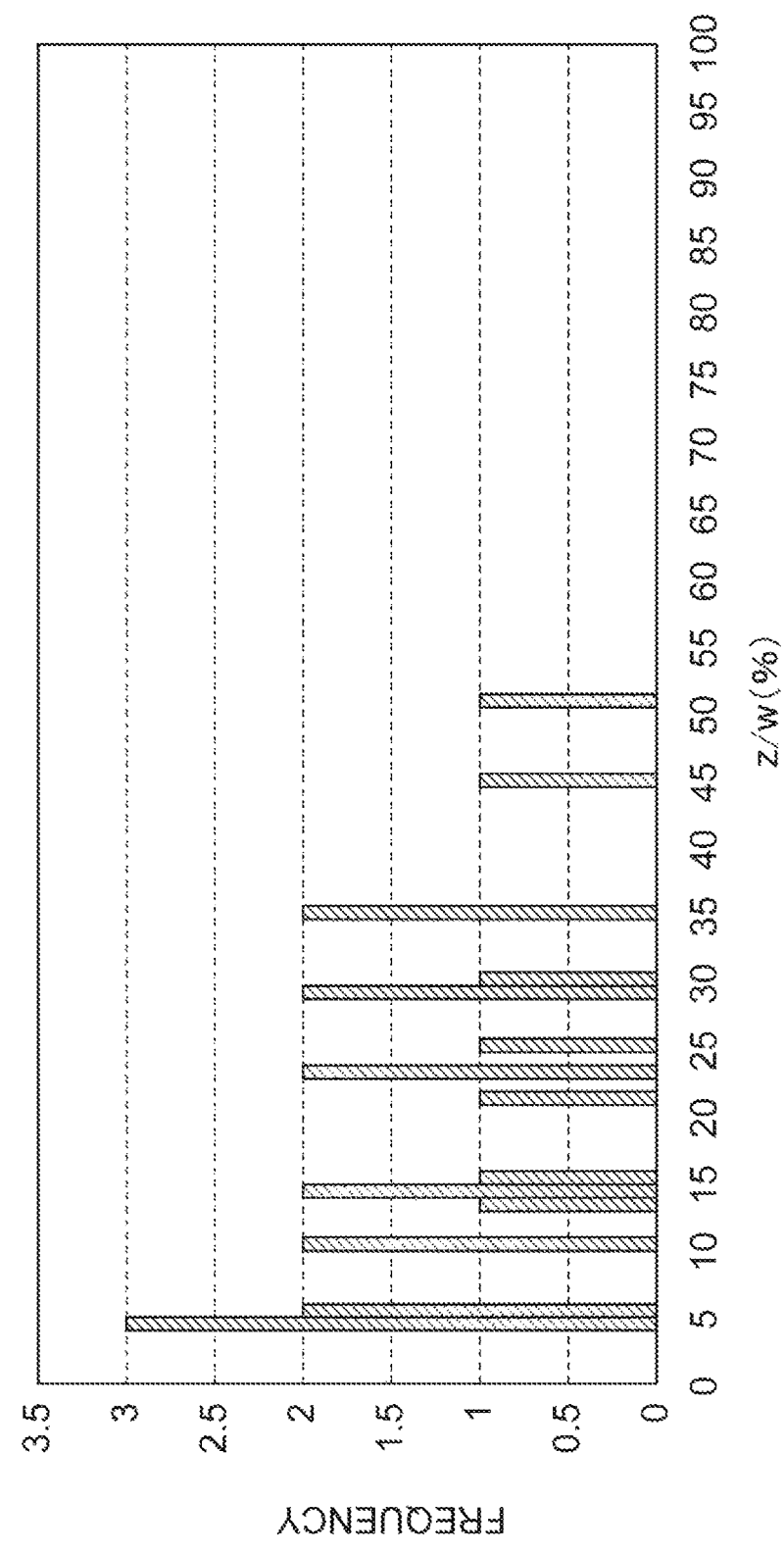
FIG. 2 is a diagram showing the distribution of the value of z/w (%) of naturally occurring fibroin.

Here, z/w in the naturally occurring fibroin will be described. First, as described above, it was checked by a method of taking an example of a fibroin whose amino acid sequence information is registered with the NCBI GenBank, and 663 kinds of fibroins (among these, there are 415 kinds of spider-derived fibroins) were extracted. Among all the extracted fibroins, z/w was calculated by the above-mentioned calculation method from the amino acid sequence of naturally occurring fibroin, which includes a domain sequence represented by Formula 1: $[(A)_n\text{ motif-REP}]_m$ and in which the content proportion of the amino acid sequence comprising GGX in the fibroin is 6% or less. The results are shown in FIG. 2. The axis of abscissa in FIG. 2 represents z/w (%), and the axis of ordinate represents the frequency. As is obvious from FIG. 2, z/w in the naturally occurring fibroin is less than 50.9% in all cases (the highest is 50.86%).

With regard to the modified fibroin of the second embodiment, z/w is preferably 50.9% or more, more preferably 56.1% or more, even more preferably 58.7% or more, still more preferably 70% or more, and further more preferably 80% or more. The upper limit of z/w is not particularly limited; however, for example, z/w may be 95% or less.

The modified fibroin of the second embodiment can be obtained by, for example, modifying naturally occurring fibroin such that at least a portion of the base sequence encoding a glycine residue is substituted from the gene sequence of cloned naturally occurring fibroin so as to encode another amino acid residue. At this time, as the glycine residue to be modified, one glycine residue in the GGX motif and the GPGXX motif ay be selected, and substitution may be carried out such that z/w is 50.9% or more. Furthermore, for example, the modified fibroin of the second embodiment can also be obtained by designing an amino acid sequence that satisfies the above-described embodiment from the amino acid sequence of naturally occurring fibroin, and chemically synthesizing a nucleic acid encoding the designed amino acid sequence. In all cases, modification of the amino acid sequence corresponding to having one or a plurality of amino acid residues substituted, deleted, inserted, and/or added may be further carried out, in addition to the modification corresponding to having a glycine residue in the REP from the amino acid sequence of naturally occurring fibroin substituted with another amino acid residue.

The above-described other amino acid residue is not particularly limited as long as it is an amino acid residue other than a glycine residue; however, hydrophobic amino acid residues such as a valine (V) residue, a leucine (L) residue, an isoleucine (I) residue, a methionine (M) residue, a proline (P) residue, a phenylalanine (F) residue, and a tryptophan (W) residue; and hydrophilic amino acid residues such as a glutamine (Q) residue, an asparagine (N) residue, a serine (S) residue, a lysine (K) residue, and a glutamic acid (E) residue are preferred, and a valine (V) residue, a leucine (L) residue, an isoleucine (I) residue, and a glutamine (Q) residue are more preferred, while a glutamine (Q) residue is even more preferred.

More specific examples of the modified fibroin of the second embodiment include modified fibroins including: (2-i) an amino acid sequence represented by SEQ ID NO:6 (Met-PRT380), SEQ ID NO:7 (Met-PRT410), SEQ ID NO:8 (Met-PRT468), or SEQ ID NO:9 (Met-PRT799), or (2-ii) an amino acid sequence having a sequence identity of 90% or higher with an amino acid sequence set forth in SEQ ID NO:6, SEQ ID NO:7, SEQ ID NO:8, or SEQ ID NO:9.

The modified fibroins of (2-i) will be described. The amino acid sequence set forth in SEQ ID NO:6 is an amino acid sequence in which all GGX's in the REP of an amino acid sequence set forth in SEQ ID NO:10 (Met-PRT313), which corresponds to naturally occurring fibroin, have been substituted with GQX. The amino acid sequence set forth in SEQ ID NO:7 is an amino acid sequence obtained by deleting every two $(A)_n$ motifs from the amino acid sequence set forth in SEQ ID NO:6 from the N-terminus side toward the C-terminus side, and inserting one $[(A)_n$ motif-REP] in front of the C-terminal sequence. The amino acid sequence set forth in SEQ ID NO:8 is an amino acid sequence obtained by inserting two alanine residues into the C-terminus side of each $(A)_n$ motif of the amino acid sequence set forth in SEQ ID NO:7, substituting some glutamine (Q) residues with serine (S) residues, and deleting some amino acids on the N-terminus side so that the molecular weight of the product becomes almost the same as the molecular weight of SEQ ID NO:7. The amino acid sequence set forth in SEQ ID NO:9 is an amino acid sequence in which a His tag has been added to the C-terminus of a sequence obtained by repeating, for four times, a region of twenty domain sequences (provided that several amino acid residues on the C-terminus side of this region have been substituted) present in the amino acid sequence set forth in SEQ ID NO:7.

The value of z/w for the amino acid sequence set forth in SEQ ID NO:10 (corresponding to naturally occurring fibroin) is 46.8%. The values of z/w for the amino acid sequence set forth in SEQ ID NO:6, the amino acid sequence set forth in SEQ ID NO:7, the amino acid sequence set forth in SEQ ID NO:8, and the amino acid sequence set forth in SEQ ID NO:9 are 58.7%, 70.1%, 66.1%, and 70.0%, respectively. Furthermore, the values of x/y at a jagged ratio (will be described below) of 1:1.8 to 11.3 for the amino acid sequences set forth in SEQ ID NO:10, SEQ ID NO:6, SEQ ID NO:7, SEQ ID NO:8, and SEQ ID NO:9 are 15.0%, 15.0%, 93.4%, 92.7%, and 89.3%, respectively.

The modified fibroin of (2-i) may comprise an amino acid sequence set forth in SEQ ID NO:6, SEQ ID NO:7, SEQ ID NO:8, or SEQ ID NO:9.

The modified fibroin of (2-ii) includes an amino acid sequence having a sequence identity of 90% or higher with an amino acid sequence set forth in SEQ ID NO:6, SEQ ID NO:7, SEQ ID NO:8, or SEQ ID NO:9. The modified fibroin of (2-ii) is also a protein including a domain sequence set forth in Formula 1: $[(A)_n$ motif-REP$]_m$. The sequence identity is preferably 95% or higher.

It is preferable that the modified fibroin of (2-ii) has a sequence identity of 90% or higher with an amino acid sequence set forth in SEQ ID NO:6, SEQ ID NO:7, SEQ ID NO:8, or SEQ ID NO:9, and when the total number of amino acid residues of an amino acid sequence comprising XGX (provided that X represents an amino acid residue other than glycine) included in the REP is designated as z, and the total number of amino acid residues in the REP in the domain sequence is designated as w, z/w is 50.9% or more.

The modified fibroin of the second embodiment may include a tag sequence at either or both of the N-terminus and the C-terminus. Thereby, isolation of the modified fibroin, fixation, detection, visualization, and the like are made possible.

As the tag sequence, for example, an affinity tag that utilizes the specific affinity with other molecules (binding property, affinity) may be mentioned. A specific example of the affinity tag may be a histidine tag (His tag). A His tag is a short peptide in which about 4 to 10 histidine residues are lined up, and since the His tag has a property of specifically binding to a metal ion such as nickel, the His tag can be utilized for the isolation of a modified fibroin by chelating metal chromatography. A specific example of the tag sequence may be, for example, an amino acid sequence set forth in SEQ ID NO: 11 (amino acid sequence including a His tag sequence and a hinge sequence).

Furthermore, a tag sequence such as glutathione-S-transferase (GST) that specifically binds to glutathione, or a maltose-binding protein (MBP) that specifically binds to maltose, can also be utilized.

Furthermore, an "epitope tag" that utilizes an antigen-antibody reaction can also be utilized. By adding a peptide exhibiting antigenicity (epitope) as a tag sequence, an antibody against this epitope can be bound. Examples of the epitope tag include a HA tag (peptide sequence of hemagglutinin of influenza virus), a myc tag, and a FLAG tag. By utilizing the epitope tag, the modified fibroin can be easily purified with high specificity.

Moreover, a tag sequence that has been made cleavable with a particular protease can also be used. By subjecting a protein adsorbed by means of this tag sequence to a protease treatment, a modified fibroin from which the tag sequence has been cleaved can be collected.

More specific examples of a modified fibroin including a tag sequence include a modified fibroin including: (2-iii) an amino acid sequence set forth in SEQ ID NO:12 (PRT380), SEQ ID NO:13 (PRT410), SEQ ID NO:14 (PRT468), or SEQ ID NO:15 (PRT799), or (2-iv) an amino acid sequence having a sequence identity of 90% or higher with an amino acid sequence set forth in SEQ ID NO:12, SEQ ID NO:13, SEQ ID NO:14, or SEQ ID NO:15.

The amino acid sequences set forth in SEQ ID NO:16 (PRT313), SEQ ID NO:13, SEQ ID NO:14, and SEQ ID NO:15 are products obtained by adding the amino acid sequence set forth in SEQ ID NO:11 (including a His tag sequence and a hinge sequence) to the N-terminus of the amino acid sequences set forth in SEQ ID NO:10, SEQ ID NO:6, SEQ ID NO:7, SEQ ID NO:8, and SEQ ID NO:9, respectively.

The modified fibroin of (2-iii) may comprise an amino acid sequence set forth in SEQ ID NO:12, SEQ ID NO:13, SEQ ID NO:14, or SEQ ID NO:15.

The modified fibroin of (2-iv) is a modified fibroin including an amino acid sequence having a sequence identity of 90% or higher with an amino acid sequence set forth in SEQ ID NO:12, SEQ ID NO:13, SEQ ID NO:14, or SEQ ID NO:15. The modified fibroin of (2-iv) is also a protein including a domain sequence represented by Formula 1: $[(A)_n$ motif-REP$]_m$. The sequence identity is preferably 95% or higher.

It is preferable that the modified fibroin of (2-iv) has a sequence identity of 90% or higher with an amino acid sequence set forth in SEQ ID NO:12, SEQ ID NO:13, SEQ ID NO:14, or SEQ ID NO:15, and when the total number of amino acid residues of the amino acid sequence comprising XGX (provided that X represents an amino acid residue other than glycine) included in the REP is designated as z, and the total number of amino acid residues in the REP in the domain sequence is designated as w, z/w is 50.9% or more.

The modified fibroin of the second embodiment may include a secretory signal for releasing a protein produced in a recombinant protein production system to the outside of a host. The sequence of the secretory signal can be appropriately set according to the type of the host.

The modified fibroin of the third embodiment is such that the domain sequence thereof has an amino acid sequence in which the content of the $(A)_n$ motif has been reduced as compared with naturally occurring fibroin. The domain sequence of the modified fibroin of the third embodiment can be said to have an amino acid sequence corresponding to at least having one or a plurality of the $(A)_n$ motifs deleted, as compared to naturally occurring fibroin.

The modified fibroin of the third embodiment may have an amino acid sequence corresponding to having 10% to 40% of the $(A)_n$ motifs deleted from naturally occurring fibroin.

The modified fibroin of the third embodiment may be such that the domain sequence thereof has an amino acid sequence corresponding to at least having one $(A)_n$ motif per one to three $(A)_n$ motifs deleted from the N-terminus side toward the C-terminus side, as compared to naturally occurring fibroin.

The modified fibroin of the third embodiment may also be such that the domain sequence thereof has an amino acid sequence corresponding to at least having two consecutive $(A)_n$ motifs deleted and one $(A)_n$ motif deleted repeatedly in this order from the N-terminus side toward the C-terminus side, as compared to naturally occurring fibroin.

The modified fibroin of the third embodiment may also be such that the domain sequence thereof has an amino acid sequence corresponding to at least having every two $(A)_n$ motifs deleted from the N-terminus side toward the C-terminus side.

The modified fibroin of the third embodiment may also include a domain sequence represented by Formula 1: $[(A)_n$ motif-REP$]_m$ and have an amino acid sequence in which when the numbers of amino acid residues in the REP's in two adjacent $[(A)_n$ motif-REP] units are sequentially compared from the N-terminus side toward the C-terminus side, and the number of amino acid residues in an REP having a smaller number of amino acid residues is designated as 1, and when the maximum value of the sum value obtained by adding the numbers of amino acid residues in two adjacent $[(A)_n$ motif-REP] units where the ratio of the number of amino acid residues in the other REP is 1.8 to 11.3 is designated as x, and the total number of amino acid residues in the domain sequence is designated as y, x/y is 20% or more, 30% or more, 40% or more, or 50% or more. The number of alanine residues with respect to the total number of amino acid residues in the $(A)_n$ motif may be 83% or more, preferably 86% or more, more preferably 90% or more, even more preferably 95% or more, and still more preferably 100% (meaning that the motif is composed only of alanine residues).

The method for calculating x/y will be described in more detail with reference to FIG. 1. FIG. 1 shows a domain sequence obtained by excluding the N-terminal sequence and the C-terminal sequence from a modified fibroin. This domain sequence has a sequence known as $(A)_n$ motif-first REP (50 amino acid residues)-$(A)_n$ motif-second REP (100 amino acid residues)-$(A)_n$ motif-third REP (10 amino acid residues)-$(A)_n$ motif-fourth REP (20 amino acid residues)-$(A)_n$ motif-fifth REP (30 amino acid residues)-$(A)_n$ motif from the N-terminus side (left-hand side).

Two adjacent $[(A)_n$ motif-REP] units sequentially selected from the N-terminus side toward the C-terminus side so as not to overlap. At this time, there may be an unselected $[(A)_n$ motif-REP]. FIG. 1 shows pattern 1 (a comparison of the first REP and the second REP, and a comparison of the third REP and the fourth REP), pattern 2 (a comparison of the first REP and the second REP, and a comparison of the fourth REP and the fifth REP), pattern 3 (a comparison of the second REP and the third REP, and a comparison of the fourth REP and the fifth REP), and pattern 4 (a comparison of the first REP and the second REP). Meanwhile, there are other selection methods in addition to these.

Next, for each of the patterns, the numbers of amino acid residues of various REP's in the two adjacent $[(A)_n$ motif-REP] units thus selected are compared. The comparison is carried out, when the unit having a smaller number of amino acid residues is designated as 1, by determining the ratio of the number of amino acid residues on the other unit. For example, in the case of the comparison of the first REP (50 amino acid residues) and the second REP (100 amino acid residues), when the first REP having a smaller number of amino acid residues is designated as 1, the ratio of the number of amino acid residues of the second REP is 100/50=2. Similarly, in the case of the comparison of the fourth REP (20 amino acid residues) and the fifth REP (30 amino acid residues), when the fourth REP having a smaller number of amino acid residues is designated as 1, the ratio of the number of amino acid residues of the fifth REP is 30/20=1.5.

In FIG. 1, a combination of $[(A)_n$ motif-REP] units in which when the unit having a smaller number of amino acid residues is designated as 1, the ratio of the number of amino acid residues of the other unit is 1.8 to 11.3, is indicated by a solid line. In the present specification, this ratio is referred to as jagged ratio. The combination of $[(A)_n$ motif-REP] units in which when the unit having a smaller number of amino acid residues is designated as 1, the ratio of the number of amino acid residues of the other unit is less than 1.8 or more than 11.3, is indicated by a broken line.

For each pattern, all the numbers of amino acid residues of two adjacent $[(A)_n$ motif-REP] units shown by a solid line are summed up (not only REP's but also the number of amino acid residues of the $(A)_n$ motifs). Then, the sum values obtained by summing up are compared, and the sum value of the pattern whose sum value is the maximum (maximum value of the sum value) is designated as x. In the example shown in FIG. 1, the sum value of pattern 1 is the maximum.

Next, x/y (%) can be calculated by dividing x by y, which is the total number of amino acid residues of the domain sequence.

With respect to the modified fibroin of the third embodiment, x/y is preferably 50% or more, more preferably 60% or more, even more preferably 65% or more, still more preferably 70% or more, further more preferably 75% or more, and particularly preferably 80% or more. The upper limit of x/y is not particularly limited and may be, for example 100% or less. In a case in which the jagged ratio is 1:1.9 to 11.3, x/y is preferably 89.6% or more; in a case in which the jagged ratio is 1:1.8 to 3.4, x/y is preferably 77.1% or more; in a case in which the jagged ratio is 1:1.9 to 8.4, x/y is preferably 75.9% or more; and in a case in which the jagged ratio is 1:1.9 to 4.1, x/y is preferably 64.2% or more.

In a case in which the modified fibroin of the third embodiment is a modified fibroin in which at least seven of a plurality of $(A)_n$ motifs present in the domain sequence are composed only of alanine residues, x/y is preferably 46.4% or more, more preferably 50% or more, even more preferably 55% or more, still more preferably 60% or more, further more preferably 70% or more, and particularly preferably 80% or more. The upper limit of x/y is not particularly limited and may be 100% or less.

Here, x/y in naturally occurring fibroin will be described. First, as described above, fibroins whose amino acid sequence information is registered with the NCBI GenBank were checked by the method mentioned as an example, and 663 kinds of fibroins (among these, there are 415 kinds of spider-derived fibroins) were extracted. Among all the fibroins thus extracted, from the amino acid sequence of naturally occurring fibroin composed of a domain sequence represented by Formula 1: $[(A)_n$ motif-REP$]_m$, x/y was calculated by the above-mentioned calculation method. The results of a case in which the jagged ratio was 1:1.9 to 4.1 are presented in FIG. 3.

Figure 3:
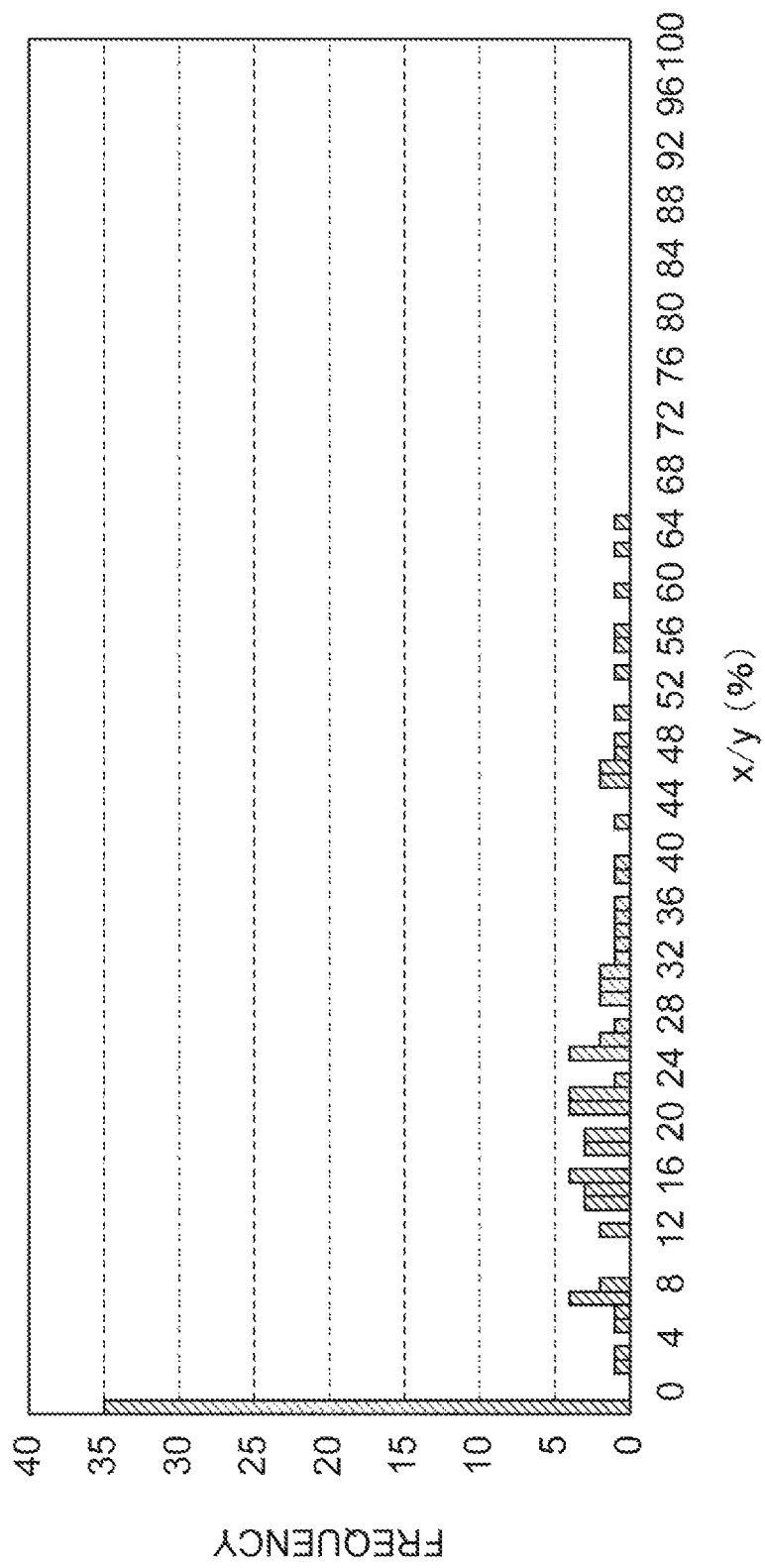
FIG. 3 is a diagram showing the distribution of the value of x/y (%) of naturally occurring fibroin.

The axis of abscissa in FIG. 3 represents x/y (%), and the axis of ordinate represents the frequency. As is obvious from FIG. 3, x/y in the naturally occurring fibroin is less than 64.2% in all cases (the highest value is 64.14%).

The modified fibroin of the third embodiment can be obtained by, for example, deleting one or a plurality of sequences encoding the $(A)_n$ motif from the gene sequence of cloned naturally occurring fibroin such that x/y is 64.2% or more. Furthermore, for example, the modified fibroin can also be obtained by designing an amino acid sequence corresponding to having one or a plurality of $(A)_n$ motifs deleted from the amino acid sequence of naturally occurring fibroin such that x/y is 64.2% or more, and chemically synthesizing a nucleic acid encoding the designed amino acid sequence. In all cases, modification of an amino acid sequence corresponding to having one or a plurality of amino acid residues substituted, deleted, inserted, and/or added may be further carried out in addition to the modification corresponding to having the $(A)_n$ motif deleted from the amino acid sequence of naturally occurring fibroin.

More specific examples of the modified fibroin of the third embodiment include: (3-i) an amino acid sequence set forth in SEQ ID NO:17 (Met-PRT399), SEQ ID NO:7 (Met-PRT410), SEQ ID NO:8 (Met-PRT468), or SEQ ID NO:9 (Met-PRT799), or (3-ii) an amino acid sequence having a sequence identity of 90% or higher with an amino acid sequence set forth in SEQ ID NO:17, SEQ ID NO:7, SEQ ID NO:8, or SEQ ID NO:9.

The modified fibroin of (3-i) will be described. The amino acid sequence set forth in SEQ ID NO:17 is an amino acid sequence obtained by deleting every two $(A)_n$ motifs from the amino acid sequence set forth in SEQ ID NO:10 (Met-PRT313), which corresponds to naturally occurring fibroin, from the N-terminus side toward the C-terminus side, and inserting one $[(A)_n$ motif-REP] in front of the C-terminal sequence. The amino acid sequence set forth in SEQ ID NO:7, SEQ ID NO:8, or SEQ ID NO:9 is as described in connection with the modified fibroin of the second embodiment.

The value of x/y for the amino acid sequence set forth in SEQ ID NO:10 (corresponding to naturally occurring fibroin) at a jagged ratio of 1:1.8 to 11.3 is 15.0%. The values of x/y for the amino acid sequence set forth in SEQ ID NO:17 and the amino acid sequence set forth in SEQ ID NO:7 are both 93.4%. The value of x/y for the amino acid sequence set forth in SEQ ID NO:8 is 92.7%. The value of x/y for the amino acid sequence set forth in SEQ ID NO:9 is 89.3%. The values of z/w for the amino acid sequences set forth in SEQ ID NO:10, SEQ ID NO:17, SEQ ID NO:7, SEQ ID NO:8, and SEQ ID NO:9 are 46.8%, 56.2%, 70.1%, 66.1%, and 70.0%, respectively.

The modified fibroin of (3-i) may comprise an amino acid sequence set forth in SEQ ID NO:17, SEQ ID NO:7, SEQ ID NO:8, or SEQ ID NO:9.

The modified fibroin of (3-ii) includes an amino acid sequence having a sequence identity of 90% or higher with an amino acid sequence set forth in SEQ ID NO:17, SEQ ID NO:7, SEQ ID NO:8, or SEQ ID NO:9. The modified fibroin of (3-ii) is also a protein including a domain sequence represented by Formula 1: $[(A)_n$ motif-REP$]_m$. The sequence identity is preferably 95% or higher.

It is preferable that the modified fibroin of (3-ii) has a sequence identity of 90% or higher with an amino acid sequence set forth in SEQ ID NO:17, SEQ ID NO:7, SEQ ID NO:8, or SEQ ID NO:9, and when the numbers of amino acid residues in the REP's in two adjacent $[(A)_n$ motif-REP] units are sequentially compared from the N-terminus side toward the C-terminus side, and the number of amino acid residues in an REP having a smaller number of amino acid residues is designated as 1, and when the maximum value of the sum value obtained by adding the numbers of amino acid residues in two adjacent $[(A)_n$ motif-REP]units where the ratio of the number of amino acid residues in the other REP is 1.8 to 11.3 (jagged ratio is 1:1.8 to 11.3) is designated as x, and the total number of amino acid residues in the domain sequence is designated as y, x/y is 64.2% or more.

The modified fibroin of the third embodiment may be such that either or both of the N-terminus and the C-terminus include the above-mentioned tag sequence.

As a more specific example of a modified fibroin including a tag sequence, a modified fibroin including: (3-iii) an amino acid sequence set forth in SEQ ID NO:18 (PRT399), SEQ ID NO:13 (PRT410), SEQ ID NO:14 (PRT468), or SEQ ID NO:15 (PRT799); or (3-iv) an amino acid sequence having a sequence identity of 90% or higher with an amino acid sequence set forth in SEQ ID NO:18, SEQ ID NO:13, SEQ ID NO:14, or SEQ ID NO:15.

The amino acid sequences set forth in SEQ ID NO:18, SEQ ID NO:13, SEQ ID NO:14, and SEQ ID NO:15 are products obtained by adding the amino acid sequence set forth in SEQ ID NO:11 (including His tag sequence and a hinge sequence) to the N-terminus of the amino acid sequences set forth in SEQ ID NO:17, SEQ ID NO:7, SEQ ID NO:8, and SEQ ID NO:9, respectively.

The modified fibroin of (3-iii) may comprise an amino acid sequence set forth in SEQ ID NO:18, SEQ ID NO:13, SEQ ID NO:14, or SEQ ID NO:15.

The modified fibroin of (3-iv) includes an amino acid sequence having a sequence identity of 90% or higher with an amino acid sequence set forth in SEQ ID NO:18, SEQ ID NO:13, SEQ ID NO:14, or SEQ ID NO:15. The modified fibroin of (3-iv) is also a protein including a domain sequence represented by Formula 1: $[(A)_n$ motif-REP$]_m$. The sequence identity is preferably 95% or higher.

It is preferable that the modified fibroin of (3-iv) has a sequence identity of 90% or higher with an amino acid sequence set forth in SEQ ID NO:18, SEQ ID NO:13, SEQ ID NO:14, or SEQ ID NO:15, and when the numbers of amino acid residues in the REP's of two adjacent $[(A)_n$ motif-REP] unit are sequentially compared from the N-terminus side toward the C-terminus side, and the number of amino acid residues in an REP having a smaller number of amino acid residues is designated as 1, and when the maximum value of the sum value obtained by adding the numbers of amino acid residues in two adjacent [(A)$_n$ motif-REP]units where the ratio of the number of amino acid residues in the other REP is 1.8 to 11.3 is designated as x, and the total number of amino acid residues in the domain sequence is designated as y, x/y is 64.2% or more.

The modified fibroin of the third embodiment may include a secretory signal for releasing a protein produced in a recombinant protein production system to the outside of a host. The sequence of the secretory signal can be appropriately set according to the type of the host.

The modified fibroin of the fourth embodiment is such that the domain sequence thereof has an amino acid sequence in which the content of glycine residues has been reduced, in addition to having the content of the (A)$_n$ motif reduced, as compared to naturally occurring fibroin. The domain sequence of the modified fibroin of the fourth embodiment can be said to have an amino acid sequence corresponding to at least having one or a plurality of glycine residues in the REP substituted with another amino acid residue(s), in addition to at least having one or a plurality of the (A)$_n$ motifs deleted, as compared to naturally occurring fibroin. That is, the modified fibroin of the fourth embodiment is a modified fibroin having combined features of the modified fibroin of the second embodiment and the modified fibroin of the third embodiment. Specific embodiments and the like are as described in connection with the modified fibroin of the second embodiment and the modified fibroin of the third embodiment.

As a more specific example of the modified fibroin of the fourth embodiment, a modified fibroin including: (4-i) an amino acid sequence set forth in SEQ ID NO:7 (Met-PRT410), SEQ ID NO:8 (Met-PRT468), SEQ ID NO:9 (Met-PRT799), SEQ ID NO:13 (PRT410), SEQ ID NO:14 (PRT468), or SEQ ID NO:15 (PRT799); or (4-ii) an amino acid sequence having a sequence identity of 90% or higher with an amino acid sequence set forth in SEQ ID NO:7, SEQ ID NO:8, SEQ ID NO:9, SEQ ID NO:13, SEQ ID NO:14, or SEQ ID NO:15, may be mentioned. Specific embodiments of the modified fibroin including an amino acid sequence set forth in SEQ ID NO:7, SEQ ID NO:8, SEQ ID NO:9, SEQ ID NO:13, SEQ ID NO:14, SEQ ID NO:15 are as described above.

The modified fibroin of the fifth embodiment may be such that the domain sequence thereof has an amino acid sequence that includes a region in which the hydropathy index is locally large, the amino acid sequence corresponding to having one or a plurality of amino acid residues in the REP substituted with an amino acid residue(s) having a large hydropathy index, and/or having one or a plurality of amino acid residues having a large hydropathy index inserted into the REP, as compared to naturally occurring fibroin.

It is preferable that the region in which the hydropathy index is locally large is composed of two to four consecutive amino acid residues.

It is more preferable that the above-mentioned amino acid residue having a large hydropathy index is an amino acid residue selected from isoleucine (I), valine (V), leucine (L), phenylalanine (F), cysteine (C), methionine (M), and alanine (A).

The modified fibroin of the fifth embodiment may further have a modification of an amino acid sequence corresponding to having one or a plurality of amino acid residues substituted, deleted, inserted, and/or added as compared to naturally occurring fibroin, in addition to a modification corresponding to having one or a plurality of amino acid residues in the REP substituted with an amino acid residue having a large hydropathy index, and/or having one or a plurality of amino acid residues having a large hydropathy index inserted into the REP, as compared to naturally occurring fibroin.

The modified fibroin of the fifth embodiment can be obtained by, for example, substituting one or a plurality of hydrophilic amino acid residues (for example, amino acid residues having a negative hydropathy index) in the REP from the gene sequence of cloned naturally occurring fibroin with a hydrophobic amino acid residue(s) (for example, amino acid residues having a positive hydropathy index), and/or inserting one or a plurality of hydrophobic amino acid residues into the REP. Furthermore, for example, the modified fibroin of the fifth embodiment can also be obtained by designing an amino acid sequence corresponding to having one or a plurality of hydrophilic amino acid residues in the REP from the amino acid sequence of naturally occurring fibroin substituted with hydrophobic amino acid residue(s) and/or having one or a plurality of hydrophobic amino acid residues inserted into the REP, and chemically synthesizing a nucleic acid encoding the designed amino acid sequence. In all cases, a modification of an amino acid sequence corresponding to having one or a plurality of amino acid residues substituted, deleted, inserted, and/or added may be further carried out in addition to the modification of the amino acid sequence corresponding to having one or a plurality of hydrophilic amino acid residues in the REP from the amino acid sequence of naturally occurring fibroin substituted with hydrophobic amino acid residue(s), and/or having one or a plurality of hydrophobic amino acid residues inserted into the REP.

The modified fibroin of the fifth embodiment may also include a domain sequence represented by Formula 1: [(A)$_n$ motif-REP]$_m$, and have an amino acid sequence in which for all the REP's included in a sequence obtained by excluding the sequence from the (A)$_n$ motif located on the furthermost C-terminus side to the C-terminus of the domain sequence from the domain sequence, when the total number of amino acid residues included in a region in which the average value of the hydropathy indices of four consecutive amino acid residues is 2.6 or more is designated as p, and the total number of amino acid residues included in a sequence obtained by excluding the sequence from the (A)$_n$ motif located on the furthermost C-terminus side to the C-terminus of the domain sequence from the domain sequence is designated as q, p/q is 6.2% or more.

With regard to the hydropathy index of an amino acid residue, a known index (Hydropathy index: Kyte J, & Doolittle R (1982) "A simple method for displaying the hydropathic character of a protein", J. Mol. Biol., 157, pp. 105-132) is used. Specifically, the hydropathy indices of various amino acids (hydropathy index; hereinafter, described as "HI") are as shown in the following Table 1.

TABLE 1

| Amino acid | HI |
| --- | --- |
| Isoleucine (Ile) | 4.5 |
| Valine (Val) | 4.2 |
| Leucine (Leu) | 3.8 |
| Phenylalanine (Phe) | 2.8 |
| Cysteine (Cys) | 2.5 |
| Methionine (Met) | 1.9 |
| Alanine (Ala) | 1.8 |
| Glycine (Gly) | −0.4 |

TABLE 1-continued

| Amino acid | HI |
|---|---|
| Threonine (Thr) | −0.7 |
| Serine (Ser) | −0.8 |
| Tryptophan (Trp) | −0.9 |
| Tyrosine (Tyr) | −1.3 |
| Proline (Pro) | −1.6 |
| Histidine (His) | −3.2 |
| Asparagine (Asn) | −3.5 |
| Aspartic acid (Asp) | −3.5 |
| Glutamine (Gln) | −3.5 |
| Glutamic acid (Glu) | −3.5 |
| Lysine (Lys) | −3.9 |
| Arginine (Arg) | −4.5 |

A method for calculating p/q will be described in more detail. For the calculation, a sequence obtained by excluding the sequence from the $(A)_n$ motif located on the furthermost C-terminus side to the C-terminus of the domain sequence from a domain sequence represented by Formula 1: $[(A)_n$ motif-REP$]_m$ (hereinafter, referred to as "sequence A") is used. First, for all the REP's included in the sequence A, the average value of the hydropathy indices of four consecutive amino acid residues is calculated. The average value of the hydropathy index is determined by dividing the total sum of HI of various amino acid residues include in four consecutive amino acid residues by 4 (number of amino acid residues). The average value of the hydropathy index is determined for all four consecutive amino acid residues (each amino acid residue is used for the calculation of the average values for one to four times). Next, a region in which the average value of the hydropathy indices of four consecutive amino acid residues is 2.6 or more is specified. Even in a case in which a certain amino acid residue corresponds to a plurality of "four consecutive amino acid residues whose average value of the hydropathy indices is 2.6 or more", the amino acid residue is included as one amino acid residue in the region. Then, the total number of amino acid residues included in this region is p. Furthermore, the total number of amino acid residues included in the sequence A is q.

Figure 4:
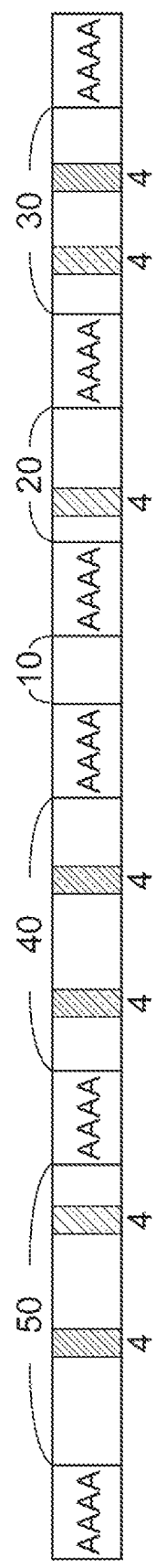
FIG. 4 is a schematic diagram showing the domain sequence of a modified fibroin according to an embodiment.

For example, in a case in which the "four consecutive amino acid residues whose average value of the hydropathy indices is 2.6 or more" have been extracted at 20 sites (no overlap), in a region in which the average value of the hydropathy indices of four consecutive amino acid residues is 2.6 or more, twenty sets of four consecutive amino acid residues (no overlap) are included, and p is such that 20×4=80. Furthermore, for example, in a case in which only one amino acid residue is present overlappingly in two sets of the "four consecutive amino acid residues whose average value of the hydropathy indices is 2.6 or more", in a region in which the average value of the hydropathy indices of four consecutive amino acid residues is 2.6 or more, seven amino acid residues are included (p=2×4−1=7. "−1" is the subtraction of an overlapping portion). For example, in the case of the domain sequence shown in FIG. 4, since there are seven sets of the "four consecutive amino acid residues whose average value of the hydropathy indices is 2.6 or more" without overlap, p is such that 7×4=28. Furthermore, for example, in the case of the domain sequence shown in FIG. 4, q is such that 4+50+4+40+4+10+4+20+4+30=170 (the $(A)_n$ motif existing at the end of the C-terminus side is not included). Next, p is dived by q, and thereby p/q (%) can be calculated. In the case of FIG. 4, 28/170=16.47% is obtained.

For the modified fibroin of the fifth embodiment, p/q is preferably 6.2% or more, more preferably 7% or more, even more preferably 10% or more, still more preferably 20% or more, and further more preferably 30% or more. The upper limit of p/q is not particularly limited; however, for example, the ratio may be 45% or less.

The modified fibroin of the fifth embodiment can be obtained by, for example, modifying the amino acid sequence of cloned naturally occurring fibroin into an amino acid sequence including a region in which the hydropathy index is locally large, by substituting one or a plurality of hydrophilic amino acid residues (for example, amino acid residues having a negative hydropathy index) in the REP with hydrophobic amino acid residues (for example, amino acid residues having a positive hydropathy index) so as to satisfy the above-described condition for p/q, and/or inserting one or a plurality of hydrophobic amino acid residues into the REP. Furthermore, for example, the modified fibroin of the fifth embodiment can also be obtained by designing an amino acid sequence that satisfies the above-described condition for p/q from the amino acid sequence of naturally occurring fibroin, and chemically synthesizing a nucleic acid encoding the designed amino acid sequence. In all cases, a modification corresponding to having one or a plurality of amino acid residues substituted, deleted, inserted, and/or added may be further carried out, in addition to the modification corresponding to having one or a plurality of amino acid residues in the REP substituted with an amino acid residue(s) having a large hydropathy index, and/or having one or a plurality of amino acid residues having a large hydropathy index inserted into the REP, as compared to naturally occurring fibroin.

The amino acid residue having a large hydropathy index is not particularly limited; however, isoleucine (I), valine (V), leucine (L), phenylalanine (F), cysteine (C), methionine (M), and alanine (A) are preferred, and valine (V), leucine (L), and isoleucine (I) are more preferred.

As a more specific example of the modified fibroin of the fifth embodiment, a modified fibroin including: (5-i) an amino acid sequence set forth in SEQ ID NO:19 (Met-PRT720), SEQ ID NO:20 (Met-PRT665), or SEQ ID NO:21 (Met-PRT666), or (5-ii) an amino acid sequence having a sequence identity of 90% or higher with an amino acid sequence set forth in SEQ ID NO:19, SEQ ID NO:20, or SEQ ID NO:21, may be mentioned.

The modified fibroin of (5-i) will be described. The amino acid sequence set forth in SEQ ID NO:19 is an amino acid sequence obtained by inserting an amino acid sequence each comprising three amino acid residues (VLI) at two sites in every other REP in the amino acid sequence set forth in SEQ ID NO:7 (Met-PRT410), and deleting some amino acids on the C-terminus side such that the molecular weight of the resultant to be almost similar to the molecular weight of the amino acid sequence set forth in SEQ ID NO:7. The amino acid sequence set forth in SEQ ID NO:20 is an amino acid sequence obtained by inserting an amino acid sequence each comprising three amino acid residues (VLI) at one site in every other REP in the amino acid sequence set forth in SEQ ID NO:8 (Met-PRT468). The amino acid sequence set forth in SEQ ID NO:21 is an amino acid sequence obtained by inserting an amino acid sequence each comprising three amino acid residues (VLI) at two sites in every other REP in the amino acid sequence set forth in SEQ ID NO:8.

The modified fibroin of (5-i) may comprise an amino acid sequence set forth in SEQ ID NO:19, SEQ ID NO:20, or SEQ ID NO:21.

The modified fibroin of (5-ii) includes an amino acid sequence having a sequence identity of 90% or higher with an amino acid sequence set forth in SEQ ID NO:19, SEQ ID NO:20, or SEQ ID NO:21. The modified fibroin of (5-ii) is also a protein including a domain sequence set forth in Formula 1: $[(A)_n$ motif-REP$]_m$. The sequence identity is preferably 95% or higher.

It is preferable that the modified fibroin of (5-ii) has a sequence identity of 90% or higher with an amino acid sequence set forth in SEQ ID NO:19, SEQ ID NO:20, or SEQ ID NO:21 and for all the REP's included in a sequence obtained by excluding the sequence from the $(A)_n$ motif located on the furthermost C-terminus side to the C-terminus of the domain sequence from the domain sequence, when the total number of amino acid residues included in a region in which the average value of the hydropathy indices of four consecutive amino acid residues is 2.6 or more is designated as p, and the total number of amino acid residues included in a sequence obtained by excluding the sequence from the $(A)_n$ motif located at the furthermost C-terminus side to the C-terminus of the domain sequence from the domain sequence is designated as q, p/q is 6.2% or more.

The modified fibroin of the fifth embodiment may include a tag sequence at either or both of the N-terminus and the C-terminus.

As a more specific example of a modified fibroin including a tag sequence, a modified fibroin including: (5-iii) an amino acid sequence set forth in SEQ ID NO:22 (PRT720), SEQ ID NO:23 (PRT665), or SEQ ID NO:24 (PRT666), or (5-iv) an amino acid sequence having a sequence identity of 90% or higher with the amino acid sequence set forth in SEQ ID NO:22, SEQ ID NO:23, or SEQ ID NO:24, may be mentioned.

The amino acid sequences set forth in SEQ ID NO:22, SEQ ID NO:23, and SEQ ID NO:24 are amino acid sequences obtained by adding the amino acid sequence set forth in SEQ ID NO: 11 (including a His tag sequence and a hinge sequence) to the N-terminus of the amino acid sequences set forth in SEQ ID NO:19, SEQ ID NO:20, and SEQ ID NO:21, respectively.

The modified fibroin of (5-iii) may comprise an amino acid sequence set forth in SEQ ID NO:22, SEQ ID NO:23, or SEQ ID NO:24.

The modified fibroin of (5-iv) includes an amino acid sequence having a sequence identity of 90% or higher with an amino acid sequence set forth in SEQ ID NO:22, SEQ ID NO:23, or SEQ ID NO:24. The modified fibroin of (5-iv) is also a protein including a domain sequence represented by Formula 1: $[(A)_n$ motif-REP$]_m$. The sequence identity is preferably 95% or higher.

It is preferable that the modified fibroin of (5-iv) has a sequence identity of 90% or higher with an amino acid sequence set forth in SEQ ID NO:22, SEQ ID NO:23, or SEQ ID NO:24, and for all the REP's included in a sequence obtained by excluding the sequence from the $(A)_n$ motif located on the furthermost C-terminus side to the C-terminus of the domain sequence from the domain sequence, when the total number of amino acid residues included in a region in which the average value of the hydropathy indices of four consecutive amino acid residues is 2.6 or more is designated as p, and the total number of amino acid residues included in a sequence obtained by excluding the sequence from the $(A)_n$ motif located on the furthermost C-terminus side to the C-terminus of the domain sequence from the domain sequence is designated as q, p/q is 6.2% or more.

The modified fibroin of the fifth embodiment may include a secretory signal for releasing a protein produced in a recombinant protein production system to the outside of a host. The sequence of the secretory signal can be appropriately set according to the type of the host.

The modified fibroin of the sixth embodiment has an amino acid sequence in which the content of glutamine residues has been reduced, as compared to naturally occurring fibroin.

Regarding the modified fibroin of the sixth embodiment, it is preferable that at least one motif selected from a GGX motif and a GPGXX motif is included in the amino acid sequence of REP.

In a case in which the modified fibroin of the sixth embodiment includes a GPGXX motif in REP, the GPGXX motif percentage content is usually 1% or more, desirably 5% or more, and preferably 10% or more. The upper limit of the GPGXX motif percentage content is not particularly limited, and the percentage content may be 50% or less, or may be 30% or less.

According to the present specification, the "GPGXX motif percentage content" is a value calculated by the following method.

With regard to a fibroin (modified fibroin or naturally occurring fibroin) including a domain sequence represented by Formula 1: $[(A)_n$ motif-REP$]_m$ or Formula 2: $[(A)_n$ motif-REP$]_m$-$(A)_n$ motif for all the REP's included in a sequence excluding the sequence from the $(A)_n$ motif located on the furthermost C-terminus side to the C-terminus of the domain sequence from the domain sequence, when the number at which the total number of the numbers of GPGXX motifs included in the region becomes three times (that is, corresponding to the total number of G and P in the GPGXX motif) is designated as s, and the total number of amino acid residues of all the REP's obtained by excluding the sequence from the $(A)_n$ motif located on the furthermost C-terminus side to the C-terminus of the domain sequence from the domain sequence and further excluding the $(A)_n$ motif is designated as t, the GPGXX motif percentage content is calculated as s/t.

With regard to the calculation of the GPGXX motif percentage content, "a sequence obtained by excluding the sequence from the $(A)_n$ motif located on the furthermost C-terminus side to the C-terminus of the domain sequence from the domain sequence" is the target of the calculation because in the "sequence from the $(A)_n$ motif located on the furthermost C-terminus side to the C-terminus of the domain sequence" (sequence corresponding to REP), a sequence having low correlation with a sequence characteristic of fibroin may be included, and in a case in which m is small (that is, in a case in which the domain sequence is short), since this affects the results of calculation of the GPGXX motif percentage content, this influence should be eliminated. Incidentally, in a case in which a "GPGXX motif" is located at the C-terminus of REP, even in a case in which "XX" is, for example, "AA", the motif is dealt with as "GPGXX motif".

Figure 5:
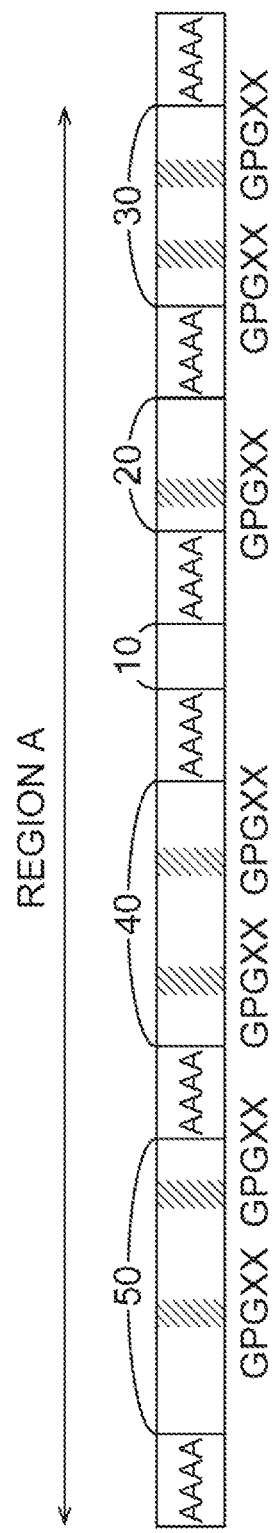
FIG. 5 is a schematic diagram showing the domain sequence of a modified fibroin according to an embodiment.

FIG. 5 is a schematic diagram showing the domain sequence of a modified fibroin. A method for calculating the GPGXX motif percentage content will be specifically described with reference to FIG. 5. First, in the domain sequence ("$[(A)_n$ motif-REP$]_m$-$(A)_n$ motif" type) of the modified fibroin shown in FIG. 5, since all REP's are included in the "sequence obtained by excluding the sequence from the $(A)_n$ motif located on the furthermost C-terminus side to the C-terminus of the domain sequence" (in FIG. 5, the sequence represented by "region A"), the number of the GPGXX motif for calculating s is 7, and s is such that 7×3=21. Similarly, since all REP's are included in the "sequence obtained by excluding the sequence from the $(A)_n$ motif located on the furthermost C-terminus side to the C-terminus of the domain sequence from the domain sequence" (in FIG. 5, the sequence represented by "region A"), the total number t of amino acid residues of all the REP's obtained by further excluding the $(A)_n$ motif from the sequence is 50+40+10+20+30=150. Next, s is divided by t, and thereby s/t (%) can be calculated. In the case of the modified fibroin of FIG. 5, the value of the ratio is 21/150=14.0%.

The modified fibroin of the sixth embodiment is such that the glutamine residue percentage content is preferably 9% or less, more preferably 7% or less, even more preferably 4% or less, and particularly preferably 0%.

According to the present specification, the "glutamine residue percentage content" is a value calculated by the following method.

With regard to a fibroin (modified fibroin or naturally occurring fibroin) including a domain sequence represented by Formula 1: $[(A)_n$ motif-REP$]_m$ or Formula 2: $[(A)_n$ motif-REP$]_m$-$(A)_n$ motif for all the REP's included in a sequence obtained by excluding the sequence from the $(A)_n$ motif located on the furthermost C-terminus side to the C-terminus of the domain sequence from the domain sequence (sequence corresponding to "region A" in FIG. 5), the total number of glutamine residues included in that region is designated as u, and the total number of amino acid residues in all the REP's obtained by excluding the sequence from the $(A)_n$ motif located on the furthermost C-terminus side to the C-terminus of the domain sequence and further excluding the $(A)_n$ motif is designated as t, the glutamine residue percentage content is calculated by u/t. For the calculation of the glutamine residue percentage content, the reason of targeting the "sequence excluding the sequence from the $(A)_n$ motif located on the furthermost C-terminus side to the C-terminus of the domain sequence from the domain sequence" is similar to the above-mentioned reason.

The modified fibroin of the sixth embodiment may be such that the domain sequence thereof has an amino acid sequence corresponding to having one or a plurality of glutamine residues in the REP deleted, or having one or a plurality of glutamine residues in the REP substituted with another amino acid residue(s), as compared to naturally occurring fibroin.

The "other amino acid residue" may be an amino acid residue other than a glutamine residue; however, it is preferable that the other amino acid residue is an amino acid residue having a larger hydropathy index than a glutamine residue. The hydropathy indices of amino acid residues are as shown in Table 1.

As shown in Table 1, as an amino acid residue having a larger hydropathy index than a glutamine residue, an amino acid residue selected from isoleucine (I), valine (V), leucine (L), phenylalanine (F), cysteine (C), methionine (M), alanine (A), glycine (G), threonine (T), serine (S), tryptophan (W), tyrosine (Y), proline (P), and histidine (H) may be mentioned. Among these, an amino acid residue selected from isoleucine (I), valine (V), leucine (L), phenylalanine (F), cysteine (C), methionine (M), and alanine (A) is more preferred, and an amino acid residue selected from isoleucine (I), valine (V), leucine (L), and phenylalanine (F) is more preferred.

With regard to the modified fibroin of the sixth embodiment, the degree of hydrophobicity of REP is preferably −0.8 or higher, more preferably −0.7 or higher, even more preferably 0 or higher, still more preferably 0.3 or higher, and particularly preferably 0.4 or higher. The upper limit of the degree of hydrophobicity of REP is not particularly limited, and the degree of hydrophobicity may be 1.0 or lower or may be 0.7 or lower.

According to the present specification, the "degree of hydrophobicity of REP" is a value calculated by the following method.

With regard to a fibroin (modified fibroin or naturally occurring fibroin) including a domain sequence represented by Formula 1: $[(A)_n$ motif-REP$]_m$ or Formula 2: $[(A)_n$ motif-REP$]_m$-$(A)_n$ motif for all the REP's included in a sequence obtained by excluding the sequence from the $(A)_n$ motif located on the furthermost C-terminus side to the C-terminus of the domain sequence from the domain sequence (sequence corresponding to "region A" in FIG. 5), when the total sum of the hydropathy indices of various amino acid residues in the region is designated as v, and the total number of amino acid residues in all the REP's obtained by excluding the sequence from the $(A)_n$ motif located on the furthermost C-terminus side to the C-terminus of the domain sequence from the domain sequence and further excluding the $(A)_n$ motif is designated as t, the degree of hydrophobicity of REP is calculated as v/t. For the calculation of the degree of hydrophobicity of REP, the reason for targeting the "sequence obtained by excluding the sequence from the $(A)_n$ motif located on the furthermost C-terminus side to the C-terminus of the domain sequence from the domain sequence" is similar to the reason described above.

The modified fibroin of the sixth embodiment may be such that the domain sequence thereof has a modification of the amino acid sequence corresponding to further having one or a plurality of amino acid residues substituted deleted, inserted, and/or added, in addition to the modification of having one or a plurality of glutamine residues in the REP deleted, and/or having one or a plurality of glutamine residues in the REP substituted with another amino acid residue(s), as compared to naturally occurring fibroin.

The modified fibroin of the sixth embodiment can be obtained by, for example, deleting one or a plurality of glutamine residues in the REP from the gene sequence of cloned naturally occurring fibroin, and/or substituting one or a plurality of glutamine residues in the REP with another amino acid residue(s). Furthermore, the modified fibroin of the sixth embodiment can also be obtained by, for example, deleting one or a plurality of glutamine residues in the REP from the amino acid sequence of naturally occurring fibroin, and/or designing an amino acid sequence corresponding to having one or a plurality of glutamine residues in the REP substituted with another amino acid residue(s), and chemically synthesizing a nucleic acid encoding the designed amino acid sequence.

As a more specific example of the modified fibroin of the sixth embodiment, (6-i) a modified fibroin including an amino acid sequence set forth in SEQ ID NO:25 (M_PRT888), SEQ ID NO:26 (M_PRT965), SEQ ID NO:27 (M_PRT889), SEQ ID NO:28 (M_PRT916), SEQ ID NO:29 (M_PRT918), SEQ ID NO:30 (M_PRT699), SEQ ID NO:31 (M_PRT698), or SEQ ID NO:32 (Met-PRT966), or (6-ii) a modified fibroin including an amino acid sequence having a sequence identity of 90% or higher with an amino acid sequence set forth in SEQ ID NO:25, SEQ ID NO:26, SEQ ID NO:27, SEQ ID NO:28, SEQ ID NO:29, SEQ ID NO:30, SEQ ID NO:31, or SEQ ID NO:32, may be mentioned.

The modified fibroin of (6-i) will be described. The amino acid sequence set forth in SEQ ID NO:25 is an amino acid sequence obtained by substituting all of QQ's in the amino acid sequence set forth in SEQ ID NO:7 (Met-PRT410) with VL's. The amino acid sequence set forth in SEQ ID NO:26 is an amino acid sequence obtained by substituting all of QQ's in the amino acid sequence set forth in SEQ ID NO:7 with TS's, and substituting the remaining Q's with A's. The amino acid sequence set forth in SEQ ID NO:27 is an amino acid sequence obtained by substituting all of QQ's in the amino acid sequence set forth in SEQ ID NO:7 with VL's, and substituting the remaining Q's with I's. The amino acid sequence set forth in SEQ ID NO:28 is an amino acid sequence obtained by substituting all of QQ's in the amino acid sequence set forth in SEQ ID NO:7 with VI's, and substituting the remaining Q's with L's. The amino acid sequence set forth in SEQ ID NO:29 is an amino acid sequence obtained by substituting all of QQ's in the amino acid sequence set forth in SEQ ID NO:7 with VF, and substituting the remaining Q's with I's.

The amino acid sequence set forth in SEQ ID NO:30 is an amino acid sequence obtained by substituting all of QQ's in the amino acid sequence set forth in SEQ ID NO:8 (Met-PRT468) with VL's. The amino acid sequence set forth in SEQ ID NO:31 is an amino acid sequence obtained by substituting all of QQ's in the amino acid sequence set forth in SEQ ID NO:8 with VL's, and substituting the remaining Q's with I's.

The amino acid sequence set forth in SEQ ID NO:32 is an amino acid sequence obtained by substituting all of QQ's in a sequence in which a region of twenty domain sequences present in the amino acid sequence set forth in SEQ ID NO:7 (Met-PRT410) is repeated twice, with VF's, and substituting the remaining Q's with I's.

In the amino acid sequences set forth in SEQ ID NO:25, SEQ ID NO:26, SEQ ID NO:27, SEQ ID NO:28, SEQ ID NO:29, SEQ ID NO:30, SEQ ID NO:31, and SEQ ID NO:32, the glutamine residue percentage content is 9% or less in all cases (Table 2).

TABLE 2

| Modified fibroin | Glutamine residue percentage content | GPGXX motif percentage content | Degree of hydrophobicity of REP |
|---|---|---|---|
| Met-PRT410 (SEQ ID NO: 7) | 17.7% | 27.9% | −1.52 |
| M_PRT888 (SEQ ID NO: 25) | 6.3% | 27.9% | −0.07 |
| M_PRT965 (SEQ ID NO: 26) | 0.0% | 27.9% | −0.65 |
| M_PRT889 (SEQ ID NO: 27) | 0.0% | 27.9% | 0.35 |
| M_PRT916 (SEQ ID NO: 28) | 0.0% | 27.9% | 0.47 |
| M_PRT918 (SEQ ID NO: 29) | 0.0% | 27.9% | 0.45 |
| M_PRT699 (SEQ ID NO: 30) | 3.6% | 26.4% | −0.78 |
| M_PRT698 (SEQ ID NO: 31) | 0.0% | 26.4% | −0.03 |
| Met-PRT966 (SEQ ID NO: 32) | 0.0% | 28.0% | 0.35 |

The modified fibroin of (6-i) may comprise an amino acid sequence set forth in SEQ ID NO:25, SEQ ID NO:26, SEQ ID NO:27, SEQ ID NO:28, SEQ ID NO:29, SEQ ID NO:30, SEQ ID NO:31, or SEQ ID NO:32.

The modified fibroin of (6-ii) includes an amino acid sequence having a sequence identity of 90% or higher with an amino acid sequence set forth in SEQ ID NO:25, SEQ ID NO:26, SEQ ID NO:27, SEQ ID NO:28, SEQ ID NO:29, SEQ ID NO:30, SEQ ID NO:31, or SEQ ID NO:32. The modified fibroin (6-ii) is also a protein including a domain sequence represented by Formula 1: $[(A)_n \text{ motif-REP}]_m$ or Formula 2: $[(A)_n \text{ motif-REP}]_m\text{-}(A)_n$ motif. The sequence identity is preferably 95% or higher.

The modified fibroin of (6-ii) is such that the glutamine residue percentage content is preferably 9% or less. Furthermore, the modified fibroin of (6-ii) is such that the GPGXX motif percentage content is preferably 10% or more.

The modified fibroin of the sixth embodiment may include a tag sequence at either or both of the N-terminus and the C-terminus. Thereby, isolation, fixation, detection, visualization, and the like of the modified fibroin are made possible.

As a more specific example of a modified fibroin including a tag sequence, (6-iii) a modified fibroin including an amino acid sequence set forth in SEQ ID NO:33 (PRT888), SEQ ID NO:34 (PRT965), SEQ ID NO:35 (PRT889), SEQ ID NO:36 (PRT916), SEQ ID NO:37 (PRT918), SEQ ID NO:38 (PRT699), SEQ ID NO:39 (PRT698), or SEQ ID NO:40 (PRT966), or (6-iv) a modified fibroin including an amino acid sequence having a sequence identity of 90% or higher with an amino acid sequence set forth in SEQ ID NO:33, SEQ ID NO:34, SEQ ID NO:35, SEQ ID NO:36, SEQ ID NO:37, SEQ ID NO:38, SEQ ID NO:39, or SEQ ID NO:40, may be mentioned.

The amino acid sequences set forth in SEQ ID NO:33, SEQ ID NO:34, SEQ ID NO:35, SEQ ID NO:36, SEQ ID NO:37, SEQ ID NO:38, SEQ ID NO:39, and SEQ ID NO:40 are amino acid sequences obtained by adding the amino acid sequence set forth in SEQ ID NO:11 (including a His tag sequence and a hinge sequence) to the N-terminus of the amino acid sequences set forth in SEQ ID NO:25, SEQ ID NO:26, SEQ ID NO:27, SEQ ID NO:28, SEQ ID NO:29, SEQ ID NO:30, SEQ ID NO:31, and SEQ ID NO:32, respectively. Since this is merely addition of a tag sequence to the N-terminus, there is no change in the glutamine residue percentage content, and in the amino acid sequences set forth in SEQ ID NO:33, SEQ ID NO:34, SEQ ID NO:35, SEQ ID NO:36, SEQ ID NO:37, SEQ ID NO:38, SEQ ID NO:39, and SEQ ID NO:40, the glutamine residue percentage content is 9% or less in all cases (Table 3).

TABLE 3

| Modified fibroin | Glutamine residue percentage content | GPGXX motif percentage content | Degree of hydrophobicity of REP |
|---|---|---|---|
| PRT888 (SEQ ID NO: 33) | 6.3% | 27.9% | −0.07 |
| PRT965 (SEQ ID NO: 34) | 0.0% | 27.9% | −0.65 |
| PRT889 (SEQ ID NO: 35) | 0.0% | 27.9% | 0.35 |
| PRT916 (SEQ ID NO: 36) | 0.0% | 27.9% | 0.47 |
| PRT918 (SEQ ID NO: 37) | 0.0% | 27.9% | 0.45 |
| PRT699 (SEQ ID NO: 38) | 3.6% | 26.4% | −0.78 |
| PRT698 (SEQ ID NO: 39) | 0.0% | 26.4% | −0.03 |
| PRT966 (SEQ ID NO: 40) | 0.0% | 28.0% | 0.35 |

The modified fibroin of (6-iii) may also comprise an amino acid sequence set forth in SEQ ID NO:33, SEQ ID NO:34, SEQ ID NO:35, SEQ ID NO:36, SEQ ID NO:37, SEQ ID NO:38, SEQ ID NO:39, or SEQ ID NO:40.

The modified fibroin of (6-iv) includes an amino acid sequence having a sequence identity of 90% or higher with an amino acid sequence set forth in SEQ ID NO:33, SEQ ID NO:34, SEQ ID NO:35, SEQ ID NO:36, SEQ ID NO:37, SEQ ID NO:38, SEQ ID NO:39, or SEQ ID NO:40. The modified fibroin of (6-iv) is also a protein including a domain sequence represented by Formula 1: [(A)$_n$ motif-REP]$_m$, or Formula 2: [(A)$_n$ motif-REP]$_m$-(A)$_n$ motif. The sequence identity is preferably 95% or higher.

The modified fibroin of (6-iv) is such that the glutamine residue percentage content is preferably 9% or less. Furthermore, the modified fibroin of (6-iv) is such that the GPGXX motif percentage content is preferably 10% or more.

The modified fibroin of the sixth embodiment may include a secretory signal for releasing a protein produced in a recombinant protein production system to the outside of a host. The sequence of the secretory signal can be appropriately set according to the type of the host.

The modified fibroin may also be a modified fibroin which combines the features of at least two or more, among the features possessed by the modified fibroin of the first embodiment, the modified fibroin of the second embodiment, the modified fibroin of the third embodiment, the modified fibroin of the fourth embodiment, the modified fibroin of the fifth embodiment, and the modified fibroin of the sixth embodiment.

<Method for Producing Modified Fibroin>

The modified fibroin according to the present embodiment can be produced by, for example, using an expression vector that has a nucleic acid sequence encoding the modified fibroin and one or a plurality of regulatory sequences operably linked to the nucleic acid sequence, and expressing the nucleic acid by means of a host transformed with the expression vector.

The method for producing a nucleic acid encoding a modified fibroin is not particularly limited. For example, the nucleic acid can be produced by a method of utilizing a gene encoding naturally occurring fibroin, thereby amplifying and cloning the gene by a polymerase chain reaction (PCR) or the like, and modifying the nucleic acid by a genetic engineering technique, or a method of chemically synthesizing the nucleic acid method. The method of chemically synthesizing a nucleic acid is also not particularly limited, and for example, a gene can be chemically synthesized by a method of linking an oligonucleotide that has been automatically synthesized with AKTA oligopilot plus 10/100 (GE Healthcare Japan Corporation) or the like, by PCR or the like based on the amino acid sequence information of fibroin obtained from the NCBI web database and the like. At this time, in order to facilitate purification and/or confirmation of a modified fibroin, a nucleic acid encoding a modified fibroin comprising an amino acid sequence obtained by adding an amino acid sequence comprising a start codon and a His10 tag to the N-terminus of the above-described amino acid sequence, may be synthesized.

A regulatory sequence is a sequence that controls the expression of a modified fibroin in a host (for example, a promoter, an enhancer, a ribosome binding sequence, a transcription termination sequence, or the like), and can be appropriately selected according to the type of the host. As a promoter, an inducible promoter which functions in host cells and is capable of inducing expression of a modified fibroin may be used. An inducible promoter is a promoter that can control transcription by means of the presence of an inducer (expression inducer), the absence of a repressor molecule, or physical factors such as an increase or decrease in temperature, osmotic pressure, or the pH value.

The type of the expression vector can be appropriately selected according to the type of the host, from a plasmid vector, a virus vector, a cosmid vector, a fosmid vector, an artificial chromosome vector, and the like. As the expression vector, an expression vector which is capable of autonomous replication in a host cell or is capable of incorporation into the chromosome of a host, and contains a promoter at a position where a nucleic acid encoding a modified fibroin can be transcribed, is suitably used.

As the host, prokaryotes and eukaryotes such as yeast, filamentous fungi, insect cells, animal cells, and plant cells can all be suitably used.

Preferred examples of a prokaryote host include bacterial belonging to the genus *Escherichia*, the genus *Brevibacillus*, the genus *Serratia*, the genus *Bacillus*, the genus *Microbacterium*, the genus *Brevibacterium*, the genus *Corynebacterium*, the genus *Pseudomonas*, and the like. Examples of microorganisms belonging to the genus *Escherichia* include *Escherichia coli*, and the like. Examples of microorganisms belonging to the genus *Brevibacillus* include *Brevibacillus agri* and the like. Examples of microorganisms belonging to the genus *Serratia* include *Serratia liquefaciens* and the like. Examples of microorganisms belonging to the genus *Bacillus* include *Bacillus subtilis* and the like. Examples of microorganisms belonging to the genus *Microbacterium* include *Microbacterium ammoniaphilum* and the like. Examples of microorganisms belonging to the genus *Brevibacterium* include *Brevibacterium divaricatum* and the like. Examples of microorganisms belonging to the genus *Corynebacterium ammoniagenes* and the like. Examples of microorganisms belonging to the genus *Pseudomonas* include *Pseudomonas putida* and the like.

In a case in which a prokaryote is used as a host, examples of the vector into which a nucleic acid encoding a modified fibroin is introduced include pBTrp2 (manufactured by Boehringer Mannheim Corporation), pGEX (manufactured by Pharmacia), pUC18, pBluescriptII, pSupex, pET22b, pCold, pUB110, and pNCO2 (Japanese Unexamined Patent Publication No. 2002-238569), and the like.

Examples of a eukaryotic host include yeast and filamentous fungi (mold and the like). Examples of the yeast include yeasts belonging to the genus *Saccharomyces*, the genus *Pichia*, the genus *Schizosaccharomyces*, and the like. Examples of the filamentous fungi include filamentous fungi belonging to the genus *Aspergillus*, the genus *Penicillium*, the genus *Trichoderma*, and the like.

In a case in which a eukaryote is used as a host, examples of the vector into which a nucleic acid encoding a modified fibroin is introduced include YEP13 (ATCC37115), YEp24 (ATCC37051), and the like. Regarding a method for introducing an expression vector into the above-described host cells, any method can all be used as long as it is a method for introducing a DNA into the host cells. For example, a method of using calcium ions [Proc. Natl. Acad. Sci. USA, 69, 2110 (1972)], an electroporation method, a spheroplast method, a protoplast method, a lithium acetate method, a competent method, and the like may be mentioned.

Regarding a method for expressing a nucleic acid by a host transformed with an expression vector, secretory production, fusion protein expression, and the like can be carried out, in addition to direct expression, according to the method described in Molecular Cloning, $2^{nd}$ Edition, or the like.

A modified fibroin can be produced by, for example, culturing a host transformed with an expression vector in a culture medium, producing and accumulating the modified fibroin in the culture medium, and collecting the modified fibroin from the culture medium. The method of culturing a host in a culture medium can be carried out according to a method that is usually used for culturing a host.

In a case in which the host is a prokaryote such as *Escherichia coli* or a eukaryote such as yeast, as the culture medium, any of a natural medium and a synthetic medium may be used as long as it is a medium that contains a carbon source, a nitrogen source, inorganic salts, and the like that can be assimilated by the host and is capable of efficiently implementing culturing of the host.

The carbon source may be any carbon source that can be assimilated by the transformed microorganism, and for example, carbohydrates such as glucose, fructose, sucrose, and molasses, starch, and starch hydrolysates containing these; organic acids such as acetic acid and propionic acid; and alcohols such as ethanol and propanol, can be used. Examples of the nitrogen source include ammonia, ammonium salts of inorganic acids or organic acids, such as ammonium chloride, ammonium sulfate, ammonium acetate, and ammonium phosphate; other nitrogen-containing compounds; and peptone, meat extract, yeast extract, corn steep liquor, casein hydrolysate, soybean cake and soybean cake hydrolysate, various fermented microbial cells, and digestion products thereof. As the inorganic salts, for example, monopotassium phosphate, dipotassium phosphate, magnesium phosphate, magnesium sulfate, sodium chloride, ferrous sulfate, manganese sulfate, copper sulfate, and calcium carbonate can be used.

Culture of a prokaryote such as *Escherichia coli* or a eukaryote such as yeast can be carried out, for example, under aerobic conditions such as shaking culture or deep aeration stirring culture. The culture temperature is, for example, 15° C. to 40° C. The culture time is usually 16 hours to 7 days. It is preferable that the pH of the culture medium during culture is maintained at 3.0 to 9.0. Adjustment of the pH of the culture medium can be carried out using an inorganic acid, an organic acid, an alkali solution, urea, calcium carbonate, ammonia, and the like.

Furthermore, during culture, antibiotic substances such as ampicillin and tetracycline may also be added to the culture medium, as necessary. In the case of culturing a microorganism transformed with an expression vector that uses an inducible promoter as a promoter, if necessary, an inducer may be added to the medium. For example, in the case of culturing a microorganism transformed with an expression vector that uses a lac promoter, isopropyl-β-D-thiogalactopyranoside or the like may be added to the medium, and in the case of culturing a microorganism transformed with an expression vector that uses a trp promoter, indole acrylic acid or the like may be added to the medium.

Isolation and purification of the expressed modified fibroin can be carried out by a method that is usually used. For example, in a case in which the modified fibroin is expressed in a state of being dissolved in cells, after completion of culture, the host cells are collected by centrifugal separation and suspended in a water-based buffer solution, subsequently the host cells are disrupted using an ultrasonic disruptor, a French press, a Manton-Gaulin homogenizer, a Dyno Mill, or the like, and a cell-free extract is obtained. From a supernatant obtained by centrifugally separating this cell-free extract, a purified preparation can be obtained by a method that is conventionally used for the isolation and purification of a modified fibroin, that is, methods such as a solvent extraction method, a salting-out method using ammonium sulfate or the like, a desalting method, a precipitation method using an organic solvent, an anion exchange chromatography method using a resin such as diethylaminoethyl (DEAE)-sepharose or DIAION HPA-75 (manufactured by Mitsubishi Kasei Corporation), a cation exchange chromatography method using a resin such as S-Sepharose FF (manufactured by Pharmacia), a hydrophobic chromatography method using a resin such as butyl sepharose or phenyl sepharose, a gel filtration method using a molecular sieve, an affinity chromatography method, a chromatofocusing method, and an electrophoresis method such as isoelectric point electrophoresis, singly or in combination.

Furthermore, in a case in which a modified fibroin has formed an insoluble matter in the cell and is expressed, host cells are similarly collected and then disrupted, centrifugal separation is carried out, and thereby the insoluble matter of the modified fibroin is collected as a precipitated fraction. The insoluble matter of the modified fibroin thus collected can be solubilized with a protein denaturing agent. After this operation, a purified preparation of the modified fibroin can be obtained by a similar isolation and purification method as described above. In a case in which the modified fibroin is secreted extracellularly, the modified fibroin can be collected from the culture supernatant. That is, the culture supernatant is obtained by treating a culture product by a technique such as centrifugal separation, and from the culture supernatant, a purified preparation can be obtained by using a similar isolation and purification method as described above.

<Water Resistance-Imparting Material>

A water resistance-imparting material is a material that can enhance water resistance of a molded article including a modified fibroin. As the molded article includes a water resistance-imparting material, for example, effects such as that water repellency of the molded article is enhanced and that contraction of the molded article at the time of contact with water is suppressed, are exhibited.

The water resistance-imparting material may be, for example, a hydrophobic polymer selected from a fluorine-based polymer, a silicone-based polymer, and a modified hydroxyl group-containing polymer formed as a result of a hydrophobic functional group being bonded to a hydroxyl group-containing polymer. The hydrophobicity-imparting material may be a protein binding agent selected from a polyfunctional reaction agent (first reaction agent) having two or more first reactive groups capable of reacting with a protein and forming a bond, and a reaction agent having one or more first reactive groups capable of reacting with a protein and forming a bond.

The fluorine-based polymer is not particularly limited as long as it is a polymer including fluorine. The fluorine-based polymer may be, for example, a polymer obtainable by polymerizing an olefin including fluorine. Examples of the fluorine-based polymer include polytetrafluoroethylene, polytrifluoroethylene, polychlorotrifluoroethylene, polyvinyl fluoride, polyvinylidene fluoride, polyperfluoroalkyl vinyl ether, polyperfluoropropylene, a polytetrafluoroethylene-perfluoropropylene copolymer, a tetrafluoroethylene-ethylene copolymer, and a polyvinyl fluoride-ethylene copolymer. The fluorine-based polymer may also be a copolymer (including a random copolymer, a block copolymer, or an alternating copolymer) obtainable by polymerizing two or more kinds of monomers that constitute the polymers mentioned as examples.

The silicone-based polymer is not particularly limited as long as it is a polymer having a polysiloxane structure as the main chain. The silicone-based polymer may be, for example, a homopolymer or a copolymer (including a random copolymer, a block copolymer, or an alternating copolymer) obtainable by polymerizing one kind or two or more kinds of monomers having a siloxane structural unit. The silicone-based polymer may also be a copolymer obtainable by polymerizing one kind or two or more kinds of monomers having a siloxane structural unit and one kind or two or more kinds of monomers that do not have a siloxane structural unit.

The modified hydroxyl group-containing polymer is a polymer in which a hydrophobic functional group is bonded to a hydroxyl group-containing polymer. The modified hydroxyl group-containing polymer can be obtained by, for example, reacting a hydroxyl group-containing polymer with a reaction agent having a hydrophobic functional group.

The hydroxyl group-containing polymer can be used without any particular limitation as long as it is a polymer compound having a hydroxyl group. Specific examples of the hydroxyl group-containing polymer include, for example, polysaccharides such as starch, glycogen, cellulose, chitin, agarose, hyaluronic acid, chondroitin sulfate, pectin, and carrageenan; and synthetic polymers such as polyvinyl alcohol (PVA) and a phenolic resin. As the hydroxyl group-containing polymer, from the viewpoint of having biodegradability, a polysaccharide is preferred. As the hydroxyl group-containing polymer, from the viewpoint of having high solubility in addition to having biodegradability, starch is preferred.

The reaction agent having a hydrophobic functional group is a compound having a hydrophobic functional group and further having a bondable functional group that can be bonded to a hydroxyl group-containing polymer. It is desirable that the bondable functional group is capable of bonding to the hydroxyl group-containing polymer by hydrogen bonding or covalent bonding; however, the bondable functional group is preferably a functional group capable of bonding to the hydroxyl group-containing polymer by covalent bonding, and more preferably a functional group capable of bonding to the hydroxyl group-containing polymer by covalent bonding by a reaction with a hydroxyl group in the hydroxyl group-containing polymer. Examples of the hydrophobic functional group include alkyl groups such as a methyl group, an ethyl group, an n-propyl group, and an isopropyl group; aromatic groups such as a phenyl group and a naphthyl group; and acyl groups such as an acetyl group, a propanoyl group, and a benzoyl group. Examples of the reaction agent having a hydrophobic functional group include an isocyanate having a hydrophobic functional group (R—N=C=O; R represents a hydrophobic functional group), an acid anhydride (R—C(=O)—O—C(=O)—R; R represents a hydrophobic functional group), an epoxide, an aziridine, an alkyl halide, and the like.

Examples of the protein binding agent include a polyfunctional reaction agent (first reaction agent) having two or more of a first reactive group capable of reacting with a protein and forming a bond, and a reaction agent (functional reaction agent) having one or more first reactive groups capable of reacting with a protein and forming a bond, and a functional group.

The first reaction agent has a first reactive group capable of reacting with at least one reactive functional group selected from the group consisting of an amide group, a hydroxyl group, a phenolic hydroxy group, an amino group, a carboxyl group, a thiol group, a selenol group, an imidazolyl group, an indolyl group, and a guanidino group, all of which are included in proteins, and forming a bond.

As the first reactive group, for example, a group represented by the following Formula (A-1), (A-2), (A-3), (A-4), (A-5), or a (A-6) may be mentioned. Wavy lines in the respective formulae each represent a linking bond of each group.

(A-1)

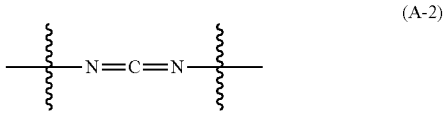
(A-2)

(A-3)

(A-4)

(A-5)

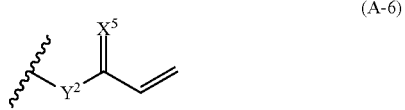
(A-6)

In Formula (A-1), $X^1$ represents an oxygen atom (O) or a sulfur atom (S). In Formula (A-3), $X^2$ represents a leaving group. In Formula (A-4), $X^3$ represents an oxygen atom (O), a sulfur atom (S), a group represented by —$NR^4$—, or a group represented by —$C(R^5)_2$—. $R^4$ may be, for example, a hydrogen atom, an alkyl group, an aryl group, a halogenated alkyl group, a halogenated aryl group, an arylsulfonyl group, an alkylsulfonyl group, an acyl group, or a carbamate group. $R^5$ represents an electron-withdrawing group. In Formula (A-5), $X^4$ represents an oxygen atom (O) or a sulfur atom (S); and $Y^1$ represents a halogen atom, a hydroxyl group, a group represented by —$R^6$, a group represented by —$OR^6$, or a group represented by —$OCOR^6$. $R^6$ may be, for example, an alkyl group, an aryl group, a halogenated alkyl group, or a halogenated aryl group. In Formula (A-6), $X^5$ represents an oxygen atom (O) or a sulfur atom (S); and $Y^2$ represents an oxygen atom (O), a sulfur atom (S), or a group represented by $NR^7$. $R^7$ may be, for example, an alkylsulfonyl group, an arylsulfonyl group, an acyl group, a carbamate group, an alkyl group, an aryl group, a halogenated alkyl group, or a halogenated aryl group.

The functional reaction agent can be obtained by reacting a first reaction agent with a reaction agent (second reaction agent) that has a second reactive group (one group) capable of reacting with the first reactive group and forming a bond, and a functional group.

Examples of the second reactive group include a hydroxyl group, a thiol group, an amino group, a group represented by the following Formula (B-1), and the like.

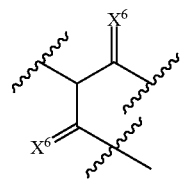

(B-1)

In Formula (B-1), $X^6$ represents an oxygen atom (O) or a sulfur atom (S).

Examples of the functional group include a hydrocarbon group such as an alkyl group, an alkenyl group, or an alkynyl group; a group having a cyclic structure, such as an aryl group or a heterocyclic group; a reactive group (a hydroxy group, an amino group, a thiol group, or the like) protected with a protective group; a group having a structure such as a carbonyl group (—C(=O)—), an ether bond (—O—), an amide bond (>NC(=O)—), a urethane bond (>NC(=O)O—), a urea bond (>N(C=O)N<), or a carbonate bond (—OC(=O)O—); an alkoxysilyl group, a sulfonyl group (—S(=O)—), a carboxyl group (—C(=O)OH—), a sulfonic acid group (—S(=O)$_2$OH), a quaternary ammonium group, and the like.

A specific example of the first reaction agent may be hexane diisocyanate (HDI). A specific example of the second reaction agent may be butanol (BuOH).

Regarding the water resistance-imparting material, from the viewpoint that water repellency of the molded article is enhanced, and that contraction at the time of contact with water can also be suppressed, a fluorine-based polymer and a silicone-based polymer are preferred.

From the viewpoint of having superior texture, tactile sensation, and the like of the molded article, it is preferable that the water resistance-imparting material is not a crosslinking agent for a low molecular weight compound (for example, a molecular weight of 500 or less). It is because when intermolecular crosslinking of the modified fibroin is formed by a crosslinking agent for a low molecular weight compound, enhancement of water resistance, strength, and the like can be promoted, and the texture, tactile sensation, and the like of the molded article may not be sufficient.

<Molded Article and Method for Producing the Same>

The molded article according to the present embodiment includes at least a modified fibroin and a water resistance-imparting material. The molded article according to the present embodiment may be such that the modified fibroin and the water resistance-imparting material are covalently bonded.

The molded article according to the present embodiment may further include other additives according to the shape, use application, and the like of the molded article. Examples of the additives include a plasticizer, a leveling agent, a crosslinking agent, a crystal nucleating agent, an oxidation inhibitor, an ultraviolet absorber, a colorant, a filler, and a synthetic resin. The content of the additives may be 50 parts by mass or less with respect to 100 parts by mass of the total amount of the modified fibroin.

Figure 6:
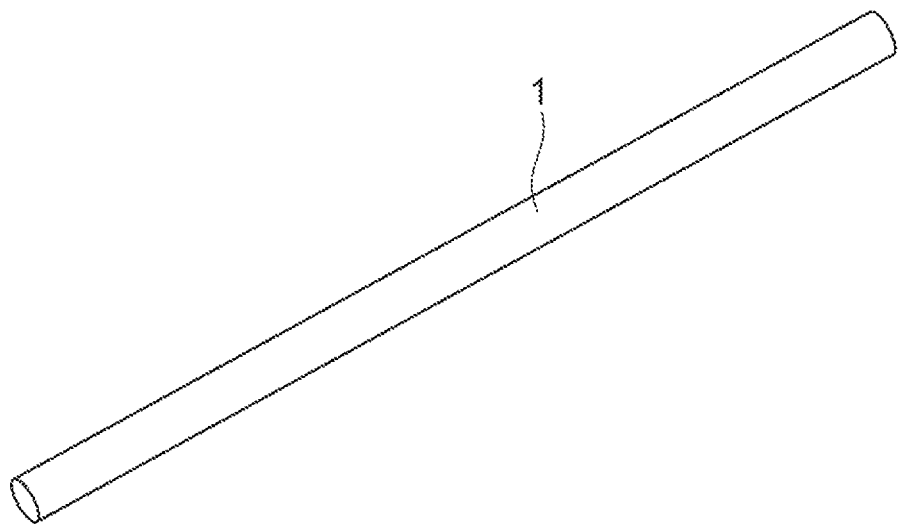
FIG. 6 is a perspective view illustrating an embodiment of a fiber as an example of a molded article.

The shape of the molded article according to the present embodiment is not particularly limited and may be, for example, a fiber, a film, a porous body, a mold-molded article, or the like. The molded article according to the present embodiment may also be twisted yarn obtained by twisting, weaving, or knitting the above-described fiber, a woven fabric (including woven cloth), a knitted fabric (including knitted cloth), a braided fabric, a nonwoven fabric, or the like. Furthermore, the fiber can be applied to rope, surgical suture, a flexible fastener for electrical components, and high-strength usage applications such as a physiologically active material for transplantation (for example, an artificial ligament and an aortic band). FIG. 6 is a perspective view illustrating an embodiment of a fiber 1 as an example of the molded article.

The molded article according to the present embodiment can be produced by, for example, a production method (first production method) including: a step (precursor molded article forming step) of molding a raw material (for example, a dope solution) including the modified fibroin and optionally other additives and obtaining a precursor molded article; and a step (bonding step) of bonding a water resistance-imparting material to the precursor molded article including the modified fibroin thus formed. The molded article according to the present embodiment can also be produced by, for example, a production method (second production method) including a step (molded article forming step) of molding a raw material (for example, a dope solution) including a modified fibroin, a water resistance-imparting material, and optionally other additives, and obtaining a molded article.

In the precursor molded article forming step and the molded article forming step, a precursor molded article or a molded article having a desired shape is formed by molding a raw material (for example, a dope solution).

The dope solution includes at least a modified fibroin and optionally, a water resistance-imparting material, other additives, and a solvent. The dope solution may further include a dissolution accelerator.

Examples of the solvent include hexafluoroisopropanol (HFIP), hexafluoroacetone (HFA), dimethyl sulfoxide (DMSO), N,N-dimethylformamide (DMF), formic acid, urea; aqueous solutions including guanidine, sodium dodecyl sulfate (SDS), lithium bromide, calcium chloride, lithium thiocyanate, and the like; and the like. These solvents may be used singly, or two or more kinds thereof may be used as mixtures.

The content of the modified fibroin in the dope solution may be 15% by mass or more, 30% by mass or more, 40% by mass or more, or 50% by mass or more, based on the total mass of the dope solution. The content of the modified fibroin may be 70% by mass or less, 65% by mass or less, or 60% by mass or less, based on the total mass of the dope solution, from the viewpoint of the production efficiency for the dope solution.

In a case in which the dope solution includes a water resistance-imparting material, the content of the water resistance-imparting material may be 3% by mass or more, 6% by mass or more, 8% by mass or more, or 10% by mass or more, based on the total mass of the dope solution. The content of the water resistance-imparting material may be 14% by mass or less, 13% by mass or less, or 12% by mass or less, based on the total mass of the dope solution, from the viewpoint of the production efficiency for the dope solution.

As the dissolution accelerator, for example, an inorganic salt comprising a Lewis acid and a Lewis base described below, may be mentioned. Examples of the Lewis base include oxo acid ions (nitrate ions, perchlorate ions, and the like), metal oxo acid ions (permanganate ions and the like), halide ions, thiocyanate ions, cyanate ions, and the like. Examples of the Lewis acid include metal ions such as alkali metal ions and alkaline earth metal ions; polyatomic ions such as ammonium ion; complex ions; and the like. Specific examples of an inorganic salt comprising a Lewis acid and a Lewis base include lithium salts such as lithium chloride, lithium bromide, lithium iodide, lithium nitrate, lithium perchlorate, and lithium thiocyanate; calcium salts such as calcium chloride, calcium bromide, calcium iodide, calcium nitrate, calcium perchlorate, and calcium thiocyanate; iron salts such as iron chloride, iron bromide, iron iodide, iron nitrate, iron perchlorate, and iron thiocyanate; aluminum salts such as aluminum chloride, aluminum bromide, aluminum iodide, aluminum nitrate, aluminum perchlorate, and aluminum thiocyanate; potassium salts such as potassium chloride, potassium bromide, potassium iodide, potassium nitrate, potassium perchlorate, and potassium thiocyanate; sodium salts such as sodium chloride, sodium bromide, sodium iodide, sodium nitrate, sodium perchlorate, and sodium thiocyanate; zinc salts such as zinc chloride, zinc bromide, zinc iodide, zinc nitrate, zinc perchlorate, and zinc thiocyanate; magnesium salts such as magnesium chloride, magnesium bromide, magnesium iodide, magnesium nitrate, magnesium perchlorate, and magnesium thiocyanate; barium salts such as barium chloride, barium bromide, barium iodide, barium nitrate, barium perchlorate, and barium thiocyanate; and strontium salts such as strontium chloride, strontium bromide, strontium iodide, strontium nitrate, strontium perchlorate, and strontium thiocyanate.

The content of the dissolution accelerator may be 1.0 part by mass or more, 5.0 parts by mass or more, 9.0 parts by mass or more, 15 parts by mass or more, or 20.0 parts by mass or more, with respect to 100 parts by mass of the total amount of proteins. The content of the dissolution accelerator may be 40 parts by mass or less, 35 parts by mass or less, or 30 parts by mass or less, with respect to 100 parts by mass of the total amount of proteins.

At the time of production of the dope solution, the dope solution may be warmed to 30° C. to 90° C. The dissolvable temperature may be set at a suitable time according to the types of the solvent, modified fibroin, and water resistance-imparting material used, and the like. In order to accelerate dissolution, shaking and stirring may be carried out.

The viscosity of the dope solution may be appropriately set. For example, in a case in which the dope solution is used as a spinning solution, the viscosity may be appropriately set according to the spinning method, and for example, the viscosity may be set to 100 to 15,000 cP (centipoises) at 35° C., and to 100 to 30,000 cP (centipoises) at 40° C., or the like. The viscosity of the spinning solution can be measured using, for example, trade name "EMS VISCOMETER" manufactured by Kyoto Electronics Manufacturing Co., Ltd.

A film-shaped precursor molded article and a molded article (film) are obtained by, for example, a method of forming a film of the above-mentioned dope solution and removing the solvent from the film thus formed.

A fibrous precursor molded article and a molded article (protein fiber) are obtained by, for example, a method of spinning the above-mentioned dope solution and removing the solvent from the spun dope solution.

Regarding a porous precursor molded article and a molded article (protein porous body), a method for producing a porous body from a fibroin-derived protein is described in WO 2014/175178, and basically, the porous precursor molded article and the molded article are obtained by this method.

Regarding a precursor molded article and a molded article, for example, a method for producing a mold-molded article from a fibroin-derived protein is described in International Publication WO 2017/047504, and basically, the precursor molded article and the molded article are obtained by this method. Incidentally, at the time of producing a precursor molded article or a molded article from a modified fibroin, for example, the following operation is carried out.

That is, first, a raw material composition including a modified fibroin and optionally a water resistance-imparting material and other additives is introduced into a mold of a pressure molding machine, and then the mold is heated while simultaneously pressure is applied to the raw material composition. Under predetermined pressure, heating and pressurization are continued until the raw material composition reaches a predetermined temperature, and thereby a heated and pressurized raw material composition is obtained. Next, the temperature of the mold is lowered using a cooling machine (for example, a spot cooler), and when the raw material composition has reached a predetermined temperature, the content is taken out. Thus, a precursor molded article or a molded article is obtained. Heating is carried out preferably at 80° C. to 300° C., more preferably 100° C. to 180° C., and even more preferably 100° C. to 130° C. Pressurization is carried out preferably at 5 kN or higher, more preferably 10 kN or higher, and even more preferably 20 kN or higher. Furthermore, after predetermined heating and pressurization conditions are reached, the time for continuing the treatment under those conditions (thermal insulation conditions) is preferably 0 to 100 minutes, more preferably 1 to 50 minutes, and even more preferably 5 to 30 minutes.

The bonding step is a step of bonding a water resistance-imparting material to the precursor molded article including a modified fibroin. The bonding step can be carried out by, for example, bringing a water resistance-imparting material to the precursor molded article by means of application, immersion, or the like, performing heating, plasma irradiation, or the like as necessary, and bonding the precursor molded article to the water resistance-imparting material. In a case in which the water resistance-imparting material is, for example, a hydrophobic polymer such as a silicon-based polymer and a fluorine-based polymer, the bonding step may be a step of irradiating the precursor molded article with plasma in a state in which the water resistance-imparting material or a precursor (monomer) of the water resistance-imparting material is brought into contact with the precursor molded article, and thereby covalently bonding the modified fibroin and the water resistance-imparting material. Even in the case of using a precursor (monomer) of the water resistance imparting material, since the precursor (monomer) of the water resistance-imparting material is polymerized by irradiation of plasma, and thereby a water resistance-imparting material (hydrophobic polymer such as a silicon-based polymer and a fluorine-based polymer) is formed, a molded article including a modified fibroin and a water resistance-imparting material can be obtained.

The plasma to be irradiated may be appropriately set according to the types of the modified fibroin and the water resistance-imparting material (or a precursor thereof), the shape of the precursor molded article, or the like. The flow rate of the discharge gas may be, for example, in the range of 0.1 l/min or more and 10 l/min or less. The plasma density of the plasma to be generated may be, for example, in the range of $1 \times 10^{13}$ cm$^{-3}$ or more and $1 \times 10^{15}$ cm$^{-3}$ or less. The discharge gas may be, for example, a noble gas such as helium, neon, or argon; oxygen, nitrogen, or the like. Air can also be used as the discharge gas.

Plasma irradiation can be carried out using a known plasma irradiation apparatus. Regarding the plasma irradiation apparatus, for example, a plasma treatment apparatus manufactured by Europlasma, SA can be used.

The molded article according to the present embodiment may be, for example, a manufactured product selected from the group consisting of a fiber, a yarn, a filament, a film, a foam, a sphere, a nanofibril, a hydrogel, a resin, and equivalents thereof. These can be produced according to the methods described in Japanese Unexamined Patent Publication No. 2009-505668, Japanese Patent No. 5678283, Japanese Patent No. 4638735, and the like.

EXAMPLES

Hereinafter, the present invention will be described more specifically based on Examples. However, the present invention is not intended to be limited to the following Examples.

Production of Modified Fibroin (1) Establishment of Expression Vector

A modified fibroin (PRT799) having an amino acid sequence set forth in SEQ ID NO:15 and a modified fibroin (PRT918) having an amino acid sequence set forth in SEQ ID NO:37 were designed.

Nucleic acids encoding proteins having the designed amino acid sequences were respectively synthesized. To the nucleic acids, NdeI site was added to the 5'-terminus, and EcoRI site was added to the downstream of the stop codon. These two kinds of nucleic acids were respectively cloned into a cloning vector (pUC118). Thereafter, the same nucleic acids were cleaved at NdeI and EcoRI by treating with restriction enzymes and then were respectively recombined into a protein expression vector pET-22b(+), and thereby expression vectors were obtained.

(2) Expression of Modified Fibroin

*Escherichia coli* BLR(DE3) was transformed with each of the expression vectors thus obtained. These transformed *Escherichia coli* cells were cultured for 15 hours in 2 mL of LB medium including ampicillin. The culture liquid was added to 100 mL of a medium for seed culture (Table 4) including ampicillin such that the $OD_{600}$ would be 0.005. The culture liquid temperature was maintained at 30° C., flask culture for about 15 hours was carried out until the $OD_{600}$ reached 5, and a seed culture liquid was obtained.

TABLE 4

| Medium for seed culture (per 1 L at the time of initiation of culture) | |
|---|---|
| Glucose | 5 g |
| $KH_2PO_4$ | 4 g |
| $K_2HPO_4$ | 10 g |
| Yeast Extract | 6 g |

A medium for seed culture was obtained by adding ampicillin such that the final concentration would be 100 mg/L.

This seed culture liquid was added to a jar fermenter, to which 500 mL of a production medium (Table 5) had been added, such that the $OD_{600}$ would be 0.05, and transformed *Escherichia coli* was inoculated therein. Culture was carried out by maintaining the culture liquid temperature at 37° C. and controlling the pH to be constant at 6.9. The dissolved oxygen concentration in the culture liquid was maintained at 20% of the dissolved oxygen saturation concentration.

TABLE 5

| Production medium (per 1 L at the time of initiation of culture) | |
|---|---|
| Glucose | 12 g |
| $KH_2PO_4$ | 9 g |
| $MgSO_4 \cdot 7H_2O$ | 2.4 g |
| Yeast Extract | 15 g |
| $FeSO_4 \cdot 7H_2O$ | 40 mg |
| $MnSO_4 \cdot 5H_2O$ | 40 mg |

TABLE 5-continued

| Production medium (per 1 L at the time of initiation of culture) | |
|---|---|
| $CaCl_2 \cdot 2H_2O$ | 40 mg |
| GD-113 (defoaming agent) | 0.1 mL |

Immediately after the glucose in the production medium had been completely consumed, a feed liquid (glucose 455 g/1 L and Yeast Extract 120 g/1 L) was added thereto at a rate of 1 mL/min. Culture was carried out by maintaining the culture liquid temperature at 37° C. and controlling the pH to be constant at 6.9. While the dissolved oxygen concentration in the culture liquid was maintained at 20% of the dissolved oxygen saturation concentration, culture was carried out for 20 hours. Subsequently, 1 M isopropyl-pi-thiogalactopyranoside (IPTG) was added to the culture liquid such that the final concentration would be 1 mM, and a target modified fibroin was subjected to induced expression. At the time point where 20 hours had elapsed after the addition of IPTG, the culture liquid was subjected to centrifugal separation, and bacterial cells were collected. SDS-PAGE was performed using the bacterial cells prepared from the culture liquids before the addition of IPTG and after the addition of IPTG, and the expression of the target modified fibroin was confirmed by the appearance of a band of a size of the target modified fibroin depending on the addition of IPTG.

(3) Purification of Modified Fibroin

Bacterial cells collected 2 hours after the addition of IPTG were washed with 20 mM Tris-HCl buffer (pH 7.4). The bacterial cells after the washing were suspended in a 20 mM Tris-HCl buffer solution (pH 7.4) including about 1 mM PMSF, and the cells were disrupted with a high-pressure homogenizer (GEA Niro Soavi S.p.A.). The disrupted cells were subjected to centrifugal separation, and a precipitate was obtained. The precipitate thus obtained was washed with a 20 mM Tris-HCl buffer solution (pH 7.4) until high purity was obtained. The precipitate after washing was suspended in an 8 M guanidine buffer solution (8 M guanidine hydrochloride, 10 mM sodium dihydrogen phosphate, 20 mM NaCl, and 1 mM Tris-HCl, pH 7.0) so as to obtain a concentration of 100 mg/mL. The suspension was stirred with a stirrer for 30 minutes at 60° C., and the precipitate was dissolved in the buffer solution. After dissolution, dialysis was carried out with water using a dialysis tube (cellulose tube 36/32 manufactured by Sanko Junyaku Co., Ltd.). A white aggregated protein obtained after dialysis was collected by centrifugal separation, moisture was removed therefrom with a freeze-dryer, and a freeze-dried powder was collected.

Test Example 1: Production and Evaluation of Woven Cloth (Molded Article)

(1) Preparation of Spinning Solution (Dope Solution)

DMSO in which lithium chloride was dissolved at a concentration of 4% by mass was used as a solvent. The freeze-dried powder of the modified fibroin (PRT799) produced as described above was added to the solvent such that the concentration would be 24% by mass. The modified fibroin was dissolved in the solvent by heating the system for 1 hour with an aluminum block heater at 90° C. Insoluble matters and foam were removed from the solution, and a spinning solution (dope solution) was obtained.

(2) Spinning

The spinning solution was charged into a reserve tank. The spinning solution was discharged into a 100 mass % methanol coagulation bath using a gear pump through a monohole nozzle having a diameter of 0.1 or 0.2 mm. The amount of discharge was adjusted to 0.01 to 0.08 mL/min. A fiber formed by coagulation of the spinning solution was washed and stretched in a 100 mass % methanol washing bath. After washing and stretching, the fiber was dried using a dry hot plate, and the raw yarn (modified fibroin fiber) thus obtained was wound.

(3) Production of Woven Cloth

A plied yarn was produced from the modified fibroin fiber thus obtained. The plied yarn thus produced was subjected to plain weaving, and a woven cloth was obtained.

(4) Bonding of Water Resistance-Imparting Material to Woven Cloth

A monomer for fluorine-based coating was applied on the woven cloth thus obtained. The woven cloth on which the monomer was applied was subjected to a plasma treatment using a plasma treatment apparatus (manufactured by Europlasma, SA). As a result of the plasma treatment, a woven cloth to which a fluorine-based polymer (water resistance-imparting material) formed by polymerization of the monomer for fluorine-based coating was covalently bonded, was obtained. As the monomer for fluorine-based coating, Nanofics110 (Example 1) and Nanofics120 (Example 2) (all manufactured by Europlasma, SA) were used.

(5) Evaluation of Water Repellency

The water repellency of the woven cloths of Example 1 and Example 2 that had been subjected to a plasma treatment, and of a woven cloth that had not been subjected to a plasma treatment (Comparative Example 1) was evaluated by a test for the degree of water repellency (spray test). The test for the degree of water repellency (spray test) was carried out according to ISO 4920:2012. Water repellency was determined by visual inspection according to 6-grade (scores 0 to 5) evaluation criteria shown below.

Score 5: Wetting of the surface and attachment of water droplets are not observed.

Score 4: Wetting of the surface does not occur, but attachment of water droplets is observed.

Score 3: Slight wetting is observed on the surface.

Score 2: Wetting has spread, and some wetted parts are connected to one another.

Score 1: Complete wetting is observed in the parts where water comes into contact.

Score 0: Wetting is observed over the entire surface.

The results are presented in Table 6. While the woven cloth of Comparative Example 1 that had not been subjected to a plasma treatment acquired score 0, the woven cloths of Example 1 and Example 2, which had been subjected to a plasma treatment, all acquired score 4 and were given with water resistance (water repellency).

TABLE 6

|  | Score |
|---|---|
| Comparative Example 1 | 0 |
| Example 1 | 4 |
| Example 2 | 4 |

(6) Evaluation of Tactile Sensation and Evaluation of Contractibility

From each of the woven cloths of Example 1, Example 2, and Comparative Example 1, a square-shaped test specimen that measured 5 cm on each side was cut out. On one surface of a test specimen, marking was made with a pencil at the positions of the four points corresponding to the vertices of a square that measured 30 mm on each side. A step of immersing each of the test specimens for 10 minutes in water at 40° C. and then vacuum drying the specimen at room temperature was repeated for 5 cycles. Vacuum drying was carried out using a vacuum constant-temperature dryer (VOS-310C, manufactured by Tokyo Rikakikai Co., Ltd.) for 30 minutes at a set pressure of −0.1 MPa. At the time of completion of each cycle, the tactile sensation was subjected to sensory evaluation, and also, the contraction ratio was determined by measuring the distances between the four marked points.

The tactile sensation was determined according to the following criteria. The results are presented in Table 7. In both of the woven cloths of Example 1 and Example 2, which had been subjected to a plasma treatment, deterioration of the tactile sensation was suppressed as compared to the woven cloth of Comparative Example 1 that had not been subjected to a plasma treatment.

Evaluation point 5: The tactile sensation is satisfactory similarly to the original one.

Evaluation point 4: The tactile sensation is satisfactory but is slightly poor compared to the original one.

Evaluation point 3: The tactile sensation is not poor but is slightly hard.

Evaluation point 2: The tactile sensation is poor and hard; however, the woven cloth is bendable.

Evaluation point 1: The tactile sensation is very poor, hard, and not bendable.

TABLE 7

| | Score | | | | | |
|---|---|---|---|---|---|---|
| | Original | After 1 cycle | After 2 cycles | After 3 cycles | After 4 cycles | After 5 cycles |
| Comparative Example 1 | 5 | 2 | 2 | 2 | 2 | 2 |
| Example 1 | 5 | 3 | 3 | 3 | 3 | 3 |
| Example 2 | 5 | 4 | 4 | 4 | 4 | 4 |

The contraction ratio was calculated by the following formula. The "average value of the lengths of the various sides" is a value obtained by dividing the total sum of the lengths of the various sides of a parallelepiped produced by the four marked points, by 4.

Contraction ratio (%)={1−(average value (mm) of lengths of various sides/30 mm)}×100

The results are presented in Table 8. The woven clothes of Example 1 and Example 2, which had been subjected to a plasma treatment, all had a smaller contraction ratio as compared to the woven cloth of Comparative Example 1 that had not been subjected to a plasma treatment.

TABLE 8

| | Contraction ratio (%) | | | | |
|---|---|---|---|---|---|
| | After 1 cycle | After 2 cycles | After 3 cycles | After 4 cycles | After 5 cycles |
| Comparative Example 1 | 25.0 | 24.5 | 25.3 | 25.6 | 25.6 |
| Example 1 | 3.8 | 5.4 | 10.5 | 17.4 | 17.8 |
| Example 2 | 9.4 | 9.5 | 9.9 | 14.7 | 15.0 |

Test Example 2: Production and Evaluation of Knitted Cloth (Molded Article)

(1) Preparation of Spinning Solution (Dope Solution)

DMSO in which lithium chloride was dissolved at a concentration of 4 mass % was used as a solvent. A freeze-dried powder of the modified fibroin (PRT918) produced as described above was added to the solvent so as to obtain a concentration of 24% by mass. The modified fibroin was dissolved in the solvent by heating the system for one hour with an aluminum block heater at 90° C. Insoluble matters and foam were removed from the solution, and a spinning solution (dope solution) was obtained.

(2) Spinning

The spinning solution was charged into a reserve tank. The spinning solution was discharged into a 100 mass % methanol coagulation bath using a gear pump through a monohole nozzle having a diameter of 0.1 or 0.2 mm. The amount of discharge was adjusted to 0.01 to 0.08 mL/min. A fiber formed by coagulation of the spinning solution was washed and stretched in a 100 mass % methanol washing bath. After washing and stretching, the fiber was dried using a dry hot plate, and the raw yarn (modified fibroin fiber) thus obtained was wound.

(3) Production of Knitted Cloth

The modified fibroin fiber thus obtained was cut, and modified fibroin stapes were produced. The modified fibroin stapes thus produced were subjected to fiber opening and wool opening, subsequently yarn spinning was performed using a known spinning apparatus, and a spun yarn was obtained. The spun yarn thus obtained was knitted using a whole garment flat knitting machine (MACH2XS, manufactured by SHIMA SEIKI MFG., LTD.), and a knitted cloth was obtained.

(4) Bonding of Water Resistance-Imparting Material to Knitted Cloth

A monomer for fluorine-based coating was applied on the knitted cloth thus obtained. The knitted cloth on which the monomer was applied was subjected to a plasma treatment using a plasma treatment apparatus (manufactured by Europlasma, SA). As a result of the plasma treatment, a knitted cloth to which a fluorine-based polymer (water resistance-imparting material) formed by polymerization of the monomer for fluorine-based coating was covalently bonded, was obtained (Example 3). As the monomer for fluorine-based coating, Nanofics120 (manufactured by Europlasma, SA) was used.

(5) Evaluation of Water Repellency

The water repellency of the knitted cloth of Example 3 that had been subjected to a plasma treatment, and of a knitted cloth that had not been subjected to a plasma treatment (Comparative Example 2) was evaluated by a test for the degree of water repellency (spray test) similar to Test Example 1. The results are presented in Table 9. While the knitted cloth of Comparative Example 2 that had not been subjected to a plasma treatment acquired score 0, the knitted cloth of Example 3 that had been subjected to a plasma treatment acquired score 5 and was given water resistance (water repellency).

TABLE 9

| | Score |
|---|---|
| Comparative Example 2 | 0 |
| Example 3 | 5 |

(6) Evaluation of Tactile Sensation and Evaluation of Contractibility

From each of the knitted cloths of Example 3 and Comparative Example 2, a square-shaped test specimen that measured 5 cm on each side was cut out. On one surface of a test specimen, marking was made with a pencil at the positions of the four points corresponding to the vertices of a square that measured 30 mm on each side. As a preliminary treatment, a step of immersing each of the test specimens for 10 minutes in water at 40° C. and then vacuum drying the specimen at room temperature was repeated for 5 cycles. Vacuum drying was carried out using a vacuum constant-temperature dryer (VOS-310C, manufactured by Tokyo Rikakikai Co., Ltd.) for 30 minutes at a set pressure of −0.1 MPa.

Next, for the test specimens that had been subjected to the preliminary treatment, a washing step, a drying step, a water immersion step, and a drying step were repeated for 5 cycles in this order. In the washing step, for the test specimen, washing was performed for 5 minutes using a washing machine manufactured by Panasonic Corporation (NA-VG1100L) and using a detergent manufactured by Lion Corporation (TOP CLEAR LIQUID), subsequently rinsing was performed two times, and then spin-drying was performed for 1 minute. In the drying step, drying of the test specimen was carried out at room temperature for 30 minutes at a set pressure of −0.1 MPa using a vacuum constant temperature dryer (VOS-310C, manufactured by Tokyo Rikakikai Co., Ltd.). In the water immersion step, the test specimen was immersed in water at 40° C. for 10 minutes. At the time of completion of each cycle, the tactile sensation was subjected to sensory evaluation according to criteria similar to those used in Test Example 1, and also, the contraction ratio was determined by measuring the distances between the four marked points.

The results for the sensory evaluation of the tactile sensation are presented in Table 10. The term "Upon initiation" indicates the evaluation results obtained before the cycles were initiated. In the knitted cloth of Example 3 that had been subjected to a plasma treatment, deterioration of the tactile sensation was suppressed as compared to the knitted cloth of Comparative Example 2 that had not been subjected to a plasma treatment.

TABLE 10

|  | Upon initiation | After 1 cycle | After 2 cycles | After 3 cycles | After 4 cycles | After 5 cycles |
| --- | --- | --- | --- | --- | --- | --- |
| Comparative Example 2 | 5 | 4 | 4 | 4 | 4 | 4 |
| Example 3 | 5 | 5 | 5 | 5 | 5 | 5 |

The results for the evaluation of the contraction ratio are presented in Table 11. In the knitted cloth of Example 3 that had been subjected to a plasma treatment, the contraction ratio was small as compared to the knitted cloth of Comparative Example 2 that had not been subjected to a plasma treatment.

TABLE 11

| | Contraction ratio (%) | | | | |
| --- | --- | --- | --- | --- | --- |
| | After 1 cycle | After 2 cycles | After 3 cycles | After 4 cycles | After 5 cycles |
| Comparative Example 2 | 19.5 | 22.0 | 24.3 | 25.3 | 27.1 |
| Example 3 | 10.7 | 15.0 | 17.0 | 17.0 | 18.9 |

Test Example 3: Production and Evaluation of Knitted Cloth (Molded Article)

(1) Preparation of Spinning Solution (Dope Solution)

DMSO in which lithium chloride was dissolved at a concentration of 4% by mass was used as a solvent. The freeze-dried powder of the modified fibroin (PRT799) produced as described above was added to the solvent such that the concentration would be 24% by mass. The modified fibroin was dissolved over 3 hours using a shaker, subsequently insoluble matters (contaminants and the like) and foam in the solution were removed, and a spinning solution (dope solution) was obtained. The solution viscosity of the dope solution was 5,000 cP (centipoises) at 90° C.

(2) Spinning

Dry-wet spinning was carried out using the dope solution thus obtained and a known dry-wet spinning apparatus, and a monofilament comprising the modified fibroin was obtained. Here, dry-wet spinning was carried out under the following conditions.

Temperature of coagulation liquid (methanol): 5° C. to 10° C.
Stretch ratio: 6 times
Drying temperature: 80° C.

(3) Production of Knitted Cloth

A spun fiber was produced by a known method using the modified fibroin fiber obtained as described above, flat knitting was carried out using this spun fiber comprising the modified fibroin fiber and a known knitting machine, and a knitted cloth that measured 5 cm on each side was obtained. The yarn count of the spun fiber comprising the modified fibroin fiber was 58.1 Nm, and the gauge number of the knitting machine was 18.

(4) Bonding of Water Resistance-Imparting Material to Knitted Cloth

A knitted cloth thus obtained, which measured 5 cm on each side, was immersed in 20 mL of hexane diisocyanate (HDI, first reaction agent). Next, the knitted cloth impregnated with HDI was sandwiched between aluminum foils and heated for 30 minutes at 130° C. After heating, the knitted cloth was taken out and immersed in 20 ml of butanol (BuOH, second reaction agent), and the knitted cloth was caused to react for 240 minutes at 100° C. The knitted cloth after the reaction was washed with THF, and thereby a knitted cloth of Example 4 to which water resistance-imparting materials (first reaction agent and second reaction agent) were bonded was obtained.

The knitted cloth obtained in (3), which measured 5 cm on each side, was evaluated as a knitted cloth of Comparative Example 3.

The knitted cloth obtained in (3), which measured 5 cm on each side, was immersed in 20 mL of hexane diisocyanate (HDI, first reaction agent). Next, the knitted cloth impregnated with HDI was sandwiched between aluminum foils and was heated for 30 minutes at 130° C. Subsequently, the knitted cloth was washed with THF, and thereby a knitted cloth of Comparative Example 4 in which only the first reaction agent was bonded was obtained.

(5) Evaluation of Contractibility

For the knitted cloth of Example 4 and the knitted cloths of Comparative Example 3 and Comparative Example 4, contractibility was evaluated. On each of the knitted cloths, a square that measured 3 cm on each side was drawn with a pencil, and this was used as an evaluation sample. The evaluation sample was laundered in a laundry mode "House Cleaning" of a washing machine (NA-VG1100L) manufactured by Panasonic Corporation. Next, spin-drying was performed for 15 minutes with the same washing machine, and the evaluation sample was air-dried for 120 minutes. The longitudinal and transverse lengths of the square before and after the laundry were respectively measured, and the contraction ratios in the longitudinal direction and the transverse direction were determined. The same test was carried out three times, and the average value of the three times was denoted as the evaluation results. The results are presented in Table 12.

(6) Evaluation of Texture

For the knitted cloth of Example 4 and the knitted cloths of Comparative Example 3 and Comparative Example 4, the texture was evaluated in three grades. The texture of the knitted cloth of Comparative Example 3 was designated as reference (B), and a case in which the feeling was superior to that was evaluated as A, while a case in which the texture was rough and the feeling was poor was evaluated as C. The results are presented in Table 12.

TABLE 12

| | Contraction ratio (%) | | |
|---|---|---|---|
| | Longitudinal direction | Transverse direction | Texture |
| Example 4 | 16 | 32 | A |
| Comparative Example 3 | 32 | 50 | B |
| Comparative Example 4 | 18 | 31 | C |

Test Example 4: Production and Evaluation of Fiber (Molded Article)

Example 5

(1) Preparation of Spinning Solution (Dope Solution)

200 mg of starch (manufactured by Wako Pure Chemical Industries, Ltd.) was dissolved in 11,400 mg of a solvent (dimethyl sulfoxide (DMSO) including 4% by weight of LiCl). 400 mg of phenyl isocyanate (manufactured by Tokyo Chemical Industry Co., Ltd.) was added to the solution thus obtained, and the solution was stirred for 4 hours at 90° C. Thereby, a hydroxyl group of starch reacted with an isocyanate group of phenyl isocyanate, and thereby a modified starch (modified hydroxyl group-containing polymer) to which a phenyl group (functioning functional group) was bonded through a urethane bond was obtained. The modification ratio (proportion at which hydroxyl groups have been converted to functioning functional groups) determined from the feed ratio was 100%.

The reaction liquid was cooled to room temperature, and then 300 mg of a freeze-dried powder of the modified fibroin (PRT799) was added to the reaction liquid. The reaction liquid was stirred for 12 hours at 90° C., the modified fibroin was dissolved in the reaction liquid, and a transparent spinning solution (dope solution) was obtained. The content of the modified starch in the spinning solution was 17% by mass based on the total content of the modified starch and starch.

(2) Production of Fiber (Molded Article) Including Modified Fibroin and Water Resistance-Imparting Material The spinning solution thus prepared was filtered through a metal filter having a sieve opening of 5 μm at 60° C. The spinning after filtration was left to stand in a 30-mL stainless steel syringe and was degassed. Subsequently, the spinning solution was discharged in a 100 mass % methanol coagulation bath through a solid nozzle having a needle diameter of 0.2 mm using nitrogen gas. The discharge temperature was 60° C., and the discharge pressure was 0.3 MPa. After coagulation, the raw yarn thus formed was wound at a winding speed of 3.00 m/min and was air-dried, and thereby a fiber including a modified fibroin and a water resistance-imparting material (modified starch) was obtained.

(3) Evaluation of Contractibility

The fiber thus obtained was cut into a length of about 10 cm, and the length (cm) of the yarn before immersion in water was measured. Next, the yarn was immersed in water bath at 40° C. for 1 minute. Subsequently, the yarn was taken out from the water bath and vacuum dried at room temperature for 15 minutes, and subsequently, the length of the yarn after drying was measured. The contraction ratio of the fiber was calculated by the following formula. The results are presented in Table 13.

Contraction ratio (%)={1−(length after immersion and drying/length before immersion)}×100

Example 6

(1) Preparation of Spinning Solution (Dope Solution)

253 mg of starch (manufactured by Wako Pure Chemical Industries, Ltd.) was dissolved in 7,600 mg of a solvent (dimethyl sulfoxide (DMSO) including 4% by weight of LiCl). To the reaction liquid thus obtained, 147 mg of acetic anhydride (manufactured by Wako Pure Chemical Industries, Ltd.) was added, and the reaction liquid was stirred for 4 hours at 90° C. Thereby, a hydroxyl group of starch reacted with acetic anhydride, and thus a modified starch (modified hydroxyl group-containing polymer) to which an acetyl group (functioning functional group) was bonded was obtained. The modification ratio (proportion at which hydroxyl groups have been converted to functioning functional groups) determined from the feed ratio was 100%.

The reaction liquid was cooled to room temperature, and then 2,000 mg of a freeze-dried powder of a modified fibroin (PRT799) was added to the reaction liquid. The reaction liquid was stirred for 12 hours at 90° C., thereby the modified fibroin was dissolved in the reaction liquid, and a transparent spinning solution (dope solution) was obtained. The content of the modified starch in the spinning solution was 17% by mass based on the total content of the modified starch and starch.

(2) Production of Fiber (Molded Article) Including Modified Fibroin and Water Resistance-Imparting Material A fiber including a modified fibroin and a water resistance-imparting material (modified starch) was obtained by a procedure similar to Example 5, using the spinning solution thus prepared.

(3) Evaluation of Contractibility

For the fiber thus obtained, an evaluation of contractibility was carried out by a procedure similar to that of Example 5. The results are presented in Table 13.

Example 7

(1) Preparation of Spinning Solution (Dope Solution)

215 mg of starch (manufactured by Wako Pure Chemical Industries, Ltd.) was dissolved in 7,600 mg of a solvent (dimethyl sulfoxide (DMSO) including 4% by weight of LiCl). To the reaction liquid thus obtained, 185 mg of acetic anhydride (manufactured by Wako Pure Chemical Industries, Ltd.) was added, and the reaction liquid was stirred for 4 hours at 90° C. Thereby, a hydroxyl group of starch reacted with acetic anhydride, and thus a modified starch (modified hydroxyl group-containing polymer) to which an acetyl group (functioning functional group) was bonded was obtained. For the modified starch, the modification ratio (proportion at which hydroxyl groups have been converted to functioning functional groups) determined from the feed ratio was 50%.

The reaction liquid was cooled to room temperature, and then 2,000 mg of a freeze-dried powder of a modified fibroin (PRT799) was added to the reaction liquid. The reaction liquid was stirred for 12 hours at 90° C., thereby the modified fibroin was dissolved in the reaction liquid, and a transparent spinning solution (dope solution) was obtained. The content of the modified starch in the spinning solution was 17% by mass based on the total content of the modified starch and starch.

(2) Production of Fiber (Molded Article) Including Modified Fibroin and Water Resistance-Imparting Material A fiber including a modified fibroin and a water resistance-imparting material (modified starch) was obtained by a procedure similar to Example 5, using the spinning solution thus prepared.

(3) Evaluation of Contractibility

For the fiber thus obtained, an evaluation of contractibility was carried out by a procedure similar to that of Example 5. The results are presented in Table 13.

Example 8

(1) Preparation of Spinning Solution (Dope Solution)

128 mg of polyvinyl alcohol (PVA) (manufactured by Wako Pure Chemical Industries, Ltd.) was dissolved in 7,600 mg of a solvent (dimethyl sulfoxide (DMSO) including 4% by weight of LiCl). To the reaction liquid thus obtained, 272 mg of phenyl isocyanate (manufactured by Tokyo Chemical Industry Co., Ltd.) was added, and the reaction liquid was stirred for 4 hours at 90° C. Thereby, a hydroxyl group of PVA reacted with phenyl isocyanate, and thus a modified PVA (modified hydroxyl group-containing polymer) to which a phenyl group (functioning functional group) was bonded by a urethane bond was obtained. The modification ratio (proportion at which hydroxyl groups have been converted to functioning functional groups) determined from the feed ratio was 100%.

The reaction liquid was cooled to room temperature, and then 2,000 mg of a freeze-dried powder of a modified fibroin (PRT799) was added to the reaction liquid. The reaction liquid was stirred for 12 hours at 90° C., thereby the modified fibroin was dissolved in the reaction liquid, and a transparent spinning solution (dope solution) was obtained. The content of the modified PVA in the spinning solution was 17% by mass based on the total content of the modified PVA and PVA.

(2) Production of Fiber (Molded Article) Including Modified Fibroin and Water Resistance-Imparting Material A fiber including a modified fibroin and a water resistance-imparting material (modified PVA) was obtained by a procedure similar to Example 5, using the spinning solution thus prepared.

(3) Evaluation of Contractibility

For the fiber thus obtained, an evaluation of contractibility was carried out by a procedure similar to that of Example 5. The results are presented in Table 13.

Example 9

(1) Preparation of Spinning Solution (Dope Solution)

193 mg of polyvinyl alcohol (PVA) (manufactured by Wako Pure Chemical Industries, Ltd.) was dissolved in 7,600 mg of a solvent (dimethyl sulfoxide (DMSO) including 4% by weight of LiCl). To the reaction liquid thus obtained, 207 mg of phenyl isocyanate (manufactured by Tokyo Chemical Industry Co., Ltd.) was added, and the reaction liquid was stirred for 4 hours at 90° C. Thereby, a hydroxyl group of PVA reacted with phenyl isocyanate, and thus a modified PVA (modified hydroxyl group-containing polymer) to which a phenyl group (functioning functional group) was bonded by a urethane bond was obtained. The modification ratio (proportion at which hydroxyl groups have been converted to functioning functional groups) determined from the feed ratio was 50%.

The reaction liquid was cooled to room temperature, and then 2,000 mg of a freeze-dried powder of a modified fibroin (PRT799) was added to the reaction liquid. The reaction liquid was stirred for 12 hours at 90° C., thereby the modified fibroin was dissolved in the reaction liquid, and a transparent spinning solution (dope solution) was obtained. The content of the modified PVA in the spinning solution was 17% by mass based on the total content of the modified PVA and PVA.

(2) Production of Fiber (Molded Article) Including Modified Fibroin and Water Resistance-Imparting Material A fiber including a modified fibroin and a water resistance-imparting material (modified PVA) was obtained by a procedure similar to Example 5, using the spinning solution thus prepared.

(3) Evaluation of Contractibility

For the fiber thus obtained, an evaluation of contractibility was carried out by a procedure similar to that of Example 5. The results are presented in Table 13.

Comparative Example 5

(1) Preparation of Spinning Solution (Dope Solution)

1,200 mg of a freeze-dried powder of a modified fibroin (PRT799) was added to a solvent (dimethyl sulfoxide (DMSO) including 4% by weight of LiCl) and dissolved therein by stirring the mixture for 12 hours at 90° C., and a transparent spinning solution (dope solution) was obtained.

(2) Production of Fiber

A fiber was obtained by a procedure similar to Example 5, using the spinning solution thus prepared.

(3) Evaluation of Contractibility

For the fiber thus obtained, an evaluation of contractibility was carried out by a procedure similar to that of Example 5. The results are presented in Table 13.

Comparative Example 6

(1) Preparation of Spinning Solution (Dope Solution)

3,000 mg of a freeze-dried powder of a modified fibroin (PRT799) and 600 mg of starch (manufactured by Wako Pure Chemical Industries, Ltd.) were added to a solvent (dimethyl sulfoxide (DMSO) including 4% by weight of LiCl). The solution was stirred for 12 hours at 90° C., thereby the modified fibroin was dissolved in the solution, and a transparent spinning solution (dope solution) was obtained.

(2) Production of Fiber

A fiber was obtained by a procedure similar to Example 5 using the spinning solution thus prepared.

(3) Evaluation of Contractibility

For the fiber thus obtained, an evaluation of contractibility was carried out by a procedure similar to Example 5. The results are presented in Table 13.

TABLE 13

| | Hydroxyl group-containing polymer | Functioning functional group | Modification ratio (%) | Proportion (%) of modified hydroxyl group-containing polymer*[1] | Contraction ratio (%) |
|---|---|---|---|---|---|
| Ex. 5 | Starch | Phenyl group | 100 | 17 | 10.8 |
| Ex. 6 | Starch | Acetyl group | 100 | 17 | 10.2 |
| Ex. 7 | Starch | Acetyl group | 50 | 17 | 10.1 |
| Ex. 8 | PVA | Phenyl group | 100 | 17 | 11.8 |
| Ex. 9 | PVA | Phenyl group | 50 | 17 | 11.0 |
| Comp. Ex. 5 | — | — | — | — | 16.3 |
| Comp. Ex. 6 | Starch | — | — | 0 | 16.0 |

*[1](Content of modified hydroxyl group-containing polymer/content of modified hydroxyl group-containing polymer body and hydroxyl group-containing polymer) × 100

In the molded articles (fibers of Examples 5 to 9) including a modified fibroin and a water resistance-imparting material (hydroxyl group-containing polymer (modified starch or modified PVA), the contraction ratio was decreased as compared to the molded articles (fibers of Comparative Examples 5 and 6) that did not include a water resistance-imparting material).

Sequence Listing

The invention claimed is:

1. A molded article, comprising: a modified fibroin; and a water resistance-imparting material, wherein the modified fibroin and the water resistance-imparting material are covalently bonded, and the water resistance-imparting material is at least one selected from a silicone-based polymer and a fluorine-based polymer.

2. The molded article according to claim 1, wherein the modified fibroin is a modified spider silk fibroin.

3. The article according to claim 1, wherein the molded article is a fiber.

4. A method for producing a molded article, the method comprising a step of covalently bonding a water resistance-imparting material to a precursor molded article comprising a modified fibroin, wherein the water resistance-imparting material is at least one selected from a silicone-based polymer and a fluorine-based polymer.

5. The method according to claim 4, wherein the step of bonding the water resistance-imparting material to the precursor molded article includes irradiating the precursor molded article with plasma in a state in which the water resistance-imparting material or a precursor of the water resistance-imparting material is brought into contact with the precursor molded article, and thereby covalently bonding the modified fibroin and the water resistance-imparting material.

6. The method according to claim 4, wherein the water resistance-imparting material is at least one selected from a silicone-based polymer and a fluorine-based polymer.

7. The method according to claim 4, wherein the modified fibroin is a modified spider silk fibroin.

8. The method according to claim 4, wherein the molded article is a fiber.

9. A method for producing a molded article, the method comprising a step of molding a raw material containing a modified fibroin and a water resistance-imparting material and thereby obtaining a molded article, wherein the water resistance-imparting material is a modified hydroxyl group-containing polymer formed as a result of a hydrophobic functional group being bonded to a hydroxyl group-containing polymer.

10. The method according to claim 9, wherein the molded article is a fiber.

* * * * *